US008383779B2

(12) United States Patent
Terrett et al.

(10) Patent No.: US 8,383,779 B2
(45) Date of Patent: Feb. 26, 2013

(54) HUMAN ANTIBODIES THAT BIND MESOTHELIN, AND USES THEREOF

(75) Inventors: Jonathan A. Terrett, Sunnyvale, CA (US); Sarah L. Pogue, Fremont, CA (US); Kristopher Toy, San Jose, CA (US); Lan Yang, Morgan Hill, CA (US); Chetana Rao-Naik, Walnut Creek, CA (US); Bingliang Chen, Alameda, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/587,572

(22) Filed: Aug. 16, 2012

(65) Prior Publication Data

US 2013/0028905 A1    Jan. 31, 2013

Related U.S. Application Data

(62) Division of application No. 12/681,215, filed as application No. PCT/US2008/078123 on Sep. 29, 2008, now Pat. No. 8,268,970.

(60) Provisional application No. 60/976,626, filed on Oct. 1, 2007, provisional application No. 60/991,692, filed on Nov. 30, 2007, provisional application No. 61/077,397, filed on Jul. 1, 2008.

(51) Int. Cl.
*C07K 16/00* (2006.01)
*C12P 21/08* (2006.01)

(52) U.S. Cl. .............. 530/387.1; 530/387.3; 530/388.15

(58) Field of Classification Search ........................ None
See application file for complete search history.

(56) References Cited

U.S. PATENT DOCUMENTS

| | | | |
|---|---|---|---|
| 4,912,227 A | 3/1990 | Kelly et al. |
| 4,978,757 A | 12/1990 | Kelly et al. |
| 5,070,092 A | 12/1991 | Kanda et al. |
| 5,084,468 A | 1/1992 | Saito et al. |
| 5,101,038 A | 3/1992 | Nakano et al. |
| 5,187,186 A | 2/1993 | Kanda et al. |
| 5,320,956 A | 6/1994 | Willingham et al. |
| 5,332,837 A | 7/1994 | Kelly et al. |
| 5,498,698 A | 3/1996 | Yamaguchi et al. |
| 5,525,337 A | 6/1996 | Willingham et al. |
| 5,641,780 A | 6/1997 | Amishiro et al. |
| 5,703,080 A | 12/1997 | Nakakura et al. |
| 5,723,318 A | 3/1998 | Yamaguchi et al. |
| 5,739,350 A | 4/1998 | Kelly et al. |
| 5,817,313 A | 10/1998 | Willingham et al. |
| 6,083,502 A | 7/2000 | Pastan et al. |
| 6,153,430 A | 11/2000 | Pastan et al. |
| 6,214,345 B1 | 4/2001 | Firestone et al. |
| 6,770,445 B1 | 8/2004 | Scholler et al. |
| 6,809,184 B1 | 10/2004 | Pastan et al. |
| 6,989,452 B2 | 1/2006 | Ng et al. |
| 7,081,518 B1 | 7/2006 | Pastan et al. |
| 7,087,600 B2 | 8/2006 | Ng et al. |
| 7,091,186 B2 | 8/2006 | Senter et al. |
| 7,129,261 B2 | 10/2006 | Ng et al. |
| 7,368,110 B2 | 5/2008 | Pastan et al. |
| 7,375,183 B1 | 5/2008 | Pastan et al. |
| 7,517,903 B2 | 4/2009 | Chen et al. |
| 7,553,816 B2 | 6/2009 | Senter et al. |
| 7,691,962 B2 | 4/2010 | Boyd et al. |
| 7,709,252 B2 | 5/2010 | Pastan et al. |
| 7,714,016 B2 | 5/2010 | Gangwar et al. |
| 2003/0040044 A1 | 2/2003 | Heavner et al. |
| 2005/0054056 A1 | 3/2005 | Ebel et al. |
| 2005/0266008 A1 | 12/2005 | Graziano et al. |
| 2005/0276812 A1 | 12/2005 | Ebens, Jr. et al. |
| 2006/0182751 A1 | 8/2006 | Gazzard et al. |
| 2006/0204506 A1 | 9/2006 | Ebel et al. |
| 2009/0226465 A1 | 9/2009 | Jackson |

FOREIGN PATENT DOCUMENTS

| | | |
|---|---|---|
| EP | 0 537 575 | 4/1993 |
| WO | WO 81/01145 | 4/1981 |
| WO | WO 96/10405 | 4/1996 |
| WO | WO 99/28471 | 6/1999 |
| WO | WO 00/50900 | 8/2000 |
| WO | WO 02/083180 | 10/2002 |
| WO | WO 02/096910 | 12/2002 |
| WO | WO 02/101075 | 12/2002 |
| WO | WO 02/102235 | 12/2002 |
| WO | WO 2004/065540 | 8/2004 |
| WO | WO 2005/030124 | 4/2005 |
| WO | WO 2005/112919 | 12/2005 |
| WO | WO 2006/099141 | 9/2006 |
| WO | WO 2006/124641 | 11/2006 |
| WO | WO 2007/038658 | 4/2007 |
| WO | WO 2007/051081 | 5/2007 |
| WO | WO 2007/059404 | 5/2007 |
| WO | WO 2007/089149 | 8/2007 |
| WO | WO 2008/083312 | 7/2008 |
| WO | WO 2008/103693 | 8/2008 |

OTHER PUBLICATIONS

Allen, T.M., "Ligand-Targeted Therapeutics in Anticancer Therapy, Nature Reviews: Cancer", vol. 2, pp. 750-763 (2002).
Bera, T.K. et al., "Mesothelin is Not Required for Normal Mouse Development or Reproduction", Molecular and Cellular Biology, vol. 20, No. 8, pp. 2902-2906 (2000).
Boger, D.L. et al., "CC-1065 and the Duocarmycins: Synthetic Studies", Chemical Reviews, vol. 97, No. 3, pp. 787-828 (1997).

(Continued)

*Primary Examiner* — Hong Sang
(74) *Attorney, Agent, or Firm* — Yuan Chao

(57) ABSTRACT

The present disclosure provides isolated monoclonal antibodies that specifically bind to mesothelin with high affinity, particularly human monoclonal antibodies. Preferably, the antibodies bind human mesothelin. In certain embodiments, the antibodies are capable of internalizing into mesothelin-expressing cells or are capable of mediating antigen dependent cellular cytotoxicity. The invention further provides anti-mesothelin antibodies that can inhibit the binding of mesothelin to the ovarian cancer antigen CA125. Nucleic acid molecules encoding the antibodies of this disclosure, expression vectors, host cells and methods for expressing the antibodies of this disclosure are also provided. Antibody-partner molecule conjugates, bispecific molecules and pharmaceutical compositions comprising the antibodies of this disclosure are also provided. This disclosure also provides methods for detecting mesothelin, as well as methods for treating cancers, such as mesotheliomas, pancreatic cancers and ovarian cancers, using an anti-mesothelin antibody of this disclosure.

7 Claims, 18 Drawing Sheets

OTHER PUBLICATIONS

Boger, D.L. et al., "CC-1065 and the Duocarmycins: Understanding their Biological Function through Mechanistic Studies", Angew. Chem. Int. Ed. Engl., vol. 35, pp. 1438-1474 (1996).

Boger, D.L. et al., "Parallel Synthesis and Evaluation of 132 (+)-1,2,9,9a-Tetrahydrocyclopropa[c]benz[e]indol-4-one (CBI) Analogues of CC-1065 and the Duocarmycins Defining the Contribution of the DNA-Binding Domain", J. Org. Chem., vol. 66, No. 20, pp. 6654-6661 (2001).

Brinkmann et al., Int. J. Cancer 1997, 71, 638-644, "Cloning and expression of the recombinant Fab fragment of monoclonal antibody K1 that react with mesothelin present on mesotheliomas and ovarian cancer".

Carl, P.L. et al., "A Novel Connector Linkage Applicable in Prodrug Design", Journal of Medicinal Chemistry, vol. 24, No. 5, p. 479-480 (1981).

Chang et al., Cancer Research 1992, 52(1), 181-186, "Characterization of the Antigen (CAK1) Recognized by Monoclonal Antibody K1 Present on Ovarian Cancers and Normal Mesothelin".

Chang, K. et al., "Molecular cloning of mesothelin, a differentiation antigen present on mesothelium, mesotheliomas, and ovarian cancers", Proc. Natl. Acad. Sci. USA, vol. 93, pp. 136-140 (1996).

de Groot, F.M.H. et al., "Elongated Multiple Electronic Cascade and Cyclization Spacer Systems in Activatible Anticancer Prodrugs for Enhanced Drug Release", J. Org. Chem., vol. 66, No. 26, pp. 8815-8830 (2001).

de Groot, F.M.H. et al., "Synthesis and Biological Evaluation of Novel Prodrugs of Anthracyclines for Selective Activation by the Tumor-Associated Protease Plasmin", Journal of Medicinal Chemistry, vol. 42, No. 25, pp. 5277-5283 (1999).

de Groot, F.M.H. et al., "Synthesis and Biological Evaluation of 2'-Carbamate-Linked and 2'-Carbonate-Linked Prodrugs of Paclitaxel: Selective Activation by the Tumor-Associated Protease Plasmin", Journal of Medicinal Chemistry, vol. 43, No. 16, pp. 3093-3102 (2000).

Dubowchik, G.M. et al., "Cathepsin B-Sensitive Dipeptide Prodrugs. 2. Models of Anticancer Drugs Paclitaxel (Taxon®), Mitomycin C and Doxorubicin", Bioorganic & Medicinal Chemistry Letters, vol. 8, pp. 3347-3352 (1998).

Gubbels, J.A.A. et al., "Mesothelin-MUC16 binding is a high affinity, N-glycan dependent interaction that facilitates peritoneal metastasis of ovarian tumors", Molecular Cancer, 5:50 (2006).

Hassan, R. et al., "Mesothelin: A New Target for Immunotherapy", Clinical Cancer Research, vol. 10, pp. 3937-3942 (2004).

Kojima, T. et al., "Molecular Cloning and Expression of Megakaryocyte Potentiating Factor cDNA", The Journal of Biological Chemistry, vol. 270, No. 37, pp. 21984-21990 (1995).

Li et al., Anticancer Research 2004, 24(3A), 1327-1335, "Cyttoxic activity of the recombinant anti-mesothelin immunotoxin, SS1 (DSFV) PE38, towards tumor cell lines established from ascites of patients with peritoneal mesothelioma".

Office Action date May 17, 2012 by the Chinese Patent Office for Chinese Patent Application No. 200880110024.5.

Pastan, I. et al., "Immunotoxins in cancer therapy", Current Opinion in Investigational Drugs, vol. 3, No. 7, pp. 1089-1091 (2002).

Payne, G., "Progress in immunoconjugate cancer therapeutics", Cancer Cell, vol. 3, pp. 207-212 (2003).

Rump, A. et al., "Binding of Ovarian Cancer Antigen CA125/MUC16 to Mesothelin Mediates Cell Adhesion", The Journal of Biological Chemistry, vol. 279, No. 10, pp. 9190-9198 (2004).

Saito, G. et al., "Drug delivery strategy utilizing conjugation via reversible disulfide linkages: role and site of cellular reducing activities", Advanced Drug Delivery Reviews, vol. 55, pp. 199-215 (2003).

Senter, P.D. et al., "Selective activation of anticancer prodrugs by monoclonal antibody-enzyme conjugates", Advanced Drug Delivery Reviews, vol. 53, pp. 247-264 (2001).

Toki, B.E. et al., "Protease-Mediated Fragmentation of p-Amidobenzyl Ethers: a New Strategy for the Activation of Anticancer Prodrugs", J. Org. Chem., vol. 67, No. 6, pp. 1866-1872 (2002).

Trail, P.A. et al., "Monoclonal antibody drug immunoconjugates for targeted treatment of cancer", Cancer Immunol. Immunother., vol. 52, pp. 328-337 (2003).

Written Opinion dated Jun. 6, 2012 by the Intellectual Property Office of Singapore for Singapore Patent Application No. 2010002166-5.

Yamaguchi, N. et al., "A Novel Cytokine Exhibiting Megakaryocyte Potentiating Activity from a Human Pancreatic Tumor Cell Line HPC-Y5", The Journal of Biological Chemistry, vol. 269, No. 2, pp. 805-808 (1994).

Bendig, "Humanization of Rodent Monoclonal Antibodies by CDR Grafting," Methods: A Companion to Methods in Enzymology, vol. 8, 83-93 (1995).

Colman, "Effects of amino acid sequence change on antibody-antigen interactions," Research in Immunology, vol. 15, 33-36 (1994).

Greenspan et al., "Defining epitopes: it's not as easy as it sounds," Nature Biotechnology, vol. 7, 936-937 (1999).

Paul, Fundamentals Immunology, $3^{rd}$ Ed., 1993, pp. 292-295.

Rudikoff et al., "Single amino acid substitution altering antigen-binding specificity," Proc. Nat'l Acad. Sci. (USA), vol. 79, No. 6, 1979-1983 (1982).

European supplementary Search Report and search opinion, Apr. 12, 2012 for European Patent Application No. 08836490.

Chowdury et al., "Isolation of a high-affinity stable single-chain Fv specific for mesothelin from DNA-immunized mice by phage display and construction ofa recombinant immunotoxin with anti-tumor activity," Proc. Nat'l Acad. Sci. (USA), vol. 95, No. 2, 669-674 (1998).

Hassan et al., "Anti-tumor activity of K1-LYSPE38QQR, an immunotoxin targeting mesothelin, a cell surface antigen overexpressed in ovarian cancer and malignant mesothelioma," J. Immunotherapy:, vol. 23, No. 4, 473-479 (2000).

Nicolaides, "MoRab-009,a monoclonal antibody that specifically targets mesothelin, a cell surface tumor pancreatic tumor adhesion molecule over-expressed in pancreatic, ovarian, and lung cancer and mesothelioma," Proc. Annual. Mtg. Am. Assoc. Cancer Research, vol. 48, 156-157 (2007).

Sheehan, "Effecs of Histamine and 5-Hydroxytryptamine on the Growth Rate of Xenografted Human Bronchogenic Carcinomas," Exper. Clinical Pharmacology (Moscow), vol. 23, No. 6-7, 465-471 (1996).

Anti-Mesothelin 3C10 VH

V segment:     3-33
    D segment: 3-10
    J segment:     JH4b

```
            Q   V   Y   L   V   E   S   G   G   G   V   V   Q   P   G   R   S   L
  1         CAG GTG TAC CTG GTG GAG TCT GGG GGA GGC GTG GTC CAG CCC GGG AGG TCC CTG
                                                                          CDR1
                                                                          ~~~~~~~~~~~~~~~~~~
            R   L   S   C   A   A   S   G   I   T   F   S   I   Y   G   M   H   W
 55         AGA CTC TCC TGT GCA GCG TCT GGA ATC ACC TTC AGT ATC TAT GGC ATG CAC TGG
                                                                          CDR2
                                                                          ~~~~~~~~~~~~~~~~~~
            V   R   Q   A   P   G   K   G   L   E   W   V   A   V   I   W   Y   D
109         GTC CGC CAG GCT CCA GGC AAG GGG CTG GAG TGG GTG GCA GTT ATA TGG TAT GAT
                        CDR2
            ~~~~~~~~~~~~~~~~~~~~~~~~~~~~~~~~~~~~~~~~~~~~~~~
            G   S   H   E   Y   Y   A   D   S   V   K   G   R   F   T   I   S   R
163         GGA AGT CAT GAA TAC TAT GCA GAC TCC GTG AAG GGC CGA TTC ACC ATC TCC AGA

D   N   S   K   N   T   L   Y   L   M   N   S   L   R   A   E   D
217         GAC AAT TCC AAG AAC ACG CTG TAT CTG CTA ATG AAC AGC CTG AGA GCC GAG GAC
                                                              CDR3
                                                              ~~~~~~~~~~~~~~~~~~~~~~~~~~~~~~~~
            T   A   V   Y   Y   C   A   R   D   G   D   Y   Y   D   S   G   S   P
271         ACG GCT GTG TAT TAC TGT GCG AGA GAT GGC GAT TAT TAT GAT TCG GGG AGT CCT
              CDR3
            ~~~~~~~~~~~~
            L   D   Y   W   G   Q   G   T   L   V   T   V   S   S
325         CTT GAC TAC TGG GGC CAG GGA ACC CTG GTC ACC GTC TCC TCA
```

FIGURE 1A

Anti-Mesothelin 3C10 VK

V segment:    L6
J segment:    JK4

```
           E   I   V   L   T   Q   S   P   A   T   L   S   L   S   P   G   E   R
  1       GAA ATT GTG TTG ACA CAG TCT CCA GCC ACC CTG TCT TTG TCT CCA GGG GAA AGA

CDR1
                                    ~~~~~~~~~~~~~~~~~~~~~~~~~~~~~~~~~~~~~~~~~~~~
           A   T   L   S   C   R   A   S   Q   S   V   S   S   Y   L   A   W   Y
  55      GCC ACC CTC TCC TGC AGG GCC AGT CAG AGT GTT AGC AGC TAC TTA GCC TGG TAC

CDR2
                                                          ~~~~~~~~~~~~~~~~~~~~~~~
           Q   Q   K   P   G   Q   A   P   R   L   L   I   Y   D   A   S   N   R
  109     CAA CAG AAA CCT GGC CAG GCT CCC AGG CTC CTC ATC TAT GAT GCA TCC AAC AGG

CDR2
          ~~~~~~~~~
           A   T   G   I   P   A   R   F   S   G   S   G   S   G   T   D   F   T
  163     GCC ACT GGC ATC CCA GCC AGG TTC AGT GGC AGT GGG TCT GGG ACA GAC TTC ACT

CDR3
                                                                          ~~~~~~~~
           L   T   I   S   S   L   E   P   E   D   F   A   V   Y   Y   C   Q   Q
  217     CTC ACC ATC AGC AGC CTA GAG CCT GAA GAT TTT GCA GTT TAT TAC TGT CAG CAG

CDR3
          ~~~~~~~~~~~~~~~~~~~~~~~~~~~~~~~~
           R   S   N   W   P   L   T   F   G   G   G   T   K   V   E   I   K
  271     CGT AGC AAC TGG CCG CTC ACT TTC GGC GGA GGG ACC AAG GTG GAG ATC AAA
```

FIGURE 1B

Anti-Mesothelin 6A4 VH

V segment:       3-33
    D segment:3-10
    J segment:       JH4b

```
          Q   V   H   L   V   E   S   G   G   V   V   Q   P   G   R   S   L
1        CAG GTG CAC CTG GTG GAG TCT GGG GGA GGC GTG GTC CAG CCT GGG AGG TCC CTG
                                                                CDR1
                                                                ~~~~~~~~~~~~~~~
          R   L   S   C   V   A   S   G   I   T   F   R   I   Y   G   M   H   W
55       AGA CTC TCC TGT GTA GCG TCT GGA ATC ACC TTC AGG ATC TAT GGC ATG CAC TGG
                                                                    CDR2
                                                                    ~~~~~~~~~~~
          V   R   Q   A   P   G   K   G   L   E   W   V   A   V   L   W   Y   D
109      GTC CGC CAG GCT CCA GGC AAG GGG CTG GAG TGG GTG GCA GTT TTA TGG TAT GAT
                         CDR2
         ~~~~~~~~~~~~~~~~~~~~~~~~~~~~~~~~~~~~~~~~~~~~~~~~~~~~~~~~~
          G   S   H   E   Y   Y   A   D   S   V   K   G   R   F   T   I   S   R
163      GGA AGT CAT GAA TAC TAT GCA GAC TCC GTG AAG GGC CGA TTC ACC ATC TCC AGA

D   N   S   K   N   T   L   Y   L   Q   M   N   S   L   R   A   E   D
217      GAC AAT TCC AAG AAC ACG CTA TAT CTG CAA ATG AAC AGC CTG AGA GCC GAG GAC
                                                        CDR3
                                                        ~~~~~~~~~~~~~~~~~~~~~~~
          T   A   I   Y   Y   C   A   R   D   G   D   Y   Y   D   S   G   S   P
271      ACG GCT ATA TAT TAC TGT GCG AGA GAT GGC GAT TAC TAT GAT TCG GGG AGT CCT
            CDR3
         ~~~~~~~~~~
          L   D   Y   W   G   Q   G   T   L   V   T   V   S   S
325      CTT GAC TAC TGG GGC CAG GGA ACC CTG GTC ACC GTC TCC TCA
```

FIGURE 2A

Anti-Mesothelin 6A4 VK

V segment:   L6
J segment:   JK4

```
        E   I   V   L   T   Q   S   P   A   T   L   S   L   S   P   G   E   R
1       GAA ATT GTG TTG ACA CAG TCT CCA GCC ACC CTG TCT TTG TCT CCA GGG GAA AGA
                                            CDR1
                                            ~~~~~~~~~~~~~~~~~~~~~~~~~~~~~~~~~~~
        A   T   L   S   C   R   A   S   Q   S   V   S   S   Y   L   A   W   Y
55      GCC ACC CTC TCC TGC AGG GCC AGT CAG AGT GTT AGC AGC TAC TTA GCC TGG TAC
                                                                    CDR2
                                                                    ~~~~~~~~~~~~
        Q   Q   K   P   G   Q   A   P   R   L   L   I   Y   D   A   S   N   R
109     CAA CAG AAA CCT GGC CAG GCT CCC AGG CTC CTC ATC TAT GAT GCA TCC AAC AGG

CDR2
        ~~~~~~~~
        A   T   G   I   P   A   R   F   S   G   S   G   S   G   T   D   F   T
163     GCC ACT GGC ATC CCA GCC AGG TTC AGT GGC AGT GGG TCT GGG ACA GAC TTC ACT
                                                                            CDR3
                                                                            ~~~~~~~
        L   T   I   S   S   L   E   P   E   D   F   A   V   Y   Y   C   Q   Q
217     CTC ACC ATC AGC AGC CTA GAG CCT GAA GAT TTT GCA GTT TAT TAC TGT CAG CAG
            CDR3
            ~~~~~~~~~~~~~~~~~~~~~~~~~
        R   S   N   W   P   L   T   F   G   G   G   T   K   V   E   I   K
271     CGT AGC AAC TGG CCG CTC ACT TTC GGC GGA GGG ACC AAG GTG GAG ATC AAA
```

FIGURE 2B

Anti-Mesothelin 7B1 VH

V segment:      3-7
    D segment: 3-10
    J segment:      JH6b

```
          E   V   H   L   V   E   S   G   G   G   L   V   Q   P   G   G   S   L
1        GAG GTT CAC CTG GTG GAG TCT GGG GGA GGC TTG GTC CAG CCT GGG GGT TCC CTG
                                                                    CDR1
                                                            ~~~~~~~~~~~~~~~~~~~~
          R   L   S   C   A   A   S   G   F   T   F   S   R   Y   W   M   S   W
55       AGA CTC TCC TGT GCA GCC TCT GGA TTC ACC TTT AGT AGA TAC TGG ATG AGC TGG
                                                                           CDR2
                                                                   ~~~~~~~~~~~~~
          V   R   Q   A   Q   G   K   G   L   E   W   V   A   S   I   K   Q   A
109      GTC CGC CAG GCT CAA GGG AAA GGG CTG GAG TGG GTG GCC AGC ATA AAG CAA GCT
                    CDR2
         ~~~~~~~~~~~~~~~~~~~~~~~~~~~~~~~~~~~~~~~~~~~~~~~~~~~
          G   S   E   K   T   Y   V   D   S   V   K   G   R   F   T   I   S   R
163      GGA AGT GAG AAA ACC TAT GTG GAC TCT GTG AAG GGC CGA TTC ACC ATC TCC AGA

D   N   A   K   N   S   L   S   L   Q   M   N   S   L   R   A   E   D
217      GAC AAC GCC AAG AAC TCA CTG TCT CTG CAA ATG AAC AGC CTG AGA GCC GAG GAC
                                                            CDR3
                                                    ~~~~~~~~~~~~~~~~~~~~~~~~~~~
          T   A   V   Y   Y   C   A   R   E   G   A   Y   Y   Y   D   S   A   S
271      ACG GCT GTT TAT TAC TGT GCG AGG GAG GGG GCA TAT TAC TAT GAT TCG GCG AGT
                    CDR3
         ~~~~~~~~~~~~~~~~~~~~~~~~~~~~~~~~~~~~~~~~~~~~~~~~
          Y   Y   P   Y   Y   Y   Y   Y   S   M   D   V   W   G   Q   G   T   T
325      TAT TAC CCT TAC TAC TAC TAC TAC AGT ATG GAC GTC TGG GGC CAA GGG ACC ACG

V   T   V   S   S
379      GTC ACC GTC TCC TCA
```

FIGURE 3A

Anti-Mesothelin 7B1 VK

V segment:    A27
J segment:    JK2

```
            E   I   V   L   T   Q   S   P   G   T   L   S   L   S   P   G   E   R
1           GAA ATT GTG TTG ACG CAG TCT CCA GGC ACC CTG TCT TTG TCT CCA GGG GAA AGA
                                            CDR1
                                            ~~~~~~~~~~~~~~~~~~~~~~~~~~~~~~~~~~~~~~~~~
            A   T   L   S   C   R   A   S   Q   S   V   S   S   S   Y   L   A   W
55          GCC ACC CTC TCC TGC AGG GCC AGT CAG AGT GTT AGC AGC AGC TAC TTA GCC TGG
                                                                        CDR2
                                                                        ~~~~~~~~~~~~~~~
            Y   Q   Q   K   P   G   Q   A   P   R   L   L   I   Y   G   A   S   S
109         TAC CAG CAG AAA CCT GGC CAG GCT CCC AGG CTC CTC ATC TAT GGT GCA TCC AGC
            CDR2
            ~~~~~~~~~~~~~~~
            R   A   T   G   I   P   D   R   F   S   G   S   G   S   G   T   D   F
163         AGG GCC ACT GGC ATC CCA GAC AGG TTC AGT GGC AGT GGG TCT GGG ACA GAC TTC
                                                                                CDR3
                                                                                ~~~
            T   L   T   I   S   R   L   E   P   E   D   F   A   V   Y   Y   C   Q
217         ACT CTC ACC ATC AGC AGA CTG GAG CCT GAA GAT TTT GCA GTG TAT TAC TGT CAG
                    CDR3
                    ~~~~~~~~~~~~~~~~~~~~~~~~~~~~~~~~~~~~
            Q   Y   G   S   S   Q   Y   T   F   G   Q   G   T   K   L   E   I   K
271         CAG TAT GGT AGC TCA CAG TAC ACT TTT GGC CAG GGG ACC AAG CTG GAG ATC AAA
```

FIGURE 3B

Anti-Mesothelin 3C10 and 6A4 VH regions

```
                                                              CDR1
3-33 germline   Q V Q L V E S G G G V V Q P G R S L R L S C A A S G F T F S S Y G M H W - -
3C10 VH         - - - - - Y - - - - - - - - - - - - - - - - - - - - - H - - H - - - - - - -
6A4 VH          - - - H - - - - - - - - - - - - - - - - - V - - - - - H - - R I - - - - - -

CDR2
3-33 germline   V R Q A P G K G L E W V A V I W Y D G S N K Y Y A D S V K G R F T I S R - -
3C10 VH         - - - - - - - - - - - - - - - - - - - - H E - - - - - - - - - - - - - - - -
6A4 VH          - - - - - - - - - - - - - - - L - - - - H E - - - - - - - - - - - - - - - -

CDR3
3-33 germline   D N S K N T L Y L Q M N S L R A E D T A V Y Y C A R - - D G D Y Y D S G S P
3C10 VH         - - - - - - - - - L - - - - - - - - - - - - - - - - - - D G D Y Y D S G S P
6A4 VH          - - - - - - - - - - - - - - - - - - - - - - - - - - - H D G D Y Y D S G S P JH4b germline     D Y W G Q G T L V T V S S          (JH4b)
3C10 VH           L - - - - - - - - - - - -          (JH4b)
6A4 VH            L - - - - - - - - - - - -
```

FIGURE 4

Anti-Mesothelin 3C10 and 6A4 VK regions

```
                                                        CDR1
L6 germline      E I V L T Q S P A T L S L S P G E R A T L S C R A S Q S V S S
3C10 VK          - - - - - - - - - - - - - - - - - - - - - - - - - - - - - -
6A4 VK           - - - - - - - - - - - - - - - - - - - - - - - - - - - - - -

CDR2
L6 germline      Y L A W Y Q Q K P G Q A P R L L I Y D A S N R A T G I P A R F
3C10 VK          - - - - - - - - - - - - - - - - - - - - - - - - - - - - - -
6A4 VK           - - - - - - - - - - - - - - - - - - - - - - - - - - - - - -

CDR3
L6 germline      S G S G S G T D F T L T I S S L E P E D F A V Y Y C Q Q R S N
3C10 VK          - - - - - - - - - - - - - - - - - - - - - - - - - - - - - -
6A4 VK           - - - - - - - - - - - - - - - - - - - - - - - - - - - - - -

L6 germline      W P
JK4 germline         L T F G G G T K V E I K        (JK4)
3C10 VK          - -  - - - - - - - - - - -        (JK4)
6A4 VK           - -  - - - - - - - - - - -
```

FIGURE 5

Anti-Mesothelin 7B1 VH region

```
                                                    CDR1
3-7 germline    E V Q L V E S G G G L V Q P G G S L R L S C A A S G F T F S S Y W M S W V R
7B1 VH          - - - H - - - - - - - - - - - - - - - - - - - - - - - - - - R - - - - - - -

CDR2
3-7 germline    Q A P G K G L E W V A N I K Q D G S E K Y Y V D S V K G R F T I S R D N A K
7B1 VH          - - - Q - - - - - - - S - - - - - - - - T - - - - - - - - - - - - - - - - -

CDR3
3-7 germline    N S L Y L Q M N S L R A E D T A V Y Y C A R
JH6b germline                                               E G A Y Y Y D S A S Y Y P   Y Y Y
7B1 VH          - - - - - - - S - - - - - - - - - - - - - -  - - - - - - - - - - - -   - - -

CDR3
JH6b germline   Y Y G M D V W G Q G T T V T V S S        (JH6b)
7B1 VH          - - S - - - - - - - - - - - - - -
```

FIGURE 6

Anti-Mesothelin 7B1 VK region

```
                                                     CDR1
A27 germline    E I V L T Q S P G T L S L S P G E R A T L S C R A S Q S V S S
7B1 VK          - - - - - - - - - - - - - - - - - - - - - - - - - - - - - -

CDR1                                      CDR2
A27 germline    S Y L A W Y Q Q K P G Q A P R L L I Y G A S S R A T G I P D R
7B1 VK          - - - - - - - - - - - - - - - - - - - - - - - - - - - - - -

CDR3
A27 germline    F S G S G S G T D F T L T I S R L E P E D F A V Y Y C Q Q Y G
7B1 VK          - - - - - - - - - - - - - - - - - - - - - - - - - - - - - -

CDR3
A27 germline    S S         Y T F G Q G T K L E I K
JK2 germline              - - - - - - - - - - - - -     (JK2)
7B1 VK          - - Q - - - - - - - - - - - - -
```

FIGURE 7

HUMAN ANTIBODIES THAT BIND MESOTHELIN, AND USES THEREOF

CROSS-REFERENCE TO RELATED APPLICATIONS

This application is a divisional of application Ser. No. 12/681,215, filed Apr. 1, 2010, now U.S. Pat. No. 8,268,970 B2; which is the National Stage of International Application No. PCT/US2008/078123, filed Sep. 29, 2008; which claims the benefit under 35 U.S.C. §119(e) of U.S. Provisional Applications Nos. 60/976,626, filed Oct. 1, 2007; 60/991,692, filed Nov. 30, 2007; and 61/077,397, filed Jul. 1, 2008; the disclosures of which are incorporated herein by reference.

SEQUENCE LISTING

Incorporated herein by reference in its entirety is a Sequence Listing named "SEQT_M00192USDIV[2].txt", comprising SEQ ID NO:1 through SEQ ID NO:43, which include nucleic acid and/or amino acid sequences disclosed herein. The Sequence Listing has been submitted herewith in ASCII text format via EFS-Web, and thus constitutes both the paper and computer readable form thereof. The Sequence Listing was first created using PatentIn 3.5 on Jul. 6, 2012, and is 19 KB in size.

BACKGROUND OF THE INVENTION

Mesothelin is a glycoprotein present on the surface of cells of the mesothelial lining of the peritoneal, pleural and pericardial body cavities. It was originally purified from the human pancreatic cancer cell line HPC-Y5 and was shown to have megakaryocyte potentiating ability and hence named megakaryocyte potentiating factor (MPF) (Yamaguchi et al. (1994) *J. Biol. Chem.* 269:805-808). The mesothelin cDNA was cloned from a library prepared from the HPC-Y5 cell line (Kojima et al. (1995) *J. Biol. Chem.* 270:21984-21990). The cDNA also was cloned using the monoclonal antibody K1, which recognizes mesotheliomas (Chang and Pastan (1996) *Proc. Natl. Acad. Sci. USA* 93:136-40). Structurally, mesothelin is expressed on the cell surface as a 60 kDa precursor polypeptide, which is proteolytically processed into a 31 kDa shed component (corresponding to MPF) and a 40 kDa membrane bound component (Hassan et al. (2004) *Clin. Cancer. Res.* 10:3937-3942).

In addition to being expressed on normal mesothelial cells, mesothelin is overexpressed in several types of human tumors, including all mesotheliomas, many ovarian and pancreatic cancers, and some stomach, lung and endometrial cancers. For example, mesothelin is expressed on approximately 70% of all ovarian cancers, approximately 82% of papillary, serous adenocarcinomas, approximately 83% of all pancreatic adenocarcinomas and approximately 86% of all ductal pancreatic adenocarcinomas.

Mutant mice have been prepared in which the mesothelin gene was disrupted by homologous recombination (Bera, T. K. and Pastan, I. (2000) *Mol. Cell. Biol.* 20:2902-2906). No anatomical, hematologic or reproductive abnormalities were detected, indicating that mesothelin function is not essential for growth or reproduction, at least in those mice.

Mesothelin specifically interacts with CA125 (also known as MUC-16), a mucin-like glycoprotein present on the surface of tumor cells that previously had been identified as an ovarian cancer antigen. Further, binding of CA125 to membrane-bound mesothelin mediates heterotypic cell adhesion and CA125 and mesothelin are co-expressed in advanced grade ovarian adenocarcinoma (Rump, A. et al. (2004) *J. Biol. Chem.* 279:9190-9198). Expression of mesothelin in the lining of the peritoneum correlates with the preferred site of metastasis formation of ovarian cancer and mesothelin-CA125 binding is thought to facilitate peritoneal metastasis of ovarian tumors (Gubbels, J. A. et al. (2006) *Mol. Cancer.* 5:50).

In view of the foregoing, additional agents for modulating the activity of mesothelin are of interest.

SUMMARY

The present disclosure provides isolated monoclonal antibodies, in particular human ones, which specifically bind mesothelin and have desirable properties such as high affinity binding to human mesothelin, internalization by cells expressing mesothelin, inhibition of mesothelin binding to CA125, and/or the mediation of antibody dependent cellular cytotoxicity (ADCC). The antibodies of the invention can be used, for example, to detect mesothelin or to inhibit the growth of cells expressing mesothelin, such as mesothelin-expressing tumor cells.

In one aspect, the invention pertains to an isolated human monoclonal antibody, or an antigen-binding portion thereof, wherein the antibody binds human mesothelin and exhibits at least one of the following properties:
  (a) binds to human mesothelin with a $K_D$ of $1 \times 10^{-8}$ M or less;
  (b) is internalized by mesothelin-expressing cells;
  (c) inhibits binding of mesothelin to ovarian cancer antigen CA125;
  (d) exhibits ADCC against mesothelin expressing cells; and
  (e) inhibits growth of mesothelin-expressing cells in vivo when conjugated to a cytotoxin.

Preferably, the antibody exhibits at least two of properties (a), (b), (c), (d), and (e). More preferably, the antibody exhibits at least three of properties (a), (b), (c), (d), and (e). More preferably, the antibody exhibits four of properties (a), (b), (c), (d), and (e). Even, more preferably, the antibody exibits all five of properties (a), (b), (c), (d), and (e). In another preferred embodiment, the antibody binds to mesothelin with a $K_D$ of $5 \times 10^{-9}$ M or less. In yet another preferred embodiment, the antibody inhibits growth of mesothelin-expressing tumor cells in vivo when the antibody is conjugated to a cytotoxin.

In another aspect, the invention pertains to an isolated human monoclonal antibody, or antigen binding portion thereof, wherein the antibody cross-competes for binding to an epitope on human mesothelin that is recognized by a reference antibody having:
  (a) a heavy chain variable region ($V_H$) comprising the amino acid sequence of SEQ ID NO: 19 and a light chain variable region ($V_L$) comprising the amino acid sequence of SEQ ID NO: 22;
  (b) a $V_H$ comprising the amino acid sequence of SEQ ID NO: 20 and a $V_L$ comprising the amino acid sequence of SEQ ID NO: 23; or
  (c) a $V_H$ comprising the amino acid sequence of SEQ ID NO: 21 and a $V_L$ comprising the amino acid sequence of SEQ ID NO: 24.

The reference antibodies described above are referred to hereinbelow as Reference Antibodies (a), (b), and (c), respectively.

In a preferred embodiment, the reference antibody comprises a $V_H$ comprising the amino acid sequence of SEQ ID NO: 19 and a $V_L$ comprising the amino acid sequence of SEQ ID NO: 22. In another preferred embodiment, the reference antibody comprises a $V_H$ comprising the amino acid sequence of SEQ ID NO: 20 and a $V_L$ comprising the amino acid sequence of SEQ ID NO: 23. In yet another preferred embodiment, the reference antibody comprises a $V_H$ comprising the amino acid sequence of SEQ ID NO: 21 and a $V_L$ comprising the amino acid sequence of SEQ ID NO: 24.

In another aspect, the invention pertains to an isolated monoclonal antibody, or an antigen-binding portion thereof, comprising a $V_H$ that is the product of or derived from a human $V_H$ 3-33 gene or a human $V_H$ 3-7 gene, wherein the antibody specifically binds human mesothelin. In another aspect, the invention pertains to an isolated monoclonal antibody, or an antigen-binding portion thereof, comprising a $V_L$ that is the product of or derived from a human $V_K$ L6 gene or a human $V_K$ A27 gene, wherein the antibody specifically binds human mesothelin. In a preferred embodiment, the invention provides an isolated monoclonal antibody, or an antigen-binding portion thereof, comprising:

(a) a $V_H$ that is the product of or derived from a human $V_H$ 3-33 gene and a $V_L$ that is the product of or derived from a human $V_K$ L6 gene; or (b) a $V_H$ that is the product of or derived from a human $V_H$ 3-7 gene and a $V_L$ that is the product of or derived from a human $V_K$ A27 gene;

wherein the antibody specifically binds human mesothelin.

A particularly preferred antibody, or antigen-binding portion thereof ("Embodiment A"), comprises:

(a) a heavy chain variable region CDR1 comprising SEQ ID NO: 1;
(b) a heavy chain variable region CDR2 comprising SEQ ID NO: 4;
(c) a heavy chain variable region CDR3 comprising SEQ ID NO: 7;
(d) a light chain variable region CDR1 comprising SEQ ID NO: 10;
(e) a light chain variable region CDR2 comprising SEQ ID NO: 13; and
(f) a light chain variable region CDR3 comprising SEQ ID NO: 16.

Another particularly preferred antibody, or antigen-binding portion thereof ("Embodiment B"), comprises:

(a) a heavy chain variable region CDR1 comprising SEQ ID NO: 2;
(b) a heavy chain variable region CDR2 comprising SEQ ID NO: 5;
(c) a heavy chain variable region CDR3 comprising SEQ ID NO: 8;
(d) a light chain variable region CDR1 comprising SEQ ID NO: 11;
(e) a light chain variable region CDR2 comprising SEQ ID NO: 14; and
(f) a light chain variable region CDR3 comprising SEQ ID NO: 17.

Another particularly preferred antibody, or antigen-binding portion thereof ("Embodiment C"), comprises:

(a) a heavy chain variable region CDR1 comprising SEQ ID NO: 3;
(b) a heavy chain variable region CDR2 comprising SEQ ID NO: 6;
(c) a heavy chain variable region CDR3 comprising SEQ ID NO: 9;
(d) a light chain variable region CDR1 comprising SEQ ID NO: 12;
(e) a light chain variable region CDR2 comprising SEQ ID NO: 15; and
(f) a light chain variable region CDR3 comprising SEQ ID NO: 18.

In another aspect, the invention pertains to an isolated monoclonal antibody, or antigen binding portion thereof, comprising: (a) a $V_H$ comprising an amino acid sequence selected from the group consisting of SEQ ID NOs: 19-21; and (b) a $V_L$ comprising an amino acid sequence selected from the group consisting of SEQ ID NOs: 22-24; wherein the antibody specifically binds human mesothelin.

A preferred combination comprises: (a) a $V_H$ comprising the amino acid sequence of SEQ ID NO: 19; and (b) a $V_L$ comprising the amino acid sequence of SEQ ID NO: 22.

Another preferred combination comprises: (a) a $V_H$ comprising the amino acid sequence of SEQ ID NO: 20; and (b) a $V_L$ comprising the amino acid sequence of SEQ ID NO: 23.

Another preferred combination comprises: (a) a $V_H$ comprising the amino acid sequence of SEQ ID NO: 21; and (b) a $V_L$ comprising the amino acid sequence of SEQ ID NO: 24.

The antibodies of this disclosure can be, for example, of an IgG1 or IgG4 isotype. Alternatively, they can be antibody fragments, such as Fab, Fab' or Fab'2 fragments, or single chain antibodies.

This disclosure also provides an immunoconjugate comprising an antibody of this disclosure, or antigen-binding portion thereof, linked to a partner molecule. In a particularly preferred embodiment, the invention provides an immunoconjugate comprising an antibody of this disclosure, or antigen-binding portion thereof, linked to the compound Cytotoxin A, which is identified hereinbelow and is discussed in WO 2008/083312, the disclosure of which is incorporated herein by reference. The invention provides the following preferred immunoconjugates, comprising Cytotoxin A linked to an antibody of this invention, wherein the antibody (i) cross-competes with Reference Antibody (a), (b), or (c) for binding to an epitope of human mesothelin; (ii) is according to Embodiment A; (iii) is according to Embodiment B; or (iv) is according to Embodiment C. Certain of such antibody-partner molecule conjugates are capable of being internalized into mesothelin-expressing cells and are capable of mediating ADCC.

In one aspect, such antibody-partner molecule conjugates are conjugated via chemical linkers. In some embodiments, the linker is a peptidyl linker, and is depicted herein as $(L^4)_p$-F-$(L^1)_m$. Other linkers include hydrazine and disulfide linkers, and is depicted herein as $(L^4)_p$-H-$(L^1)_m$ or $(L^4)_p$-J-$(L^1)_m$, respectively. In addition to the linkers as being attached to the partner, the present invention also provides cleavable linker arms that are appropriate for attachment to essentially any molecular species.

This disclosure also provides a bispecific molecule comprising an antibody, or antigen-binding portion thereof, of this disclosure, linked to a second functional moiety having a different binding specificity than said antibody, or antigen binding portion thereof.

Compositions comprising an antibody, or antigen-binding portion thereof, or immunoconjugate or bispecific molecule of this disclosure and a pharmaceutically acceptable carrier are also provided.

Nucleic acid molecules encoding the antibodies, or antigen-binding portions thereof, of this disclosure are also encompassed by this disclosure, as well as expression vectors comprising such nucleic acids and host cells comprising such expression vectors. Methods for preparing anti-mesothelin antibodies using the host cells comprising such expression vectors are also provided and may include the steps of (i) expressing the antibody in the host cell and (ii) isolating the antibody from the host cell.

In yet another aspect, the invention pertains to a method for preparing an anti-mesothelin antibody. The method comprises:

(a) providing: (i) a $V_H$ antibody sequence comprising a CDR1 sequence selected from the group consisting of SEQ ID NOs: 1-3, a CDR2 sequence selected from the group consisting of SEQ ID NOs: 4-6, and/or a CDR3 sequence selected from the group consisting of SEQ ID NOs: 7-9; and/or (ii) a $V_L$ antibody sequence comprising a CDR1 sequence selected from the group consisting of SEQ ID NOs: 10-12, a CDR2 sequence selected from the group consisting of SEQ ID NOs: 13-15, and/or a CDR3 sequence selected from the group consisting of SEQ ID NOs: 16-18;

(b) altering at least one amino acid residue within the $V_H$ antibody sequence and/or the $V_L$ antibody sequence to create at least one altered antibody sequence; and (c) expressing the altered antibody sequence as a protein.

In another aspect, the invention pertains to a method of inhibiting growth of a mesothelin-expressing tumor cell, comprising contacting the tumor cell with an antibody-partner molecule conjugate of the disclosure, such that growth of the tumor cell is inhibited. Preferably, the mesothelin-expressing tumor cell is a mesothelioma cell, pancreatic tumor cell, ovarian tumor cell, stomach tumor cell, lung tumor cell or endometrial tumor cell. In still other embodiments, the mesothelin-expressing tumor cell is from a cancer selected from the group consisting of mesothelioma, papillary serous ovarian adenocarcinoma, clear cell ovarian carcinoma, mixed Mullerian ovarian carcinoma, endometroid mucinous ovarian carcinoma, pancreatic adenocarcinoma, ductal pancreatic adenocarcinoma, uterine serous carcinoma, lung adenocarcinoma, extrahepatic bile duct carcinoma, gastric adenocarcinoma, esophageal adenocarcinoma, colorectal adenocarcinoma and breast adenocarcinoma.

In another aspect, the invention pertains to a method of treating cancer in a subject. The method comprises administering to the subject an antibody-partner molecule conjugate of the disclosure such that the cancer is treated in the subject. Particularly preferred cancers for treatment are mesotheliomas, pancreatic cancers, ovarian cancers, stomach cancers, lung cancers and endometrial cancers. In still other embodiments, the cancer to be treated is selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

BRIEF DESCRIPTION OF THE DRAWINGS

FIG. 1A shows the nucleotide (SEQ ID NO: 25) and amino acid sequences (SEQ ID NO: 19) of the $V_H$ of the 3C10 human monoclonal antibody. The CDR1 (SEQ ID NO: 1), CDR2 (SEQ ID NO: 4) and CDR3 (SEQ ID NO: 7) regions are delineated.

FIG. 1B shows the nucleotide (SEQ ID NO: 28) and amino acid sequences (SEQ ID NO: 22) of the $V_L$ of the 3C10 human monoclonal antibody. The CDR1 (SEQ ID NO: 10), CDR2 (SEQ ID NO: 13) and CDR3 (SEQ ID NO: 16) regions are delineated.

FIG. 2A shows the nucleotide (SEQ ID NO: 26) and amino acid sequences (SEQ ID NO: 20) of the $V_H$ of the 6A4 human monoclonal antibody. The CDR1 (SEQ ID NO: 2), CDR2 (SEQ ID NO: 5) and CDR3 (SEQ ID NO: 8) regions are delineated.

FIG. 2B shows the nucleotide (SEQ ID NO: 29) and amino acid sequences (SEQ ID NO: 23) of the $V_L$ of the 6A4 human monoclonal antibody. The CDR1 (SEQ ID NO: 11), CDR2 (SEQ ID NO: 14) and CDR3 (SEQ ID NO: 17) regions are delineated.

FIG. 3A shows the nucleotide (SEQ ID NO: 27) and amino acid sequences (SEQ ID NO: 21) of the $V_H$ of the 7B1 human monoclonal antibody. The CDR1 (SEQ ID NO: 3), CDR2 (SEQ ID NO: 6) and CDR3 (SEQ ID NO: 9) regions are delineated.

FIG. 3B shows the nucleotide (SEQ ID NO: 30) and amino acid sequences (SEQ ID NO: 24) of the $V_L$ of the 7B1 human monoclonal antibody. The CDR1 (SEQ ID NO: 12), CDR2 (SEQ ID NO: 15) and CDR3 (SEQ ID NO: 18) regions are delineated.

FIG. 4 shows the alignment of the amino acid sequence of the $V_H$s of 3C10 (SEQ ID NO: 19) and 6A4 (SEQ ID NO: 20) with the human germline $V_H$ 3-33 amino acid sequence (SEQ ID NO: 31).

FIG. 5 shows the alignment of the amino acid sequence of the $V_L$s of 3C10 (SEQ ID NO: 22) and 6A4 (SEQ ID NO: 23) with the human germline $V_k$ L6 amino acid sequence (SEQ ID NO: 33).

FIG. 6 shows the alignment of the amino acid sequence of the $V_H$ of 7B1 (SEQ ID NO: 21) with the human germline $V_H$ 3-7 amino acid sequence (SEQ ID NO: 32).

FIG. 7 shows the alignment of the amino acid sequence of the $V_L$ of 7B1 (SEQ ID NO: 24) with the human germline $V_k$ A27 amino acid sequence (SEQ ID NO: 34).

DETAILED DESCRIPTION OF THIS DISCLOSURE

Figure 8:
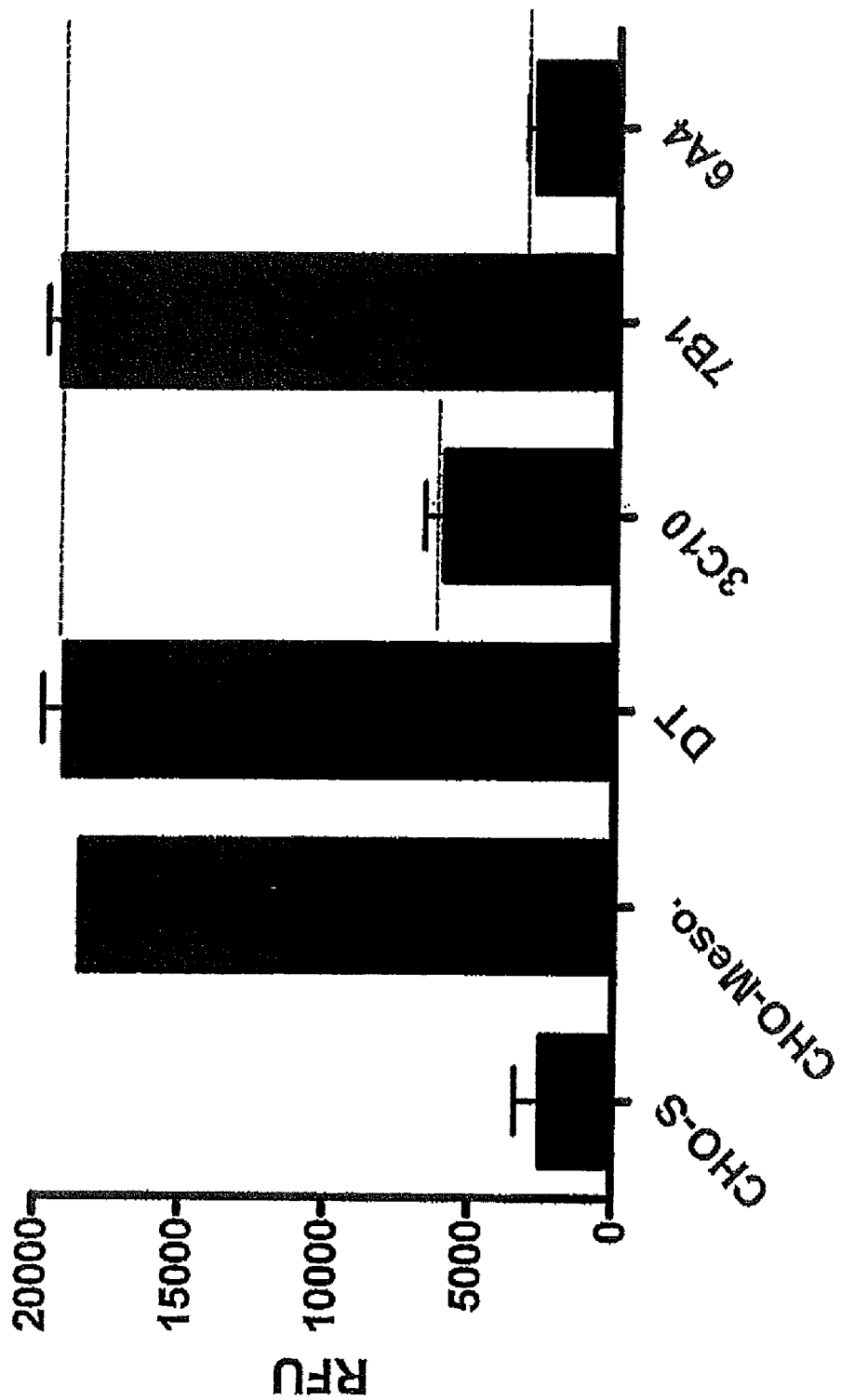
FIG. 8 shows the results of an OVCAR3 ovarian cancer cell adhesion assay.

The present disclosure relates to isolated monoclonal antibodies, particularly human ones, which bind to human mesothelin and have desirable properties. In certain embodiments, the antibodies of this disclosure are derived from particular heavy and light chain germline sequences and/or comprise particular structural features such as CDR regions comprising particular amino acid sequences. This disclosure provides isolated antibodies, methods of making such antibodies, antibody-partner molecule conjugates, and bispecific molecules comprising such antibodies and pharmaceutical compositions containing such antibodies, antibody-partner molecule conjugates or bispecific molecules. Also provided are variants or alternatives such as homologous antibodies, antibodies with conservative modifications, engineered and modified antibodies, antibody fragments, and antibody mimetics, each further described hereinbelow. This disclosure also relates to methods of using the antibodies, such as to detect mesothelin protein, as well as to methods of using the anti-mesothelin antibodies of the invention to inhibit the growth of mesothelin-expressing cells, such as tumor cells. Accordingly, this disclosure also provides methods of using the anti-mesothelin antibodies of this disclosure to treat various types of cancer, for example, ovarian cancer, pancreatic cancer, stomach cancer, lung cancer, endometrial cancer and mesotheliomas. Preferably, the antibody, conjugate, bispecific molecule, alternative or variant one or more of these properties: binding to human mesothelin, internalization by mesothelin expressing cells, inhibition of mesothelin binding to CA125, mediation of ADCC against mesothelin expressing cells, and inhibition of growth of mesothelin-expressing tumor cells in vivo. Antibodies can be human (preferably), humanized, or chimeric.

In order that the present disclosure may be more readily understood, certain terms are first defined. Additional definitions are set forth throughout the detailed description.

The term "mesothelin" includes variants, isoforms, homologs, orthologs and paralogs. For example, antibodies specific for a human mesothelin protein may, in certain cases, cross-react with a mesothelin protein from a species other than human. In other embodiments, the antibodies can be completely specific for the human mesothelin protein and not exhibit species or other types of cross-reactivity, or cross-react with mesothelin from certain other species but not all other species (e.g., cross-react with a primate mesothelin but not mouse mesothelin). The term "human mesothelin" refers to human sequence mesothelin, such as the complete amino acid sequence of human mesothelin having Genbank Accession Number NP_005814. The term "mouse mesothelin" refers to mouse sequence mesothelin, such as the complete amino acid sequence of mouse mesothelin having Genbank Accession Number NP_061345. The N-terminal portion of mesothelin is also known as megakaryocyte potentiating factor (MPF). The human mesothelin sequence may differ from human mesothelin of Genbank Accession Number NP_005814 by having, for example, conserved mutations or mutations in non-conserved regions and the mesothelin has substantially the same biological function as the human mesothelin of Genbank Accession Number NP_005814, such as binding to CA125.

A particular human mesothelin sequence will generally be at least 90% identical in amino acids sequence to human mesothelin of Genbank Accession Number NP_005814 and contains amino acid residues that identify the amino acid sequence as being human when compared to mesothelin amino acid sequences of other species (e.g., murine). In certain cases, a human mesothelin may be at least 95%, or even at least 96%, 97%, 98%, or 99% identical in amino acid sequence to mesothelin of Genbank Accession Number NP_005814. In certain embodiments, a human mesothelin sequence will display no more than 10 amino acid differences from the mesothelin sequence of Genbank Accession Number NP_005814. In certain embodiments, the human mesothelin may display no more than 5, or even no more than 4, 3, 2, or 1 amino acid difference from the mesothelin sequence of Genbank Accession Number NP_005814. Percent identity can be determined as described herein.

The term "CA125" refers to an ovarian carcinoma antigen, or ovarian cancer tumor marker, also known as MUC-16. The term "human CA125" refers to human sequence CA125 such as the complete amino acid sequence of human CA125 having Genbank Accession Number NP_078966. The human CA125 sequence may differ from human CA125 of Genbank Accession Number NP_078966 by having, for example, conserved mutations or mutations in non-conserved regions. A particular human CA125 sequence will generally be at least 90% identical in amino acids sequence to human CA125 of Genbank Accession Number NP_078966 and contains amino acid residues that identify the amino acid sequence as being human when compared to CA125 amino acid sequences of other species (e.g., murine). In certain cases, a human CA125 may be at least 95%, or even at least 96%, 97%, 98%, or 99% identical in amino acid sequence to CA125 of Genbank Accession Number NP_078966. In certain embodiments, a human CA125 sequence will display no more than 10 amino acid differences from the CA125 sequence of Genbank Accession Number NP_078966. In certain embodiments, the human CA125 may display no more than 5, or even no more than 4, 3, 2, or 1 amino acid difference from the CA125 sequence of Genbank Accession Number NP_078966. Percent identity can be determined as described herein.

The term "immune response" refers to the action of for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human mesothelin.

The term "antibody" refers to whole antibodies and any antigen binding fragment ("antigen-binding portion") or single chains thereof. An "antibody" refers to a glycoprotein comprising at least two heavy (H) chains and two light (L) chains inter-connected by disulfide bonds, or an antigen binding portion thereof. Each heavy chain comprises a heavy chain variable region (abbreviated herein as $V_H$) and a heavy chain constant region. The heavy chain constant region is comprised of three domains, $C_H1$, $C_H2$ and $C_H3$. Each light chain comprises a light chain variable region (abbreviated herein as $V_L$) and a light chain constant region. The light chain constant region is comprised of one domain, $C_L$. $V_H$ and $V_L$ can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antibody fragment" and "antigen-binding portion" of an antibody (or simply "antibody portion"), as used herein, refer to one or more fragments of an antibody that retain the ability to specifically bind to an antigen (e.g., mesothelin). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3$^{rd}$ ed. 1993); (iv) a Fd fragment consisting of the $V_H$ and $C_H1$ domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as intact antibodies.

An "isolated antibody" refers to an antibody that is substantially free of other antibodies having different antigenic specificities (e.g., an isolated antibody that specifically binds mesothelin is substantially free of antibodies that specifically bind other antigens). An isolated antibody that specifically binds mesothelin may, however, have cross-reactivity to other antigens, such as mesothelin molecules from other species. Moreover, an isolated antibody may be substantially free of other cellular material and/or chemicals.

The terms "monoclonal antibody" or "monoclonal antibody composition" refer to a preparation of antibody molecules of single molecular composition. A monoclonal antibody composition displays a single binding specificity and affinity for a particular epitope.

The term "human antibody" refers to antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, "human antibody" is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgM or IgG1) that is encoded by the heavy chain constant region genes.

The phrases "an antibody recognizing an antigen" and "an antibody specific for an antigen" are used interchangeably with "an antibody which binds specifically to an antigen."

The term "human antibody derivatives" refers to any modified form of the human antibody, e.g., a conjugate of the antibody and another agent or antibody.

The term "humanized antibody" refers to antibodies in which CDR sequences derived from the germline of another mammalian species, such as a mouse, have been grafted onto human framework sequences. Additional framework region modifications may be made within the human framework sequences.

The term "chimeric antibody" refers to antibodies in which the variable region sequences are derived from one species and the constant region sequences are derived from another species, such as an antibody in which the variable region sequences are derived from a mouse antibody and the constant region sequences are derived from a human antibody.

The term "antibody mimetic" refers to molecules capable of mimicking an antibody's ability to bind an antigen, but which are not limited to native antibody structures. Examples of such antibody mimetics include, but are not limited to, Affibodies, DARPins, Anticalins, Avimers, and Versabodies, all of which are further described hereibelow.

The term "partner molecule" refers to the entity which is conjugated to an antibody in an antibody-partner molecule conjugate. Examples of partner molecules include drugs, toxins, marker molecules, proteins and therapeutic agents.

As used herein, an antibody that "specifically binds to human mesothelin" is intended to refer to an antibody that binds to human mesothelin with a $K_D$ of $1\times10^{-7}$ M or less, more preferably $5\times10^{-8}$ M or less, more preferably $3\times10^{-8}$ M or less, more preferably $1\times10^{-8}$ M or less, even more preferably $5\times10^{-9}$ M or less.

The term "does not substantially bind" to a protein or cells, as used herein, means does not bind or does not bind with a high affinity to the protein or cells, i.e. binds to the protein or cells with a $K_D$ of $1\times10^{-6}$ M or more, more preferably $1\times10^{-5}$ M or more, more preferably $1\times10^{-4}$ M or more, more preferably $1\times10^{-3}$ M or more, even more preferably $1\times10^{-2}$ M or more.

The term "$K_{assoc}$" or "$K_a$" refers to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, refers to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

The term "high affinity" for an IgG antibody refers to an antibody having a $K_D$ of $1 \times 10^{-7}$ M or less, more preferably $5 \times 10^{-8}$ M or less, even more preferably $1 \times 10^{-8}$ M or less, even more preferably $5 \times 10^{-9}$ M or less and even more preferably $1 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups, which are limited to hydrocarbon groups are termed "homoalkyl".

The term "alkylene" by itself or as part of another substituent means a divalent radical derived from an alkane, as exemplified, but not limited, by —$CH_2CH_2CH_2CH_2$—, and further includes those groups described below as "heteroalkylene." Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from O, N, Si, and S, and wherein the nitrogen, carbon and sulfur atoms may optionally be oxidized and the nitrogen heteroatom may optionally be quaternized. The heteroatom(s) O, N, S, and Si may be placed at any interior position of the heteroalkyl group or at the position at which the alkyl group is attached to the remainder of the molecule. Examples include, but are not limited to, —$CH_2CH_2OCH_3$, —$CH_2CH_2NHCH_3$, —$CH_2CH_2N(CH_3)_2$, —$CH_2SCH_2CH_3$, —$CH_2CH_2S(O)CH_3$, —$CH_2CH_2S(O)_2CH_3$, —$CH=CHOCH_3$, —$Si(CH_3)_3$, —$CH_2CH=NOCH_3$, and —$CH=CHN(CH_3)_2$. Up to two heteroatoms may be consecutive, such as, for example, —$CH_2NHOCH_3$ and —$CH_2OSi(CH_3)_3$. Similarly, the term "heteroalkylene" by itself or as part of another substituent means a divalent radical derived from heteroalkyl, as exemplified, but not limited by, —$CH_2CH_2SCH_2CH_2$— and —$CH_2SCH_2CH_2NHCH_2$—. For heteroalkylene groups, heteroatoms can also occupy either or both of the chain termini (e.g., alkyleneoxy, alkylenedioxy, alkyleneamino, alkylenediamino, and the like). The terms "heteroalkyl" and "heteroalkylene" encompass poly(ethylene glycol) and its derivatives (see, for example, Shearwater Polymers Catalog, 2001). Still further, for alkylene and heteroalkylene linking groups, no orientation of the linking group is implied by the direction in which the formula of the linking group is written. For example, the formula —$C(O)_2R'$— represents both —$C(O)_2R'$— and —$R'C(O)_2$—.

The term "lower" in combination with the terms "alkyl" or "heteroalkyl" refers to a moiety having from 1 to 6 carbon atoms.

The terms "alkoxy," "alkylamino," "alkylsulfonyl," and "alkylthio" (or thioalkoxy) are used in their conventional sense, and refer to those alkyl groups attached to the remainder of the molecule via an oxygen atom, an amino group, an $SO_2$ group or a sulfur atom, respectively. The term "arylsulfonyl" refers to an aryl group attached to the remainder of the molecule via an $SO_2$ group, and the term "sulfhydryl" refers to an SH group.

In general, an "acyl substituent" is also selected from the group set forth above. As used herein, the term "acyl substituent" refers to groups attached to, and fulfilling the valence of a carbonyl carbon that is either directly or indirectly attached to the polycyclic nucleus of the compounds of the present invention.

The terms "cycloalkyl" and "heterocycloalkyl", by themselves or in combination with other terms, represent, unless otherwise stated, cyclic versions of substituted or unsubstituted "alkyl" and substituted or unsubstituted "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The heteroatoms and carbon atoms of the cyclic structures are optionally oxidized.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" includes, but is not limited to, trifluoromethyl, 2,2,2-trifluoroethyl, 4-chlorobutyl, 3-bromopropyl, and the like.

The term "aryl" means, unless otherwise stated, a substituted or unsubstituted polyunsaturated, aromatic, hydrocarbon substituent which can be a single ring or multiple rings (preferably from 1 to 3 rings) which are fused together or linked covalently. The term "heteroaryl" refers to aryl groups (or rings) that contain from one to four heteroatoms selected from N, O, and S, wherein the nitrogen, carbon and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. "Aryl" and "heteroaryl" also encompass ring systems in which one or more non-aromatic ring systems are fused, or otherwise bound, to an aryl or heteroaryl system.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Preferred substituents for each type of radical are provided below.

Substituents for the alkyl, and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generally referred to as "alkyl substituents" and "heteroalkyl substituents," respectively, and they can be one or more of a variety of groups selected from, but not limited to: —OR', =O, =NR', =NOR', —NR'R", —SR', -halogen, —SiR'R"R'", —OC(=O)R', —C(=O)R', —CO$_2$R', —CONR'R", —OC(=O)NR'R", —NR"C(=O)R', —NR'C(=O)NR"R'", —NR"C(=O)$_2$R', —NRC(NR'R"R'")=NR"", —NRC(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5, 6, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(=O)CH$_3$, —C(=O)CF$_3$, —C(=O)CH$_2$OCH$_3$, and the like).

Similar to the substituents described for the alkyl radical, the aryl substituents and heteroaryl substituents are generally referred to as "aryl substituents" and "heteroaryl substituents," respectively and are varied and selected from, for example: halogen, —OR', =O, =NR', =NR—OR', —NR'R", —SR', -halogen, —SiR'R"R'", —OC(=O)R', —C(=O)R', —CO$_2$R', —C(=O)NR'R", —OC(=O)NR'R", —NR"C(=O)R', —NR'C(=O)NR"R'", —NR"CO$_2$R', —NRC(NR'R")=NR'", —S(=O)R', —S(=O)$_2$R', —S(=O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R'" and R"" groups when more than one of these groups is present.

Two of the aryl substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$X(CR"R'")$_d$—, where s and d are independently integers of from 0 to 3, and X is —O—, —NR'—, —S—, —S(=O)—, —S(=O)$_2$—, or —S(=O)$_2$NR'—. The substituents R, R', R" and R'" are preferably independently selected from hydrogen or substituted or unsubstituted (C$_1$-C$_6$) alkyl.

As used herein, the term "diphosphate" includes but is not limited to an ester of phosphoric acid containing two phosphate groups. The term "triphosphate" includes but is not limited to an ester of phosphoric acid containing three phosphate groups.

As used herein, the term "heteroatom" includes oxygen (O), nitrogen (N), sulfur (S) and silicon (Si).

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, and substituted or unsubstituted heterocyclyl groups, unless the context indicates otherwise.

Various aspects of the invention are described in further detail in the following subsections.

Anti-Mesothelin Antibodies Having Particular Functional Properties

The antibodies of this disclosure are characterized by particular functional features or properties. For example, they specifically bind to human mesothelin, such as human mesothelin expressed on the cell surface. Preferably, an antibody of this disclosure binds to human mesothelin with high affinity, for example with a K$_D$ of 1×10$^{-7}$M or less, more preferably with a K$_D$ of 5×10$^{-8}$ M or less and even more preferably with a K$_D$ of 1×10$^{-8}$ M or less. An anti-mesothelin antibody of this disclosure binds to human mesothelin and preferably exhibits one or more of the following properties:
(a) binds to human mesothelin with a K$_D$ of 1×10$^{-8}$ M or less;
(b) is internalized by mesothelin-expressing cells;
(c) inhibits binding of mesothelin to ovarian cancer antigen CA125;
(d) exhibits antibody dependent cellular cytotoxicity (ADCC) against mesothelin-expressing cells; and (e) inhibits growth of mesothelin-expressing cells in vivo when conjugated to a cytotoxin.

Preferably, an antibody of this disclosure binds to a mesothelin protein with a $K_D$ of $5\times10^{-8}$ M or less, binds to a mesothelin protein with a $K_D$ of $3\times10^{-8}$ M or less, binds to a mesothelin protein with a $K_D$ of $1\times10^{-8}$ M or less, binds to a mesothelin protein with a $K_D$ of $7\times10^{-9}$ M or less, binds to a mesothelin protein with a $K_D$ of $6\times10^{-9}$ M or less or binds to a mesothelin protein with a $K_D$ of $5\times10^{-9}$ M or less. The binding affinity of the antibody for mesothelin can be evaluated, for example, by standard BIACORE analysis. (see e.g., Example 3B).

Preferred antibodies of the invention are human monoclonal antibodies. Additionally or alternatively, the antibodies can be, for example, chimeric or humanized monoclonal antibodies.

Monoclonal Antibodies 3C10, 6A4 and 7B1

Preferred antibodies of this disclosure are the human monoclonal antibodies 3C10, 6A4 and 7B1, isolated and structurally characterized as described in Examples 1 and 2. The $V_H$ amino acid sequences of 3C10, 6A4 and 7B1 are shown in SEQ ID NOs: 19, 20 and 21, respectively. The $V_L$ amino acid sequences of 3C10, 6A4 and 7B1 are shown in SEQ ID NOs: 22, 23 and 24, respectively.

In another aspect, this disclosure provides antibodies that comprise the heavy chain and light chain CDR1s, CDR2s and CDR3s of 3C10, 6A4 or 7B1, or combinations thereof. The amino acid sequences of the $V_H$ CDR1s of 3C10, 6A4 and 7B1 are shown in SEQ ID NOs: 1-3, respectively. The amino acid sequences of the $V_H$ CDR2s of 3C10, 6A4 and 7B1 are shown in SEQ ID NOs: 4-6, respectively. The amino acid sequences of the $V_H$ CDR3s of 3C10, 6A4 and 7B1 are shown in SEQ ID NOs: 7-9, respectively. The amino acid sequences of the $V_L$ CDR1s of 3C10, 6A4 and 7B1 are shown in SEQ ID NOs: 10-12, respectively. The amino acid sequences of the $V_L$ CDR2s of 3C10, 6A4 and 7B1 are shown in SEQ ID NOs: 13-15. The amino acid sequences of the $V_L$ CDR3s of 3C10, 6A4 and 7B1 are shown in SEQ ID NOs: 16-18, respectively. The CDR regions are delineated using the Kabat system (Kabat, E. A., et al. (1991) Sequences of Proteins of Immunological Interest, Fifth Edition, US Department of Health and Human Services, NIH Publication No. 91-3242, hereinafter "Kabat '242").

Given that each of these antibodies can bind to human mesothelin and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other anti-mesothelin binding molecules of this disclosure. Preferably, when $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies 3C10, 6A4 and 7B1.

Accordingly, in another aspect, this disclosure provides an isolated monoclonal antibody, or antigen binding portion thereof comprising:

(a) a heavy chain variable region CDR1 comprising an amino acid sequence selected from the group consisting of SEQ ID NOs: 1-3;

(b) a heavy chain variable region CDR2 comprising an amino acid sequence selected from the group consisting of SEQ ID NOs: 4-6;

(c) a heavy chain variable region CDR3 comprising an amino acid sequence selected from the group consisting of SEQ ID NOs: 7-9;

(d) a light chain variable region CDR1 comprising an amino acid sequence selected from the group consisting of SEQ ID NOs: 10-12;

(e) a light chain variable region CDR2 comprising an amino acid sequence selected from the group consisting of SEQ ID NOs: 13-15; and (f) a light chain variable region CDR3 comprising an amino acid sequence selected from the group consisting of SEQ ID NOs: 16-18;

wherein the antibody specifically binds human mesothelin.

In one preferred embodiment, the antibody is according to Embodiment A. In another preferred embodiment, the antibody is according to Embodiment B. In yet another preferred embodiment, the antibody is according to Embodiment C.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence.

Accordingly, the present disclosure provides monoclonal antibodies comprising one or more heavy and/or light chain CDR3 domains from an antibody derived from a human or non-human animal, wherein the monoclonal antibody is capable of specifically binding to human mesothelin. Within certain aspects, the present disclosure provides monoclonal antibodies comprising one or more heavy and/or light chain CDR3 domain from a non-human antibody, such as a mouse or rat antibody, wherein the monoclonal antibody is capable of specifically binding to mesothelin. Within some embodiments, such inventive antibodies comprising one or more heavy and/or light chain CDR3 domain from a non-human antibody (a) are capable of competing for binding with; (b) retain the functional characteristics of; (c) bind to the same epitope as; and/or (d) have a similar binding affinity as the corresponding parental non-human antibody.

Within other aspects, the present disclosure provides monoclonal antibodies comprising one or more heavy and/or light chain CDR3 domain from a human antibody, such as, for example, a human antibody obtained from a non-human animal, wherein the human antibody is capable of specifically binding to human mesothelin. Within other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to human mesothelin and wherein the CDR3 domain from the first human antibody replaces a CDR3 domain in a human antibody that is lacking binding specificity for mesothelin to generate a second human antibody that is capable of specifically binding to human mesothelin. Within some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental first human antibody.

Antibodies Having Particular Germline Sequences

In certain embodiments, an antibody of this disclosure comprises a $V_H$ from a particular germline heavy chain immunoglobulin gene and/or a $V_L$ from a particular germline light chain immunoglobulin gene.

For example, in a preferred embodiment, this disclosure provides an isolated monoclonal antibody, or an antigen-binding portion thereof, comprising a $V_H$ that is the product of or derived from a human $V_H$ 3-33 gene or a human $V_H$ 3-7 gene, wherein the antibody specifically binds human mesothelin. In another preferred embodiment, this disclosure provides an isolated monoclonal antibody, or an antigen-binding portion thereof, comprising a $V_L$ that is the product of or derived from a human $V_K$ L6 gene or a human $V_K$ A27 gene, wherein the antibody specifically binds human mesothelin. In yet another preferred embodiment, this disclosure provides an isolated monoclonal antibody, or antigen-binding portion thereof, wherein the antibody comprises a $V_H$ that is the product of or derived from a human $V_H$ 3-33 gene and comprises a $V_L$ that is the product of or derived from a human $V_K$ L6 gene, wherein the antibody specifically binds human mesothelin. In yet another preferred embodiment, this disclosure provides an isolated monoclonal antibody, or antigen-binding portion thereof, wherein the antibody comprises a $V_H$ that is the product of or derived from a human $V_H$ 3-7 gene and comprises a $V_L$ that is the product of or derived from a human $V_K$ A27 gene, wherein the antibody specifically binds human mesothelin.

Such antibodies also may possess one or more of the functional characteristics described in detail above, such as high affinity binding to human mesothelin, internalization by mesothelin-expressing cells, inhibition of binding of mesothelin to CA125, the ability to mediate ADCC against mesothelin-expressing cells and/or the ability to inhibit tumor growth of mesothelin-expressing tumor cells in vivo when conjugated to a cytotoxin.

Examples of antibodies having $V_H$ and $V_L$ of $V_H$ 3-33 and $V_K$ L6, respectively, are the 3C10 and 6A4 antibodies. An example of an antibody having $V_H$ and $V_L$ of $V_H$ 3-7 and $V_K$ A27, respectively, is the 7B1 antibody.

As used herein, a human antibody comprises heavy or light chain variable regions that is "the product of" or "derived from" a particular germline sequence if the variable regions of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally-occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of this disclosure comprises heavy and light chain variable regions comprising amino acid sequences that are homologous to the amino acid sequences of the preferred antibodies described herein, and wherein the antibodies retain the desired functional properties of the anti-mesothelin antibodies of this disclosure.

For example, this disclosure provides an isolated monoclonal antibody, or antigen binding portion thereof, comprising a $V_H$ and a $V_L$, wherein: (a) the $V_H$ comprises an amino acid sequence that is at least 80% homologous to an amino acid sequence selected from the group consisting of SEQ ID NOs: 19-21; (b) the $V_L$ comprises an amino acid sequence that is at least 80% homologous to an amino acid sequence selected from the group consisting of SEQ ID NOs: 22-24; and (c) the antibody specifically binds to human mesothelin.

In other embodiments, the $V_H$ and/or $V_L$ amino acid sequences may be 85%, 90%, 95%, 96%, 97%, 98% or 99% homologous to the sequences set forth above. An antibody having $V_H$ and $V_L$ regions having high (i.e., 80% or greater) homology to the $V_H$ and $V_L$ regions of the sequences set forth above, can be obtained by mutagenesis (e.g., site-directed or PCR-mediated mutagenesis) of nucleic acid molecules encoding SEQ ID NOs: 25-27 or 28-30, followed by testing of the encoded altered antibody for retained function (i.e., the functions set forth above) using the functional assays described herein.

The percent homology between two amino acid sequences is equivalent to the percent identity between the two sequences. The percent identity between the two sequences is a function of the number of identical positions shared by the sequences (i.e.,% homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (*Comput. Appl. Biosci.*, 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The protein sequences of the present disclosure also can be used as a "query sequence" to search against public databases to, for example, to identify related sequences. Such searches can be performed using the XBLAST program (version 2.0) of Altschul, et al. (1990) J. Mol. Biol. 215:403-10. BLAST protein searches can be performed with the XBLAST program, score=50, wordlength=3 to obtain amino acid sequences homologous to the antibody molecules of this disclosure. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) are useful.

Antibodies with Conservative Modifications

In certain embodiments, an antibody of this disclosure comprises a $V_H$ comprising CDR1, CDR2 and CDR3 sequences and a $V_L$ comprising CDR1, CDR2 and CDR3 sequences, wherein one or more of these CDR sequences comprise specified amino acid sequences based on known anti-mesothelin antibodies, or conservative modifications thereof, and wherein the antibodies retain the desired functional properties of the anti-mesothelin antibodies of this disclosure. It is understood in the art that certain conservative sequence modification can be made which do not remove antigen binding. Accordingly, this disclosure provides an isolated monoclonal antibody, or antigen binding portion thereof, comprising a $V_H$ comprising CDR1, CDR2, and CDR3 sequences and a $V_L$ comprising CDR1, CDR2, and CDR3 sequences, wherein: (a) the $V_H$ CDR3 sequence comprises an amino acid sequence selected from the group consisting of amino acid sequences of SEQ ID NOs: 7-9, and conservative modifications thereof; (b) the $V_L$ CDR3 sequence comprises an amino acid sequence selected from the group consisting of amino acid sequence of SEQ ID NOs: 16-18, and conservative modifications thereof; and (c) the antibody specifically binds human mesothelin.

In a preferred embodiment, the heavy chain variable region CDR2 sequence comprises an amino acid sequence selected from the group consisting of amino acid sequences of SEQ ID NOs: 4-6, and conservative modifications thereof; and the light chain variable region CDR2 sequence comprises an amino acid sequence selected from the group consisting of amino acid sequences of SEQ ID NOs: 13-15, and conservative modifications thereof. In another preferred embodiment, the heavy chain variable region CDR1 sequence comprises an amino acid sequence selected from the group consisting of amino acid sequences of SEQ ID NOs: 1-3, and conservative modifications thereof; and the light chain variable region CDR1 sequence comprises an amino acid sequence selected from the group consisting of amino acid sequences of SEQ ID NOs: 10-12, and conservative modifications thereof.

The term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of this disclosure can be replaced with other amino acid residues from the same side chain family and the altered antibody can be tested for retained function using the functional assays described herein.

Antibodies that Bind to the Same Epitope as Anti-Mesothelin Antibodies

In another embodiment, this disclosure provides antibodies that bind an epitope on mesothelin recognized by any of the anti-mesothelin monoclonal antibodies of this disclosure (i.e., antibodies that have the ability to cross-compete for binding to human mesothelin with any of the monoclonal antibodies of this disclosure). In preferred embodiments, the reference antibody for cross-competition studies can be the monoclonal antibody 3C10 (having $V_H$ and $V_L$ sequences as shown in SEQ ID NOs: 19 and 22, respectively), or the monoclonal antibody 6A4 (having $V_H$ and $V_L$ sequences as shown in SEQ ID NOs: 20 and 23, respectively), or the monoclonal antibody 7B1 (having $V_H$ and $V_L$ sequences as shown in SEQ ID NOs: 21 and 24, respectively).

Such cross-competing antibodies can be identified based on their ability to cross-compete with 3C10, 6A4 or 7B1 in standard mesothelin binding assays, such as ELISA or BIAcore analysis. In a preferred embodiment, the antibody that binds to the same epitope on human mesothelin as is recognized by 3C10, 6A4 or 7B1 is a human monoclonal antibody. Such human monoclonal antibodies can be prepared and isolated as described in the Examples.

Engineered and Modified Antibodies

An antibody of the invention further can be prepared using an antibody having one or more known anti-mesothelin antibody $V_H$ and/or $V_L$ sequences as starting material to engineer a modified antibody having altered properties as compared to the starting antibody. One or more amino acids within one or both of $V_H$ and $V_L$, within one or more CDR regions and/or within one or more framework regions can be modified. Additionally or alternatively, residues within the constant region(s) can be modified to alter the effector function(s) of the antibody.

In certain embodiments, CDR grafting can be used to engineer variable regions of antibodies. Antibodies interact with target antigens predominantly through amino acid residues in their CDRs. For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. USA.* 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of this disclosure pertains to an isolated monoclonal antibody, or antigen binding portion thereof, comprising a $V_H$ comprising CDR1, CDR2, and CDR3 sequences comprising an amino acid sequence selected from the group consisting of SEQ ID NOs: 1-3, SEQ ID NOs: 4-6, and SEQ ID NOs: 7-9, respectively, and a $V_L$ comprising CDR1, CDR2, and CDR3 sequences comprising an amino acid sequence selected from the group consisting of SEQ ID NOs: 10-12, SEQ ID NOs: 13-15, and SEQ ID NOs: 16-18, respectively. Thus, such antibodies contain the $V_H$ and V_L CDR sequences of monoclonal antibodies 3C10, 6A4 or 7B1 yet may contain different framework sequences from these antibodies.

Such framework sequences can be obtained from public DNA databases or published references that include germline antibody gene sequences. For example, germline DNA sequences for human $V_H$ and $V_L$ genes can be found in the "VBase" human germline sequence database, as well as in Kabat '242; Tomlinson, I. M., et al. (1992) *J. Mol. Biol.* 227:776-798; and Cox, J. P. L. et al. (1994) *Ear. J. Immunol.* 24:827-836; each of which is incorporated herein by reference. As another example, the germline DNA sequences for human $V_H$ and $V_L$ genes can be found in the Genbank database. For example, the following heavy chain germline sequences found in the HCo7 HuMAb mouse are available in the accompanying Genbank accession numbers: 1-69 (NG_0010109, NT_024637 and BC070333), 3-33 (NG_0010109 and NT_024637) and 3-7 (NG_0010109 and NT_024637). As another example, the following heavy chain germline sequences found in the HCo12 mouse of the HuMAb Mouse type are available in the accompanying Genbank accession numbers: 1-69 (NG_0010109, NT_024637 and BC070333), 5-51 (NG_0010109 and NT_024637), 4-34 (NG_0010109 and NT_024637), 3-30.3 (CAJ556644) and (AJ406678). Yet another source of human heavy and light chain germline sequences is the database of human immunoglobulin genes available from IMGT.

Antibody protein sequences are compared against a compiled protein sequence database using one of the sequence similarity searching methods called the Gapped BLAST (Altschul et al. (1997) *Nucleic Acids Research* 25:3389-3402), which is well known to those skilled in the art. BLAST is a heuristic algorithm in that a statistically significant alignment between the antibody sequence and the database sequence is likely to contain high-scoring segment pairs (HSP) of aligned words. Segment pairs whose scores cannot be improved by extension or trimming is called a hit. Briefly, the nucleotide sequences of VBASE origin are translated and the region between and including FR1 through FR3 framework region is retained. The database sequences have an average length of 98 residues. Duplicate sequences which are exact matches over the entire length of the protein are removed. A BLAST search for proteins using the program blastp with default, standard parameters except the low complexity filter, which is turned off, and the substitution matrix of BLOSUM62, filters for top 5 hits yielding sequence matches. The nucleotide sequences are translated in all six frames and the frame with no stop codons in the matching segment of the database sequence is considered the potential hit. This is in turn confirmed using the BLAST program tblastx, which translates the antibody sequence in all six frames and compares those translations to the VBASE nucleotide sequences dynamically translated in all six frames. Other human germline sequence databases, such as that available from IMGT, can be searched similarly to VBASE as described above.

The identities are exact amino acid matches between the antibody sequence and the protein database over the entire length of the sequence. The positives (identities+substitution match) are not identical but amino acid substitutions guided by the BLOSUM62 substitution matrix. If the antibody sequence matches two of the database sequences with same identity, the hit with most positives would be decided to be the matching sequence hit.

Preferred framework sequences for use in the antibodies of this disclosure are those structurally similar to the framework sequences used by selected antibodies of this disclosure, e.g., similar to the $V_H$ 3-33 (SEQ ID NO: 31) or $V_H$ 3-7 (SEQ ID NO: 32) framework sequences and/or the $V_K$ L6 (SEQ ID NO: 33) or $V_K$ A27 (SEQ ID NO: 34) framework sequences. The $V_H$ CDR1, CDR2, and CDR3 sequences and the $V_K$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability (see e.g., U.S. Pat. Nos. 5,530,101; 5,585,089; 5,693,762 and 6,180,370 to Queen et al.).

Another type of variable region modification is the mutation of amino acid residues within the $V_H$ and/or $V_K$ CDR1, CDR2 and/or CDR3 regions to improve one or more binding properties (e.g., affinity). Site-directed mutagenesis or PCR-mediated mutagenesis can be performed to introduce the mutation(s) and the effect on antibody binding, or other functional property of interest, can be evaluated in in vitro or in vivo assays as described herein. Preferably conservative modifications are introduced. The mutations may be amino acid substitutions, additions or deletions, but are preferably substitutions. Moreover, typically no more than one, two, three, four or five residues within a CDR region are altered.

Accordingly, in another embodiment, the instant disclosure provides isolated anti-mesothelin monoclonal antibodies, or antigen binding portions thereof, comprising: (a) a $V_H$ CDR1 region comprising an amino acid sequence selected from the group consisting of SEQ ID NOs: 1-3, or an amino acid sequence having one, two, three, four or five amino acid substitutions, deletions or additions as compared to SEQ ID NOs: 1-3; (b) a $V_H$ CDR2 region comprising an amino acid sequence selected from the group consisting of SEQ ID NOs: 4-6, or an amino acid sequence having one, two, three, four or five amino acid substitutions, deletions or additions as compared to SEQ ID NOs: 4-6; (c) a $V_H$ CDR3 region comprising an amino acid sequence selected from the group consisting of SEQ ID NOs: 7-9, or an amino acid sequence having one, two, three, four or five amino acid substitutions, deletions or additions as compared to SEQ ID NOs: 7-9; (d) a $V_L$ CDR1 region comprising an amino acid sequence selected from the group consisting of SEQ ID NOs: 10-12, or an amino acid sequence having one, two, three, four or five amino acid substitutions, deletions or additions as compared to SEQ ID NOs: 10-12; (e) a $V_L$ CDR2 region comprising an amino acid sequence selected from the group consisting of SEQ ID NOs: 13-15, or an amino acid sequence having one, two, three, four or five amino acid substitutions, deletions or additions as compared to SEQ ID NOs: 13-15; and (f) a $V_L$ CDR3 region comprising an amino acid sequence selected from the group consisting of SEQ ID NOs: 16-18, or an amino acid sequence having one, two, three, four or five amino acid substitutions, deletions or additions as compared to SEQ ID NOs: 16-18.

Engineered antibodies of the invention include those in which modifications have been made to framework residues within $V_H$ and/or $V_L$, e.g. to improve the properties of the antibody. Typically such framework modifications are made to decrease the immunogenicity of the antibody. One approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived.

For example, Table A shows regions where a framework region amino acid position (using the Kabat numbering system) differs from the germline and how this position can be backmutated to the germline by the indicated substitutions:

TABLE A

Exemplary Backmutations

| Region | Framework Amino Acid Position | Backmutation |
|---|---|---|
| 3C10 $V_H$ | 3 | Y3Q |
| 3C10 $V_H$ | 27 | I27F |
| 3C10 $V_H$ | 82 | L82Q |
| 6A4 $V_H$ | 3 | H3Q |
| 6A4 $V_H$ | 23 | V23A |
| 6A4 $V_H$ | 27 | I27F |
| 6A4 $V_H$ | 30 | R30S |
| 6A4 $V_H$ | 93 | I93V |
| 7B1 $V_H$ | 3 | H3Q |
| 7B1 $V_H$ | 41 | Q41P |
| 7B1 $V_H$ | 80 | S80Y |

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in US 2003/0153043 by Carr et al.

In addition or alternative to modifications made within the framework or CDR regions, antibodies of the invention may be engineered to include modifications within the Fc region, typically to alter one or more functional properties, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties. Each of these embodiments is described in further detail below. The numbering of residues in the Fc region is that of the EU index of Kabat.

In one embodiment, the hinge region of CH1 is modified such that the number of cysteine residues in the hinge region is altered (i.e., increased or decreased), as described in U.S. Pat. No. 5,677,425 by Bodmer et al. Such alteration can facilitate assembly of the light and heavy chains or increase or decrease the stability of the antibody.

In another embodiment, the Fc hinge region of an antibody is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding, as described in U.S. Pat. No. 6,165,745 by Ward et al.

In another embodiment, the antibody is modified to increase its biological half life. For example, one or more of the following mutations can be introduced: T252L, T254S, T256F, as described in U.S. Pat. No. 6,277,375 to Ward. Alternatively, the antibody can be altered within the CH1 or $C_L$ region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter its effector function(s). For example, one or more of amino acid residues 234, 235, 236, 237, 297, 318, 320 and 322 can be replaced with a different amino acid residue such that the antibody has an altered affinity for an effector ligand—e.g., an Fc receptor or the C1 component of complement—but retains the antigen-binding ability of the parent antibody, as described in U.S. Pat. Nos. 5,624,821 and 5,648,260, both to Winter et al.

In another example, one or more of amino acid residues 329, 331 and 322 can be replaced such that the antibody has altered Clq binding and/or reduced or abolished complement dependent cytotoxicity (CDC), as described in U.S. Pat. No. 6,194,551 by Idusogie et al.

In another example, one or more amino acid residues within amino acid positions 231 and 239 are altered to thereby alter the ability of the antibody to fix complement. This approach is described further in WO 94/29351 by Bodmer et al.

In yet another example, the Fc region is modified to increase the ability of the antibody to mediate antibody dependent cellular cytotoxicity (ADCC) and/or to increase the affinity of the antibody for an Fcγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in WO 00/42072 by Presta. Moreover, the binding sites on human IgG1 for FcγR1, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A.

In still another embodiment, the C-terminal end of an antibody of the present invention is modified by the introduction of a cysteine residue, as described in PCT/US2008/073569, which is incorporated by reference in its entirety. Such modifications include, but are not limited to, the replacement of an existing amino acid residue at or near the C-terminus of a full-length heavy chain sequence, as well as the introduction of a cysteine-containing extension to the c-terminus of a full-length heavy chain sequence. In preferred embodiments, the cysteine-containing extension comprises the sequence cysteine-alanine-alanine (from N-terminal to C-terminal).

In preferred embodiments the presence of such C-terminal cysteine modifications provide a location for conjugation of a partner molecule, such as a therapeutic agent or a marker molecule. In particular, the presence of a reactive thiol group, due to the C-terminal cysteine modification, can be used to conjugate a partner molecule employing the disulfide linkers or a sulfhydryl-reactive maleimide group. Conjugation of the antibody to a partner molecule in this manner allows for increased control over the specific site of attachment. Furthermore, by introducing the site of attachment at or near the C-terminus, conjugation can be optimized such that it reduces or eliminates interference with the antibody's functional properties, and allows for simplified analysis and quality control of conjugate preparations.

In still another embodiment, the glycosylation of an antibody is modified by eliminating glycosylation (aglycosylation) or altering the site(s) of glycosylation, to increase its affinity for its antigen. For example, one or more amino acid substitutions can be made that result in elimination of one or more variable region framework glycosylation sites. Such aglycosylation may increase the affinity of the antibody for antigen. See U.S. Pat. Nos. 5,714,350 and 6,350,861 to Co et al. Additional approaches for altering glycosylation are described in U.S. Pat. No. 7,214,775 to Hanai et al.; U.S. Pat. No. 6,737,056 to Presta; US 20070020260 to Presta; WO 2007/084926 to Dickey et al.; WO 2006/089294 to Zhu et al.; and WO 2007/055916 to Ravetch et al.; each of which is incorporated by reference in its entirety.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. For example, the cell lines Ms704, Ms705, and Ms709 lack the fucosyltransferase gene, FUT8 (alpha (1,6) fucosyltransferase), such that antibodies expressed in these cell lines lack fucose on their carbohydrates. See US 2004/0110704 by Yamane et al. and Yamane-Ohnuki et al. (2004) *Biotechnol Bioeng* 87:614-22. As another example, EP 1,176,195 by Hanai et al. describes a cell line with a functionally disrupted FUT8 gene, which encodes a fucosyl transferase, such that antibodies expressed in such a cell line exhibit hypofucosylation. Hanai et al. also describe cell lines which have a low enzyme activity for adding fucose to the N-acetylglucosamine that binds to the Fc region of the antibody. WO 03/035835 by Presta describes a variant CHO cell line, Lec13 cells, with reduced ability to attach fucose to Asn(297)-linked carbohydrates, also resulting in hypofucosylation (see also Shields, R. L. et al. (2002) *J. Biol. Chem.* 277:26733-26740). WO 99/54342 by Umana et al. describes cell lines engineered to express glycoprotein-modifying glycosyl transferases, such that antibodies expressed by these cell lines exhibit increased bisecting GlcNac structures and increased ADCC activity of the antibodies (see also Umana et al. (1999) *Nat. Biotech.* 17:176-180). Alternatively, the fucose residues of the antibody may be cleaved off using a fucosidase enzyme (Tarentino, A. L. et al. (1975) *Biochem.* 14:5516-23).

Additionally or alternatively, an antibody can be made that has an altered type of glycosylation, wherein that alteration relates to the level of sialyation of the antibody. Such alterations are described in WO 2007/084926 to Dickey et al, and WO 2007/055916 to Ravetch et al., both of which are incoporated by reference. For example, one may employ an enzymatic reaction with sialidase, such as described in the U.S. Pat. No. 5,831,077, which is hereby incorporated by reference. Other examples of suitable enzymes are neuraminidase and N-Glycosidase F, as described in Schloemer et al., J. Virology, 15(4), 882-893 (1975) and in Leibiger et al., Biochem J., 338, 529-538 (1999), respectively. Alternatively, one may employ methods to increase the level of sialyation, such as by employing sialytransferase enzymes, as described in Basset et al., Scandinavian Journal of Immunology, 51(3), 307-311 (2000).

Another modification of the antibodies herein that is contemplated by the invention is pegylation. An antibody can be pegylated to, for example, increase its biological (e.g., serum) half life. To pegylate an antibody, the antibody, or fragment thereof, typically is reacted with a polyethylene glycol (PEG) derivative, such as a reactive ester or aldehyde derivative of PEG. Or, the pegylation is carried out via an acylation reaction or an alkylation reaction with a reactive PEG molecule (or an analogous reactive water-soluble polymer). As used herein, the term "polyethylene glycol" encompasses any of the forms of PEG that have been used to derivatize other proteins, such as mono (C1-C10) alkoxy- or aryloxy-polyethylene glycol or polyethylene glycol-maleimide. The antibody to be pegylated can be an aglycosylated antibody. Methods for pegylating proteins are known in the art and can be applied to the antibodies of the invention. See for example, EP 0 154 316 by Nishimura et al. and EP 0 401 384 by Ishikawa et al.

Antibody Fragments and Antibody Mimetics

The instant invention is not limited to traditional antibodies and may be practiced through the use of antibody fragments and antibody mimetics. A wide variety of antibody fragment and antibody mimetic technologies have now been developed and are widely known in the art.

Domain Antibodies (dAbs) are the smallest functional binding units of antibodies, corresponding to the variable regions of either the heavy (VH) or light (VL) chains of human antibodies. Domain Antibodies have a molecular weight of approximately 13 kDa. Domantis has developed a series of large and highly functional libraries of fully human VH and VL dAbs (more than ten billion different sequences in each library), and uses these libraries to select dAbs that are specific to therapeutic targets. In contrast to many conventional antibodies, Domain Antibodies are well expressed in bacterial, yeast, and mammalian cell systems. Further details of domain antibodies and methods of production thereof may be obtained by reference to U.S. Pat. Nos. 6,291,158; 6,582, 915; 6,593,081; 6,172,197; and 6,696,245; US 2004/ 0110941; EP 1433846, 0368684 and 0616640; WO 2005/ 035572, 2004/101790, 2004/081026, 2004/058821, 2004/ 003019 and 2003/002609, each of which is herein incorporated by reference in its entirety.

Nanobodies are antibody-derived therapeutic proteins that contain the unique structural and functional properties of naturally-occurring heavy-chain antibodies. These heavy-chain antibodies contain a single variable domain (VHH) and two constant domains (CH2 and CH3). Importantly, the cloned and isolated VHH domain is a perfectly stable polypeptide harbouring the full antigen-binding capacity of the original heavy-chain antibody. Nanobodies have a high homology with the VH domains of human antibodies and can be further humanized without any loss of activity. Importantly, Nanobodies have a low immunogenic potential, which has been confirmed in primate studies with Nanobody lead compounds.

Nanobodies combine the advantages of conventional antibodies with important features of small molecule drugs. Like conventional antibodies, Nanobodies show high target specificity and affinity and low inherent toxicity. However, like small molecule drugs they can inhibit enzymes and readily access receptor clefts. Furthermore, Nanobodies are extremely stable, can be administered by means other than injection (see, e.g., WO 2004/041867, incorporated herein by reference in its entirety) and are easy to manufacture. Other advantages of Nanobodies include recognizing uncommon or hidden epitopes as a result of their small size, binding into cavities or active sites of protein targets with high affinity and selectivity due to their unique 3-dimensional, drug format flexibility, tailoring of half-life and ease and speed of drug discovery.

Nanobodies are encoded by single genes and are efficiently produced in almost all prokaryotic and eukaryotic hosts, e.g., *E. coli* (see, e.g., U.S. Pat. No. 6,765,087, which is herein incorporated by reference in its entirety), molds (for example *Aspergillus* or *Trichoderma*) and yeast (for example *Saccha-*

*romyces, Kluyveromyces, Hansenula* or *Pichia*) (see, e.g., U.S. Pat. No. 6,838,254, which is herein incorporated by reference in its entirety).

The Nanoclone method (see, e.g., WO 06/079372, which is herein incorporated by reference in its entirety) generates Nanobodies against a desired target, based on automated high-throughout selection of B-cells and could be used in the context of the instant invention.

UniBodies are another antibody fragment technology, however based upon the removal of the hinge region of IgG4 antibodies. The deletion of the hinge region results in a molecule that is essentially half the size of a traditional IgG4 antibody and has a univalent binding region rather than the bivalent binding region of an IgG4 antibody. Like IgG4 antibodies, Unibodies are inert and do not interact with the immune system, which may be advantageous for the treatment of diseases where an immune response is not desired. UniBodies may function to inhibit or silence, but not kill, the cells to which they are bound. Additionally, UniBody binding to cancer cells does not stimulate them to proliferate. Furthermore, because UniBodies are about smaller, they may show better distribution over larger solid tumors with potentially advantageous efficacy. UniBodies are cleared from the body at a similar rate to whole IgG4 antibodies and are able to bind with a similar affinity for their antigens. Further details of UniBodies may be obtained by reference to WO 2007/059782, which is incorporated by reference in its entirety.

Affibody molecules are affinity proteins based on a 58-amino acid residue protein domain derived from a three helix bundle IgG-binding domain of staphylococcal protein A. This domain has been used as a scaffold for the construction of combinatorial phagemid libraries, from which Affibody variants targeting the desired molecules can be selected using phage display technology (Nord et al., Nat Biotechnol 1997; 15:772-7; Ronmark et al., Eur J Biochem 2002; 269: 2647-55). The simple, robust structure and low molecular weight (6 kDa) of Affibody molecules makes them suitable for a wide variety of applications, for instance, as detection reagents and inhibitors of receptor interactions. Further details on Affibodies and their production are found in U.S. Pat. No. 5,831,012 which is incorporated by reference in its entirety. Labelled Affibodies may also be useful in imaging applications for determining abundance of isoforms.

DARPins (Designed Ankyrin Repeat Proteins) embody DRP (Designed Repeat Protein) antibody mimetic technology developed to exploit the binding abilities of non-antibody polypeptides. Repeat proteins, such as ankyrin and leucine-rich repeat proteins, are ubiquitous binding molecules that, unlike antibodies, occur intra- and extracellularly. Their unique modular architecture features repeating structural units (repeats) that stack together to form elongated repeat domains displaying variable and modular target-binding surfaces. Based on this modularity, combinatorial libraries of polypeptides with highly diversified binding specificities can be generated. This strategy includes the consensus design of self-compatible repeats displaying variable surface residues and their random assembly into repeat domains.

DARPins can be produced in bacterial expression systems at very high yields and are among the most stable proteins known. Highly specific, high-affinity DARPins that bind to a broad range of target proteins, including human receptors, cytokines, kinases, human proteases, viruses and membrane proteins, have been made, including some having affinities in the single-digit nanomolar to picomolar range.

DARPins have been used in a wide range of applications, including ELISA, sandwich ELISA, flow cytometric analysis (FACS), immunohistochemistry (IHC), chip applications, affinity purification or Western blotting. DARPins are not only ideal to block protein-protein interactions, but also to inhibit enzymes. Very fast and specific enrichments on the tumor and very favorable tumor to blood ratios make DARPins well suited for in vivo diagnostics or therapeutic approaches. Additional information regarding DARPins and other DRP technologies can be found in US 2004/0132028 and WO 02/20565, both of which are incorporated by reference.

Anticalins are another antibody mimetic technology. However, in this case the binding specificity is derived from lipocalins, a family of low molecular weight proteins that are naturally and abundantly expressed in human tissues and body fluids. Lipocalins have evolved to perform a range of functions in vivo associated with the physiological transport and storage of chemically sensitive or insoluble compounds. Lipocalins have a robust intrinsic structure comprising a highly conserved β-barrel which supports four loops at one terminus of the protein. These loops form the entrance to a binding pocket and conformational differences in this part of the molecule account for the variation in binding specificity between individual lipocalins.

While the overall structure of hypervariable loops supported by a conserved β-sheet framework is reminiscent of immunoglobulins, lipocalins differ considerably from antibodies in terms of size, being composed of a single polypeptide chain of 160-180 amino acids, which is marginally larger than a single immunoglobulin domain.

Lipocalins can be cloned and their loops subjected to engineering in order to create Anticalins. Libraries of structurally diverse Anticalins have been generated and Anticalin display allows the selection and screening of binding function, followed by the expression and production of soluble protein for further analysis in prokaryotic or eukaryotic systems. Studies have demonstrated that Anticalins can be developed that are specific for virtually any human target protein and binding affinities in the nanomolar or higher range can be obtained.

Anticalins can also be formatted as dual targeting proteins (Duocalins). A Duocalin binds two separate therapeutic targets in one easily produced monomeric protein using standard manufacturing processes while retaining target specificity and affinity regardless of the structural orientation of its two binding domains.

Modulation of multiple targets through a single molecule is particularly advantageous in diseases known to involve more than a single causative factor. Moreover, bi- or multivalent binding formats such as Duocalins have significant potential in targeting cell surface molecules in disease, mediating agonistic effects on signal transduction pathways or inducing enhanced internalization effects via binding and clustering of cell surface receptors. Furthermore, the high intrinsic stability of Duocalins is comparable to monomeric Anticalins.

Additional information regarding Anticalins can be found in U.S. Pat. No. 7,250,297 and WO 99/16873, both of which are hereby incorporated by reference in their entirety.

Avimers are another type of antibody mimetic technology useful in the context of the instant invention. Avimers are evolved from a large family of human extracellular receptor domains by in vitro exon shuffling and phage display, generating multidomain proteins with binding and inhibitory properties. Linking multiple independent binding domains has been shown to create avidity and results in improved affinity and specificity compared to conventional single-epitope binding proteins. Other potential advantages include simple and efficient production of multi-target-specific molecules in *Escherichia coli*, improved thermostability and resistance to proteases. Avimers with sub-nanomolar affinities have been obtained against a variety of targets. Additional information regarding Avimers can be found in US 2006/0286603, 2006/0234299, 2006/0223114, 2006/0177831, 2006/0008844, 2005/0221384, 2005/0164301, 2005/0089932, 2005/0053973, 2005/0048512, 2004/0175756, all of which are hereby incorporated by reference in their entirety.

Versabodies are another antibody mimetic technology that can be used in the context of the instant invention. Versabodies are small proteins of 3-5 kDa with >15% cysteines, which form a high disulfide density scaffold replacing the hydrophobic core that typical proteins have. This replacement results in a protein that is smaller, is more hydrophilic (i.e., less prone to aggregation and non-specific binding), is more resistant to proteases and heat, and has a lower density of T-cell epitopes, because the residues that contribute most to MHC presentation are hydrophobic. All four of these properties are well-known to affect immunogenicity, and together they are expected to cause a large decrease in immunogenicity.

Given the structure of Versabodies, these antibody mimetics offer a versatile format that includes multi-valency, multi-specificity, a diversity of half-life mechanisms, tissue targeting modules and the absence of the antibody Fc region. Furthermore, Versabodies are manufactured in E. coli at high yields, and because of their hydrophilicity and small size, Versabodies are highly soluble and can be formulated to high concentrations. Versabodies are exceptionally heat stable and offer extended shelf-life. Additional information regarding Versabodies can be found in US 2007/0191272, which is hereby incorporated by reference in its entirety.

The above descriptions of antibody fragment and mimetic technologies is not intended to be comprehensive. A variety of additional technologies including alternative polypeptide-based technologies, such as fusions of complementarity determining regions as outlined in Qui et al., Nature Biotechnology, 25(8) 921-929 (2007), as well as nucleic acid-based technologies, such as the RNA aptamer technologies described in U.S. Pat. Nos. 5,789,157; 5,864,026; 5,712,375; 5,763,566; 6,013,443; 6,376,474; 6,613,526; 6,114,120; 6,261,774; and 6,387,620; all of which are hereby incorporated by reference, could be used in the context of the instant invention.

Antibody Physical Properties

Antibodies of this disclosure can be characterized by their various physical properties, to detect and/or differentiate different classes thereof.

Antibodies of the present disclosure may contain one or more glycosylation sites in either the light or heavy chain variable region. Such glycosylation sites may result in increased immunogenicity of the antibody or an alteration of the pK of the antibody due to altered antigen binding (Marshall et al (1972) Anna Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al. (2000) Mol Immunol 37:697-706). Glycosylation has been known to occur at motifs containing an N—X—S/T sequence. In some instances, it is preferred to have an anti-mesothelin antibody that does not contain variable region glycosylation. This can be achieved either by selecting antibodies that do not contain the glycosylation motif in the variable region or by mutating residues within the glycosylation region.

In a preferred embodiment, the antibodies of the present disclosure do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-mesothelin antibody that contains a pI value that falls in the normal range. This can be achieved either by selecting antibodies with a pI in the normal range or by mutating charged surface residues.

Each antibody will have a characteristic melting temperature, with a higher melting temperature indicating greater overall stability in vivo (Krishnamurthy R and Manning M C (2002) Curr Pharm Biotechnol 3:361-71). Generally, it is preferred that the $T_{M1}$ (the temperature of initial unfolding) be greater than 60° C., preferably greater than 65° C., even more preferably greater than 70° C. The melting point of an antibody can be measured using differential scanning calorimetry (Chen et al (2003) Pharm Res 20:1952-60; Ghirlando et al (1999) Immunol Lett 68:47-52) or circular dichroism (Murray et al. (2002) J. Chromatogr Sci 40:343-9).

In a preferred embodiment, antibodies are selected that do not degrade rapidly. Degradation of an antibody can be measured using capillary electrophoresis (CE) and MALDI-MS (Alexander A J and Hughes D E (1995) Anal Chem 67:3626-32).

In another preferred embodiment, antibodies are selected that have minimal aggregation effects, which can lead to the triggering of an unwanted immune response and/or altered or unfavorable pharmacokinetic properties. Generally, antibodies are acceptable with aggregation of 25% or less, preferably 20% or less, even more preferably 15% or less, even more preferably 10% or less and even more preferably 5% or less. Aggregation can be measured by several techniques, including size-exclusion column (SEC), high performance liquid chromatography (HPLC), and light scattering.

Methods of Engineering Antibodies

As discussed above, the anti-mesothelin antibodies having known $V_H$ and $V_L$ sequences can be used to create new anti-mesothelin antibodies by modifying them or the constant region(s) attached thereto. Thus, in another aspect of this disclosure, the structural features of a known anti-mesothelin antibody, e.g., 3C10, 6A4 or 7B1, are used to create structurally related anti-mesothelin antibodies that retain at least one functional property of the antibodies of this disclosure, such as binding to human mesothelin. For example, one or more CDR regions of known anti-mesothelin antibodies or mutations thereof, can be combined recombinantly with known framework regions and/or other CDRs to create additional, recombinantly-engineered, anti-mesothelin antibodies of this disclosure, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, this disclosure provides a method for preparing an anti-mesothelin antibody comprising:
- (a) providing: (i) a $V_H$ antibody sequence comprising a CDR1 sequence selected from the group consisting of SEQ ID NOs: 1-3, a CDR2 sequence selected from the group consisting of SEQ ID NOs: 4-6, and/or a CDR3 sequence selected from the group consisting of SEQ ID NOs: 7-9; and/or (ii) a $V_L$ antibody sequence comprising a CDR1 sequence selected from the group consisting of SEQ ID NOs: 10-12, a CDR2 sequence selected from the group consisting of SEQ ID NOs: 13-15, and/or a CDR3 sequence selected from the group consisting of SEQ ID NOs: 16-18;
- (b) altering at least one amino acid residue within the $V_L$ antibody sequence and/or the $V_L$ antibody sequence to create at least one altered antibody sequence; and
- (c) expressing the altered antibody sequence as a protein.

Standard molecular biology techniques can be used to prepare and express the altered antibody sequence.

In certain embodiments, mutations can be introduced randomly or selectively along all or part of an anti-mesothelin antibody coding sequence and the resulting modified anti-mesothelin antibodies can be screened for binding activity and/or other functional properties as described herein. Mutational methods have been described in the art. For example, WO 02/092780 by Short describes methods for creating and screening antibody mutations using saturation mutagenesis, synthetic ligation assembly, or a combination thereof. Alternatively, WO 03/074679 by Lazar et al. describes methods of using computational screening methods to optimize physiochemical properties of antibodies.

Nucleic Acid Molecules Encoding Antibodies of the Invention

Another aspect of this disclosure pertains to nucleic acid molecules that encode the antibodies of this disclosure. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) *Current Protocols in Molecular Biology*, Greene Publishing and Wiley Interscience, New York. A nucleic acid of this disclosure can be, for example, DNA or RNA and may or may not contain intronic sequences. In a preferred embodiment, the nucleic acid is a cDNA molecule.

Nucleic acids of this disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules are those encoding the $V_H$ and $V_L$ sequences of the 3C10, 6A4 or 7B1 monoclonal antibodies. DNA sequences encoding the $V_H$ sequences of 3C10, 6A4 and 7B1 are shown in SEQ ID NOs: 25-27, respectively. DNA sequences encoding the $V_L$ sequences of 3C10, 6A4 and 7B1 are shown in SEQ ID NOs: 28-30, respectively.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes, or to scFv genes. In these manipulations, a $V_L$- or $V_H$-encoding DNA fragment is operatively linked to another DNA fragment encoding another protein, such as an antibody constant region or a flexible linker. The term "operatively linked", as used in this context, means that the two DNA fragments are joined such that the amino acid sequences encoded by them remain in-frame.

The isolated DNA encoding the $V_H$ region can be converted to a full-length heavy chain gene by operatively linking the $V_H$-encoding DNA to a DNA molecule encoding heavy chain constant regions (CH1, CH2 and CH3). The sequences of human heavy chain constant region genes are known in the art (see e.g., Kabat '242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to a DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat '242) and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4\text{-}Ser)_3$, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

Production of Monoclonal Antibodies of this Disclosure

Monoclonal antibodies (mAbs) of the present disclosure can be produced by a variety of techniques, including the somatic cell hybridization technique of Kohler and Milstein (1975) *Nature* 256: 495. Although somatic cell hybridization procedures are preferred, in principle other techniques can be employed e.g., viral or oncogenic transformation of B lymphocytes.

The preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known.

Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions (see e.g., U.S. Pat. No. 4,816,567 to Cabilly et al.). To create a humanized antibody, murine CDR regions can be inserted into a human framework (see e.g., U.S. Pat. No. 5,225,539 to Winter, and U.S. Pat. Nos. 5,530,101; 5,585,089; 5,693,762 and 6,180,370 to Queen et al.).

Preferably, the antibodies are human monoclonal antibodies. They can be generated using transgenic or transchromosomic mice carrying parts of the human immune system rather than the mouse system. These transgenic and tranchromosomic mice include those of the HuMAb Mouse® and KM Mouse® types, respectively, and are collectively referred to herein as "human Ig mice."

The HuMAb Mouse® type of mouse (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg et al. (1994), supra; reviewed in Lonberg (1994) *Handbook of Experimental Pharmacology* 113:49-101; Lonberg and Huszar (1995) *Intern. Rev. Immunol.* 13: 65-93, and Harding and Lonberg (1995) *Ann. N.Y. Acad. Sci.* 764:536-546). Preparation and use of the HuMAb Mouse® type of mice, and the genomic modifications carried by such mice, is further described in Taylor et al. (1992) *Nucleic Acids Research* 20:6287-6295; Chen et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen et al. (1993) *EMBO J.* 12: 821-830; Tuaillon et al. (1994) *J. Immunol.* 152:2912-2920; Taylor. et al. (1994) *International Immunology* 6: 579-591; and Fishwild et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; WO 92/03918, WO 93/12227, WO 94/25585, WO 97/13852, WO 98/24884 and WO 99/45962, all to Lonberg and Kay; and WO 01/14424 to Korman et al. Transgenic mice carrying human lambda light chain genes also can be used, such as those described in WO 00/26373 by Bruggemann. For example, a mouse carrying a human lambda light chain transgene can be crossbred with a mouse carrying a human heavy chain transgene (e.g., HCo7), and optionally also carrying a human kappa light chain transgene (e.g., KCoS) to create a mouse carrying both human heavy and light chain transgenes (see e.g., Example 1).

In another embodiment, human antibodies of this disclosure can be generated using a mouse that carries human immunoglobulin sequences on transgenes and transchromosomes, such as one carrying a human heavy chain transgene and a human light chain transchromosome. This mouse is referred to herein as being of the KM Mouse® strain or type and is described in detail in WO 02/43478 to Ishida et al.

Still further, alternative transgenic animal systems expressing human immunoglobulin genes are available in the art and can be used to raise anti-mesothelin antibodies of this disclosure. For example, an alternative transgenic system referred to as the Xenomouse (Abgenix, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to generate anti-mesothelin antibodies of this disclosure. For example, mice carrying both a human heavy chain transchromosome and a human light chain tranchromosome, referred to as "TC mice" can be used; such mice are described in Tomizuka et al. (2000) *Proc. Natl. Acad. Sci. USA* 97:722-727. Furthermore, cows carrying human heavy and light chain transchromosomes have been disclosed (e.g., Kuroiwa et al. (2002) *Nature Biotechnology* 20:889-894 and WO 2002/092812).

Human monoclonal antibodies of this disclosure can also be prepared using phage display methods for screening libraries of human immunoglobulin genes. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of this disclosure can also be prepared using SCID mice into which human immune cells have been reconstituted such that a human antibody response can be generated upon immunization. Such mice are described in U.S. Pat. Nos. 5,476,996 and 5,698,767 to Wilson et al.

In another embodiment, human anti-mesothelin antibodies are prepared using a combination of human Ig mouse and phage display techniques, as described in U.S. Pat. No. 6,794,132 by Buechler et al. More specifically, the method first involves raising an anti-mesothelin antibody response in a human Ig mouse (such as those of the HuMab Mouse® or KM Mouse® strains) by immunizing the mouse with one or more mesothelin antigens, followed by isolating nucleic acids encoding human antibody chains from lymphatic cells of the mouse and introducing these nucleic acids into a display vector (e.g., phage) to provide a library of display packages. Thus, each library member comprises a nucleic acid encoding a human antibody chain and each antibody chain is displayed from the display package. The library then is screened with mesothelin protein to isolate library members that specifically bind to mesothelin. Nucleic acid inserts of the selected library members then are isolated and sequenced by standard methods to determine the light and heavy chain variable sequences of the selected mesothelin binders. The variable regions can be converted to full-length antibody chains by standard recombinant DNA techniques, such as cloning of the variable regions into an expression vector that carries the human heavy and light chain constant regions such that the $V_H$ region is operatively linked to the $C_H$ region and the $V_L$ region is operatively linked to the $C_L$ region.

Immunization of Human Ig Mice

When human Ig mice are used to generate human antibodies of this disclosure, such mice can be immunized with a purified or enriched preparation of a mesothelin antigen and/or recombinant mesothelin protein, cells expressing a mesothelin protein, or a mesothelin fusion protein, as described by Lonberg, N. et al. (1994) *Nature* 368(6474): 856-859; Fishwild, D. et al. (1996) *Nature Biotechn.* 14: 845-851; and WO 98/24884 and WO 01/14424. Preferably, the mice are 6-16 weeks of age upon the first infusion. For example, a purified or recombinant preparation (5-50 μg) of mesothelin antigen is used to immunize the human Ig mice intraperitoneally and/or subcutaneously. Most preferably, the immunogen used to raise the antibodies of this disclosure is a mesothelin fusion protein comprising the extracellular domain of a mesothelin protein, fused at its N-terminus to a non-mesothelin polypeptide (e.g., a His tag) (see, e.g., Example 1).

Detailed procedures to generate fully human monoclonal antibodies that bind human mesothelin are described in Example 1. Cumulative experience with various antigens has shown that transgenic mice of the HuMAb Mouse type respond when initially immunized intraperitoneally (IP) with antigen in complete Freund's adjuvant, followed by every other week IP immunizations (up to a total of 6) with antigen in incomplete Freund's adjuvant. Adjuvants other than Freund's (e.g., RIBI adjuvant) are also effective. In addition, whole cells in the absence of adjuvant are found to be highly immunogenic. The immune response can be monitored over the course of the immunization protocol with plasma samples obtained by retroorbital bleeds. The plasma can be screened by ELISA, and mice with sufficient titers of anti-mesothelin human immunoglobulin can be used for fusions. Mice can be boosted intravenously with antigen, for example 3 days before sacrifice and removal of the spleen. It is expected that 2-3 fusions for each immunization may be needed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo12). Alternatively or additionally, the KM Mouse® strain can be used.

Generation of Hybridomas Producing Human Monoclonal Antibodies of the Invention

To generate hybridomas producing human monoclonal antibodies of this disclosure, splenocytes and/or lymph node cells from immunized mice are isolated and fused to an appropriate immortalized cell line, such as a mouse myeloma cell line. The resulting hybridomas are screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Alternatively, the single cell suspension of splenic lymphocytes from immunized mice can be fused by electrofusion, using a CytoPulse large chamber cell fusion electroporator (CytoPulse Sciences, Inc., Glen Burnie, Md.). Cells are plated at approximately $2\times10^5$ in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/mL penicillin, 50 mg/mL streptomycin, 50 mg/mL gentamycin and 1×HAT (Sigma; the HAT is added 24 hours after the fusion). After approximately two weeks, cells are cultured in medium in which the HAT is replaced with HT. Individual wells are then screened by ELISA for human monoclonal IgM and IgG antibodies. Once extensive hybridoma growth occurs, medium is observed, usually after 10-14 days. The antibody secreting hybridomas are replated, screened again, and if still positive for human IgG, the monoclonal antibodies are subcloned at least twice by limiting dilution. The stable subclones are then cultured in vitro to generate small amounts of antibody in tissue culture medium for characterization.

To purify human monoclonal antibodies, selected hybridomas are grown in two-liter spinner-flasks for monoclonal antibody purification. Supernatants can be filtered and concentrated before affinity chromatography with protein A-sepharose (Pharmacia, Piscataway, N.J.). Eluted IgG fractions are checked by gel electrophoresis and HPLC to ensure purity. The buffer solution is exchanged into PBS, and the concentration is determined by OD280 using extinction coefficient of 1.43. The monoclonal antibodies are aliquoted and stored at −80° C.

Generation of Transfectomas Producing Monoclonal Antibodies of the Invention

Antibodies of this disclosure also can be produced in a host cell transfectoma using, for example, a combination of recombinant DNA techniques and gene transfection methods as is well known in the art (e.g., Morrison, S. (1985) *Science* 229:1202).

For example, to express the antibodies, or antibody fragments thereof, DNAs encoding partial or full-length light and heavy chains, are obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene are inserted into separate vectors or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of this disclosure carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, etc. Preferred regulatory sequences for mammalian host cell expression include viral elements that direct high levels of protein expression in mammalian cells, such as those derived from cytomegalovirus (CMV), Simian Virus 40 (SV40), adenovirus, (e.g., the adenovirus major late promoter (AdMLP) and polyoma. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, the recombinant expression vectors of this disclosure may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr−host cells with methotrexate selection/amplification) and the neo gene (for G418 selection).

For expression of the light and heavy chains, the expression vector(s) encoding them are transfected into a host cell. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of this disclosure in either prokaryotic or eukaryotic host cells, expression of antibodies in eukaryotic cells, and most preferably mammalian host cells, is the most preferred because they are more likely than prokaryotic cells to assemble and secrete a properly folded and immunologically active antibody.

Preferred mammalian host cells for expressing the recombinant antibodies of this disclosure include Chinese Hamster Ovary (CHO cells) (including dhfr− CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Characterization of Antibody Binding to Antigen

Antibodies of the invention can be tested for binding to human mesothelin by, for example, standard ELISA. Briefly, microtiter plates are coated with purified and/or recombinant mesothelin protein (see, e.g., Example 1) at 1 μg/mL in PBS, and then blocked with 5% bovine serum albumin in PBS. Dilutions of antibody (e.g., dilutions of plasma from mesothelin-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/mL), and analyzed at OD of 405-650. Preferably, mice that develop the highest titers will be used for fusions.

An ELISA assay as described above can also be used to screen for hybridomas that show positive reactivity with a mesothelin protein. Hybridomas that bind with high avidity and/or affinity to a mesothelin protein are subcloned and further characterized. One clone from each hybridoma, which retains the reactivity of the parent cells (by ELISA), can be chosen for making a 5-10 vial cell bank stored at −140° C., and for antibody purification.

To purify anti-mesothelin antibodies, selected hybridomas are grown in two-liter spinner-flasks for monoclonal antibody purification. Supernatants are filtered and concentrated before affinity chromatography with protein A-sepharose (Pharmacia, Piscataway, N.J.). Eluted IgG fractions are checked by gel electrophoresis and HPLC to ensure purity. The buffer solution is exchanged into PBS, and the concentration is determined by OD280 using an extinction coefficient of 1.43. The monoclonal antibodies are aliquoted and stored at −80° C.

To determine if the selected anti-mesothelin monoclonal antibodies bind to unique epitopes, each antibody is biotinylated using commercially available reagents (Pierce, Rockford, Ill.). Competition studies using unlabeled monoclonal antibodies and biotinylated monoclonal antibodies are performed using mesothelin protein coated-ELISA plates as described above. Biotinylated mAb binding can be detected with a strep-avidin-alkaline phosphatase probe.

To determine the isotype of purified antibodies, isotype ELISAs can be performed using reagents specific for a particular isotype. For example, to determine the isotype of a human monoclonal antibody, wells of microtiter plates can be coated with 1 μg/mL of anti-human immunoglobulin overnight at 4° C. After blocking with 1% BSA, the plates are reacted with 1 μg/mL or less of test monoclonal antibodies or purified isotype controls, at ambient temperature for one to two hours. The wells are then reacted with either human IgG1 or human IgM-specific alkaline phosphatase-conjugated probes. Plates are developed and analyzed as described above.

Anti-mesothelin human IgGs also can be tested for reactivity with a mesothelin antigen by Western blotting. Briefly, a mesothelin antigen is prepared and subjected to sodium dodecyl sulfate polyacrylamide gel electrophoresis. The separated antigens are transferred to nitrocellulose membranes, blocked with 10% fetal calf serum, and probed with the monoclonal antibodies to be tested. Human IgG binding is detected using anti-human IgG alkaline phosphatase and developed with BCIP/NBT substrate tablets (Sigma Chem. Co., St. Louis, Mo.).

The binding specificity of an antibody of this disclosure can also be determined by monitoring binding of the antibody to cells expressing a mesothelin protein, for example by flow cytometry. Cells or cell lines that naturally expresses mesothelin protein, such OVCAR3, NCI-H226, CFPAC-1 or KB cells, can be used, or a cell line such as a CHO cell line can be transfected with an expression vector encoding mesothelin such that mesothelin is expressed on the cell surface. The transfected protein may comprise a tag, such as a myc-tag or a his-tag, preferably at the N-terminus, for detection using an antibody to the tag. Binding of an antibody of this disclosure to a mesothelin protein can be determined by incubating the transfected cells with the antibody, and detecting bound antibody. Binding of an antibody to the tag on the transfected protein may can used as a positive control.

Bispecific Molecules

In another aspect, the present disclosure features bispecific molecules comprising an anti-mesothelin antibody, or a fragment thereof, of this disclosure linked to another functional molecule, e.g., another peptide or protein such as another antibody, a binding mimetic, or a ligand for a receptor, which bind to at least two different binding sites or target molecules. The antibody of this disclosure may in fact be linked to more than one other functional molecule to generate multispecific molecules that bind to more than two different binding sites and/or target molecules. Such multispecific molecules are also intended to be encompassed by the term "bispecific molecule" as used herein. The linkage can be by chemical coupling, genetic fusion, noncovalent association or otherwise.

Accordingly, the present disclosure includes bispecific molecules comprising at least one first binding specificity for mesothelin and a second binding specificity for a second target epitope. In a particular embodiment of this disclosure, the second target epitope is an Fc receptor, e.g., human FcγRI (CD64) or a human Fcα receptor (CD89). Therefore, this disclosure includes bispecific molecules capable of binding both to FcγR or FcαR expressing effector cells (e.g., monocytes, macrophages or polymorphonuclear cells (PMNs)), and to target cells expressing mesothelin protein. These bispecific molecules target mesothelin expressing cells to effector cell and trigger Fc receptor-mediated effector cell activities, such as phagocytosis of mesothelin expressing cells, ADCC, cytokine release, or generation of superoxide anion.

Where the bispecific molecule is multispecific, the molecule can further include a third binding specificity, in addition to an anti-Fc binding specificity and an anti-mesothelin binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g. via CD2, CD3, CD8, CD28, CD4, CD40, ICAM-1) or other immune cell that results in an increased immune response against the target cell).

In one embodiment, the bispecific molecules of this disclosure comprise as a binding specificity at least one antibody, or an antibody fragment thereof, including, e.g., an Fab, Fab', F(ab')$_2$, Fv, Fd, dAb or a single chain Fv. The antibody may also be a light chain or heavy chain dimer, or any minimal fragment thereof such as a Fv or a single chain construct as described in U.S. Pat. No. 4,946,778 to Ladner et al., the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of certain preferred anti-Fcγ monoclonal antibodies are described in WO 88/00052 and in U.S. Pat. No. 4,954,617 to Fanger et al., which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this disclosure are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol* 155 (10): 4996-5002 and WO 94/10332 to Tempest et al. The H22 antibody producing cell line was deposited at the American Type Culture Collection under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity ($\approx 5\times 10^7$ M$^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

FcαRI and FcγRI are preferred trigger receptors for use in the bispecific molecules of this disclosure because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); and (4) mediate enhanced antigen presentation of antigens, including self-antigens, targeted to them.

While human monoclonal antibodies are preferred, other antibodies which can be employed in the bispecific molecules of this disclosure are murine, chimeric and humanized monoclonal antibodies.

The bispecific molecules of the present disclosure can be prepared by conjugating the constituent binding specificities, e.g., the anti-FcR and anti-mesothelin binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160:

1686; Liu, M A et al. (1985) *Proc. Natl. Acad. Sci. USA* 82:8648). Other methods include those described in Paulus (1985) *Behring Ins. Mitt. No.* 78, 118-132; Brennan et al. (1985) *Science* 229:81-83, and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand× Fab fusion protein. A bispecific molecule of this disclosure can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455, 030; 4,881,175; 5,132,405; 5,091,513; 5,476,786; 5,013,653; 5,258,498; and 5,482,858, all of which are expressly incorporated herein by reference.

Binding of the bispecific molecules to their specific targets can be confirmed by, for example, ELISA, radioimmunoassay (RIA), FACS analysis, bioassay (e.g., growth inhibition), or Western Blot assay. Each of these assays generally detects the presence of protein-antibody complexes of interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ or scintillation counter or by autoradiography.

Conjugates

In another aspect, there is provided an antibody-partner molecule conjugate, wherein a partner molecule is conjugated to an antibody of this invention by a chemical linker (sometimes referred to herein simply as "linker"). The partner molecule can be a therapeutic agent or a marker. The therapeutic agent can be, for example, a cytotoxin, a non-cytotoxic drug (e.g., an immunosuppressant), a radioactive agent, another antibody, or an enzyme. Preferably, the partner molecule is a cytotoxin. The marker can be any label that generates a detectable signal, such as a radiolabel, a fluorescent label, or an enzyme that catalyzes a detectable modification to a substrate. The antibody serves a targeting function: by binding to a target tissue or cell where its antigen is found, the antibody steers the conjugate to the target tissue or cell. There, the linker is cleaved, releasing the partner molecule to perform its desired biological function. In some instances, the conjugate is internalized within a target cell and the cleavage occurs therewithin.

Linkers

In some embodiments, the linker is a peptidyl linker, depicted herein as $(L^4)_p$-F-$(L^1)_m$. Other linkers include hydrazine and disulfide linkers, depicted herein as $(L^4)_p$-H-$(L^1)_m$ and $(L^4)_p$-J-$(L^1)_m$, respectively. F, H, and J are peptidyl, hydrazine, and disulfide moieties, respectively, that are cleavable to release the partner molecule from the antibody, while $L^1$ and $L^4$ are linker groups. F, H, J, $L^1$, and $L^4$ are more fully defined hereinbelow, along with the subscripts p and m. The preparation and use of these and other linkers is described in WO 2005/112919, the disclosure of which is incorporated herein by reference.

The use of peptidyl and other linkers in antibody-partner conjugates is described in US 2006/0004081; 2006/0024317; 2006/0247295; 6,989,452; 7,087,600; and 7,129,261; WO 2007/051081; 2007/038658; 2007/059404; and 2007/ 089100; all of which are incorporated herein by reference.

Additional linkers are described in U.S. Pat. No. 6,214, 345; 2003/0096743; and 2003/0130189; de Groot et al., J. Med. Chem. 42, 5277 (1999); de Groot et al. J. Org. Chem. 43, 3093 (2000); de Groot et al., J. Med. Chem. 66, 8815, (2001); WO 02/083180; Carl et al., J. Med. Chem. Lett. 24, 479, (1981); Dubowchik et al., Bioorg & Med. Chem. Lett. 8, 3347 (1998), the disclosures of which are incorporated herein by reference.

In addition to connecting the antibody and the partner molecule, a linker can impart stability to the partner molecule, reduce its in vivo toxicity, or otherwise favorably affect its pharmacokinetics, bioavailability and/or pharmacodynamics. It is generally preferred that the linker is cleaved, releasing the partner molecule, once the conjugate is delivered to its site of action. Also preferably, the linkers are traceless, such that once removed from the partner molecule (such as during activation), no trace of the linker's presence remains.

In another embodiment, the linkers are characterized by their ability to be cleaved at a site in or near a target cell such as at the site of therapeutic action or marker activity of the partner molecule. Such cleavage can be enzymatic in nature. This feature aids in reducing systemic activation of the partner molecule, reducing toxicity and systemic side effects. Preferred cleavable groups for enzymatic cleavage include peptide bonds, ester linkages, and disulfide linkages, such as the aforementioned F, H, and J moieties. In other embodiments, the linkers are sensitive to pH and are cleaved through changes in pH.

An important aspect is the ability to control the speed with which the linkers cleave. Often a linker that cleaves quickly is desired. In some embodiments, however, a linker that cleaves more slowly may be preferred. For example, in a sustained release formulation or in a formulation with both a quick release and a slow release component, it may be useful to provide a linker which cleaves more slowly. The aforecited WO 2005/112919 discloses hydrazine linkers that can be designed to cleave at a range of speeds, from very fast to very slow.

The linkers can also serve to stabilize the partner molecule against degradation while the conjugate is in circulation, that is, before it reaches the target tissue or cell. This feature provides a significant benefit since it prolongates the circulation half-life of the partner molecule. The linker also serves to attenuate the activity of the partner molecule so that the conjugate is relatively benign while in circulation but the partner molecule has the desired effect—for example is cytotoxic—after activation at the desired site of action. For therapeutic agent conjugates, this feature of the linker serves to improve the therapeutic index of the agent.

In addition to the cleavable peptide, hydrazine, or disulfide groups F, H, or J, respectively, one or more linker groups $L^1$ are optionally introduced between the partner molecule and F, H, or J, as the case may be. These linker groups $L^1$ may also be described as spacer groups and contain at least two functional groups. Depending on the value of the subscript m (i.e., the number of $L^1$ groups present) and the location of a particular group $L^1$, a chemical functionality of a group $L^1$ can bond to a chemical functionality of the partner molecule, of F, H or J, as the case may be, or of another linker group $L^1$ (if more than one $L^1$ is present). Examples of suitable chemical functionalities for spacer groups $L^1$ include hydroxy, mercapto, carbonyl, carboxy, amino, ketone, aldehyde, and mercapto groups.

The linkers $L^1$ can be a substituted or unsubstituted alkyl, substituted or unsubstituted aryl, substituted or unsubstituted heteroaryl or substituted or unsubstituted heteroalkyl group. In one embodiment, the alkyl or aryl groups may comprise between 1 and 20 carbon atoms. They may also comprise a polyethylene glycol moiety.

Exemplary groups $L^1$ include, for example, 6-aminohexanol, 6-mercaptohexanol, 10-hydroxydecanoic acid, glycine and other amino acids, 1,6-hexanediol, β-alanine, 2-aminoethanol, cysteamine (2-aminoethanethiol), 5-aminopentanoic acid, 6-aminohexanoic acid, 3-maleimidobenzoic acid, phthalide, α-substituted phthalides, the carbonyl group, aminal esters, nucleic acids, peptides and the like.

One function of the groups $L^1$ is to provide spatial separation between F, H or J, as the case may be, and the partner molecule, lest the latter interfere (e.g., via steric or electronic effects) with cleavage chemistry at F, H, or J. The groups $L^1$ also can serve to introduce additional molecular mass and chemical functionality into conjugate. Generally, the additional mass and functionality affects the serum half-life and other properties of the conjugate. Thus, through careful selection of spacer groups, conjugates with a range of serum half-lives can be produced. Optionally, one or more linkers $L^1$ can be a self-immolative group, as described hereinbelow.

The subscript m is an integer selected from 0, 1, 2, 3, 4, 5, and 6. When multiple $L^1$ groups are present, they can be the same or different.

$L^4$ is a linker moiety that provides spatial separation between F, H, or J, as the case may be, and the antibody, lest F, H, or J interfere with the antigen binding by the antibody or the antibody interfere with the cleavage chemistry at F, H, or J. Preferably, $L^4$ imparts increased solubility or decreased aggregation properties to conjugates utilizing a linker that contains the moiety or modifies the hydrolysis rate of the conjugate. As in the case of $L^1$, $L^4$ optionally is a self immolative group. In one embodiment, the $L^4$ moiety is substituted alkyl, unsubstituted alkyl, substituted aryl, unsubstituted aryl, substituted heteroalkyl, or unsubstituted heteroalkyl, any of which may be straight, branched, or cyclic. The substitutions can be, for example, a lower ($C_1$-$C_6$) alkyl, alkoxy, alkylthio, alkylamino, or dialkylamino. In certain embodiments, $L^4$ comprises a non-cyclic moiety. In another embodiment, $L^4$ comprises a positively or negatively charged amino acid polymer, such as polylysine or polyarginine. $L^4$ can comprise a polymer such as a polyethylene glycol moiety. Additionally the $L^4$ linker can comprise, for example, both a polymer component and a small molecule moiety.

In a preferred embodiment, $L^4$ comprises a polyethylene glycol (PEG) moiety. The PEG portion of $L^4$ may be between 1 and 50 units long. Preferably, the PEG will have 1-12 repeat units, more preferably 3-12 repeat units, more preferably 2-6 repeat units, or even more preferably 3-5 repeat units and most preferably 4 repeat units. $L^4$ may consist solely of the PEG moiety, or it may also contain an additional substituted or unsubstituted alkyl or heteroalkyl. It is useful to combine PEG as part of the $L^4$ moiety to enhance the water solubility of the complex. Additionally, the PEG moiety reduces the degree of aggregation that may occur during the conjugation of the drug to the antibody.

The subscript p is 0 or 1; that is, the presence of $L^4$ is optional. Where present, $L^4$ has at least two functional groups, with one functional group binding to a chemical functionality in F, H, or J, as the case may be, and the other functional group binding to the antibody. Examples of suitable chemical functionalities of groups $L^4$ include hydroxy, mercapto, carbonyl, carboxy, amino, ketone, aldehyde, and mercapto groups. As antibodies typically are conjugated via sulfhydryl groups (e.g., from unoxidized cysteine residues, the addition of sulfhydryl-containing extensions to lysine residues with iminothiolane, or the reduction of disulfide bridges), amino groups (e.g., from lysine residues), aldehyde groups (e.g., from oxidation of glycoside side chains), or hydroxyl groups (e.g., from serine residues), preferred chemical functionalities for attachment to the antibody are those reactive with the foregoing groups, examples being maleimide, sulfhydryl, aldehyde, hydrazine, semicarbazide, and carboxyl groups. The combination of a sulfhydryl group on the antibody and a maleimide group on $L^4$ is preferred.

In some embodiments, $L^4$ comprises

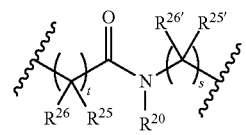

directly attached to the N-terminus of $(AA^1)_c$. $R^{20}$ is a member selected from H, substituted or unsubstituted alkyl, substituted or unsubstituted heteroalkyl, and acyl. Each $R^{25}$, $R^{25'}$, $R^{26}$, and $R^{26'}$ is independently selected from H, substituted or unsubstituted alkyl, substituted or unsubstituted heteroalkyl, substituted or unsubstituted aryl, substituted or unsubstituted heteroaryl, and substituted or unsubstituted heterocycloalkyl; and s and t are independently integers from 1 to 6. Preferably, $R^{20}$, $R^{25}$, $R^{25'}$, $R^{26}$ and $R^{26'}$ are hydrophobic. In some embodiments, $R^{20}$ is H or alkyl (preferably, unsubstituted lower alkyl). In some embodiments, $R^{25}$, $R^{25'}$, $R^{26}$ and $R^{26'}$ are independently H or alkyl (preferably, unsubstituted $C^1$ to $C^4$ alkyl). In some embodiments, $R^{25}$, $R^{25'}$, $R^{26}$ and $R^{26'}$ are all H. In some embodiments, t is 1 and s is 1 or 2.

Peptide Linkers (F)

As discussed above, the peptidyl linkers of the invention can be represented by the general formula: $(L^4)_p$-F-$(L^1)_m$, wherein F represents the portion comprising the peptidyl moiety. In one embodiment, the F portion comprises an optional additional self-immolative linker $L^2$ and a carbonyl group, corresponding to a conjugate of formula (a):

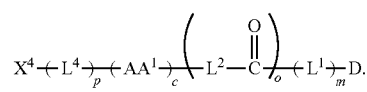

In this embodiment, $L^1$, $L^4$, p, and m are as defined above. $X^4$ is an antibody and D is a partner molecule. The subscript o is 0 or 1 and $L^2$, if present, represents a self-immolative linker. $AA^1$ represents one or more natural amino acids, and/or unnatural α-amino acids; c is an integer from 1 and 20. In some embodiments, c is in the range of 2 to 5 or c is 2 or 3.

In formula (a), $AA^1$ is linked, at its amino terminus, either directly to $L^4$ or, when $L^4$ is absent, directly to $X^4$. In some embodiments, when $L^4$ is present, $L^4$ does not comprise a carboxylic acyl group directly attached to the N-terminus of $(AA^1)_c$.

In another embodiment, the F portion comprises an amino group and an optional spacer group $L^3$ and $L^1$ is absent (i.e., m is 0), corresponding to a conjugate of formula (b):

In this embodiment, $X^4$, D, $L^4$, $AA^1$, c, and p are as defined above. The subscript o is 0 or 1. $L^3$, if present, is a spacer group comprising a primary or secondary amine or a carboxyl functional group, and either the amine of $L^3$ forms an amide bond with a pendant carboxyl functional group of D or the carboxyl of $L^3$ forms an amide bond with a pendant amine functional group of D.

Self-Immolative Linkers

A self-immolative linker is a bifunctional chemical moiety which is capable of covalently linking together two spaced chemical moieties into a normally stable tripartate molecule, releasing one of said spaced chemical moieties from the tripartate molecule by means of enzymatic cleavage; and following said enzymatic cleavage, spontaneously cleaving from the remainder of the molecule to release the other of said spaced chemical moieties. In accordance with the present invention, the self-immolative spacer is covalently linked at one of its ends to the peptide moiety and covalently linked at its other end to the chemically reactive site of the drug moiety whose derivatization inhibits pharmacological activity, so as to space and covalently link together the peptide moiety and the drug moiety into a tripartate molecule which is stable and pharmacologically inactive in the absence of the target enzyme, but which is enzymatically cleavable by such target enzyme at the bond covalently linking the spacer moiety and the peptide moiety to thereby effect release of the peptide moiety from the tripartate molecule. Such enzymatic cleavage, in turn, will activate the self-immolating character of the spacer moiety and initiate spontaneous cleavage of the bond covalently linking the spacer moiety to the drug moiety, to thereby effect release of the drug in pharmacologically active form. See, for example, Carl et al., J. Med. Chem., 24 (3), 479-480 (1981); Carl et al., WO 81/01145 (1981); Toki et al., J. Org. Chem. 67, 1866-1872 (2002); Boyd et al., WO 2005/112919; and Boyd et al., WO 2007/038658, the disclosures of which are incorporated herein by reference.

One particularly preferred self-immolative spacer may be represented by the formula (c):

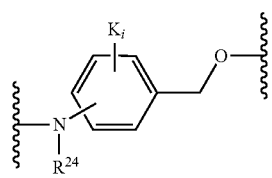

The aromatic ring of the aminobenzyl group may be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Each K is independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$, wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl. Exemplary K substituents include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In one preferred embodiment, i is 0.

The ether oxygen atom of the structure shown above is connected to a carbonyl group. The line from the $NR^{24}$ functionality into the aromatic ring indicates that the amine functionality may be bonded to any of the five carbons that both form the ring and are not substituted by the —$CH_2$—O— group. Preferably, the $NR^{24}$ functionality of X is covalently bound to the aromatic ring at the para position relative to the —$CH_2$—O— group. $R^{24}$ is a member selected from the group consisting of H, substituted alkyl, unsubstituted alkyl, substituted heteroalkyl, and unsubstituted heteroalkyl. In a specific embodiment, $R^{24}$ is hydrogen.

In one embodiment, the invention provides a peptide linker of formula (a) above, wherein F comprises the structure:

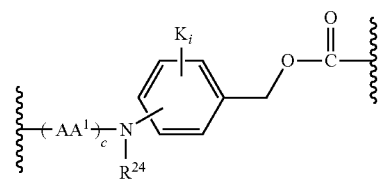

where $R^{24}$, $AA^1$, K, i, and c are as defined above.

In another embodiment, the peptide linker of formula (a) above comprises a —F-$(L^1)_m$- that comprises the structure:

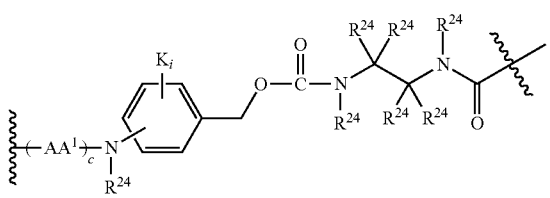

where $R^{24}$, $AA^1$, K, i, and c are as defined above.

In some embodiments, a self-immolative spacer $L^1$ or $L^2$ includes

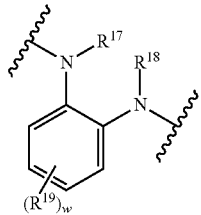

where each $R^{17}$, $R^{18}$, and $R^{19}$ is independently selected from H, substituted or unsubstituted alkyl, substituted or unsubstituted heteroalkyl and substituted or unsubstituted aryl, and w is an integer from 0 to 4. In some embodiments, $R^{17}$ and $R^{18}$ are independently H or alkyl (preferably, unsubstituted $C_1$-$C_4$ alkyl). Preferably, $R^{17}$ and $R^{18}$ are $C_{1-4}$ alkyl, such as methyl or ethyl. In some embodiments, w is 0. It has been found experimentally that this particular self-immolative spacer cyclizes relatively quickly.

In some embodiments, $L^1$ or $L^2$ includes

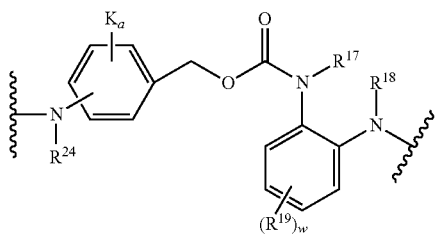

where $R^{17}$, $R^{18}$, $R^{19}$, $R^{24}$, and K are as defined above.

Spacer Groups

The spacer group $L^3$ is characterized in that it comprises a primary or secondary amine or a carboxyl functional group, and either the amine of the $L^3$ group forms an amide bond with a pendant carboxyl functional group of D or the carboxyl of $L^3$ forms an amide bond with a pendant amine functional group of D. $L^3$ can be selected from the group consisting of substituted or unsubstituted alkyl, substituted or unsubstituted heteroalkyl, substituted or unsubstituted aryl, substituted or unsubstituted heteroaryl, or substituted or unsubstituted heterocycloalkyl. In a preferred embodiment, $L^3$ comprises an aromatic group. More preferably, $L^3$ comprises a benzoic acid group, an aniline group or indole group. Non-limiting examples of structures that can serve as an -$L^3$-NH— spacer include the following structures:

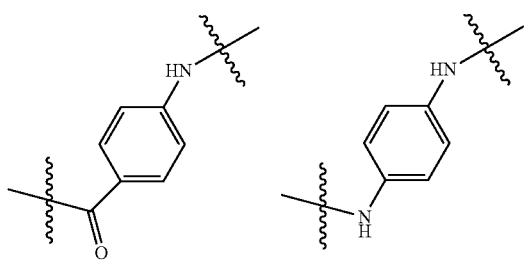

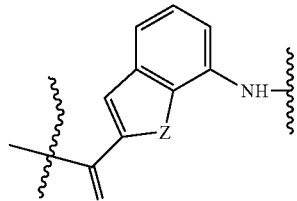

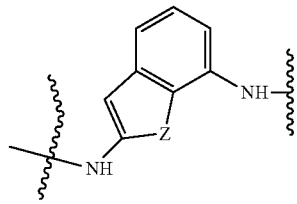

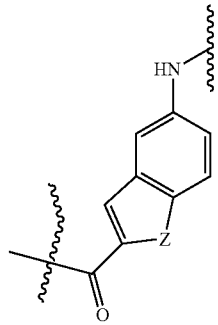
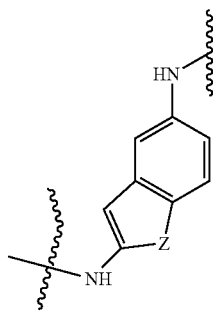

where Z is a member selected from O, S and $NR^{23}$, and where $R^{23}$ is a member selected from H, substituted or unsubstituted alkyl, substituted or unsubstituted heteroalkyl, and acyl.

Upon cleavage of the linker of the invention containing $L^3$, the $L^3$ moiety remains attached to the drug, D. Accordingly, the $L^3$ moiety is chosen such that its attachment to D does not significantly alter the activity of D. In another embodiment, a portion of the drug D itself functions as the $L^3$ spacer. For example, in one embodiment, the drug, D, is a duocarmycin derivative in which a portion of the drug functions as the $L^3$ spacer. Non-limiting examples of such embodiments include those in which $NH_2$-($L^3$)-D has a structure selected from the group consisting of:

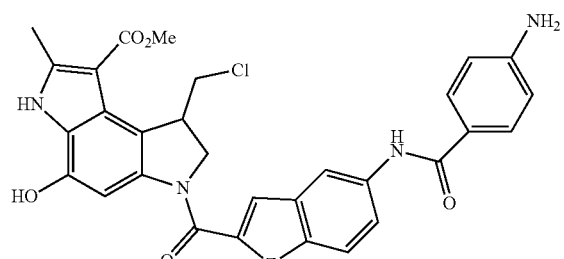

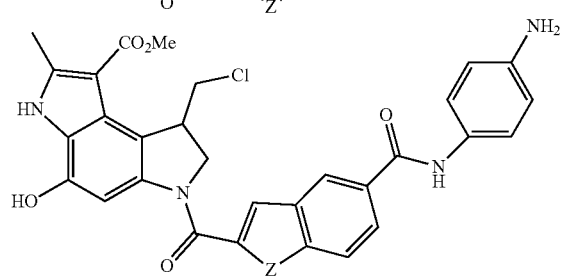

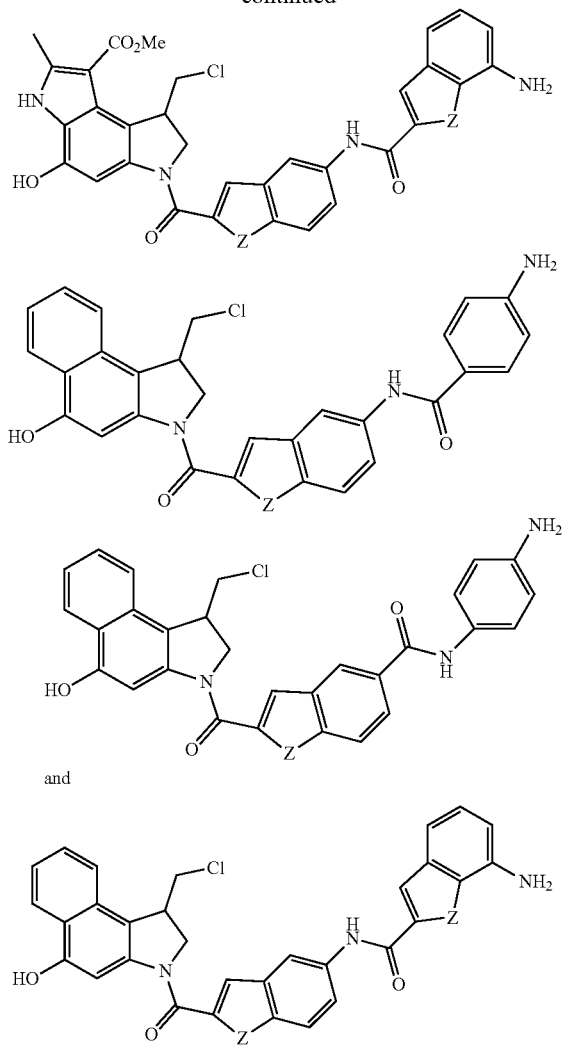

and where Z is O, S or NR$^{23}$, where R$^{23}$ is H, substituted or unsubstituted alkyl, substituted or unsubstituted heteroalkyl, or acyl; and the NH$_2$ group on each structure reacts with (AA$^1$)$_c$ to form -(AA$^1$)$_c$-NH—.

Peptide Sequence (AA$^1$)$_c$

The group AA$^1$ represents a single amino acid or a plurality of amino acids that are joined together by amide bonds. The amino acids may be natural amino acids and/or unnatural α-amino acids. They may be in the L or the D configuration. In one embodiment, at least three different amino acids are used. In another embodiment, only two amino acids are used.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, citrulline, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a precursor to arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids, and synthetically modified forms of the natural amino acids. The synthetically modified forms include, but are not limited to, amino acids having alkylene chains shortened or lengthened by up to two carbon atoms, amino acids comprising optionally substituted aryl groups, and amino acids comprised halogenated groups, preferably halogenated alkyl and aryl groups. When attached to a linker or conjugate of the invention, the amino acid is in the form of an "amino acid side chain", where the carboxylic acid group of the amino acid has been replaced with a keto (C(O)) group. Thus, for example, an alanine side chain is —C(O)—CH(NH$_2$)—CH$_3$, and so forth.

The peptide sequence (AA$^1$)$_c$ is functionally the amidification residue of a single amino acid (when c=1) or a plurality of amino acids joined together by amide bonds. The peptide sequence (AA$^1$)$_c$ preferably is selected for enzyme-catalyzed cleavage by an enzyme in a location of interest in a biological system. For example, for conjugates that are targeted to but not internalized by a cell, a peptide is chosen that is cleaved by a protease that in in the extracellular matrix, e.g., a protease released by nearby dying cells or a tumor-associated protease, such that the peptide is cleaved extracellularly. For conjugates that are designed for internalization by a cell, the sequence (AA$^1$)$_c$ preferably is selected for cleavage by an endosomal or lysosomal protease. The number of amino acids within the peptide can range from 1 to 20; but more preferably there will be 1-8 amino acids, 1-6 amino acids or 1, 2, 3 or 4 amino acids comprising (AA$^1$)$_c$. Peptide sequences that are susceptible to cleavage by specific enzymes or classes of enzymes are well known in the art.

Preferably, (AA$^1$)$_c$ contains an amino acid sequence ("cleavage recognition sequence") that is a cleavage site by the protease. Many protease cleavage sequences are known in the art. See, e.g., Matayoshi et al. Science 247: 954 (1990); Dunn et al. Meth. Enzymol. 241: 254 (1994); Seidah et al. Meth. Enzymol. 244: 175 (1994); Thornberry, Meth. Enzymol. 244: 615 (1994); Weber et al. Meth. Enzymol. 244: 595 (1994); Smith et al. Meth. Enzymol. 244: 412 (1994); Bouvier et al. Meth. Enzymol. 248: 614 (1995), Hardy et al., in Amyloid Protein Precursor in Development, Aging, and Alzheimer's Disease, ed. Masters et al. pp. 190-198 (1994).

In a preferred embodiment, the peptide sequence (AA$^1$)$_c$ is chosen based on its ability to be cleaved by a lysosomal proteases, non-limiting examples of which include cathepsins B, C, D, H, L and S. Preferably, the peptide sequence (AA$^1$)$_c$ is capable of being cleaved by cathepsin B in vitro.

In another embodiment, the peptide sequence (AA$^1$)$_c$ is chosen based on its ability to be cleaved by a tumor-associated protease, such as a protease found extracellularly in the vicinity of tumor cells, examples of which include thimet oligopeptidase (TOP) and CD10. In other embodiments, the sequence (AA$^1$)$_c$ is designed for selective cleavage by urokinase or tryptase.

Suitable, but non-limiting, examples of peptide sequences suitable for use in the conjugates of the invention include Val-Cit, Cit-Cit, Val-Lys, Phe-Lys, Lys-Lys, Ala-Lys, Phe- Cit, Leu-Cit, Ile-Cit, Trp, Cit, Phe-Ala, Phe-$N^9$-tosyl-Arg, Phe-$N^9$-nitro-Arg, Phe-Phe-Lys, D-Phe-Phe-Lys, Gly-Phe-Lys, Leu-Ala-Leu, Ile-Ala-Leu, Val-Ala-Val, Ala-Leu-Ala-Leu (SEQ. ID NO: 40), β-Ala-Leu-Ala-Leu (SEQ. ID NO: 41) and Gly-Phe-Leu-Gly (SEQ. ID NO: 42) Val-Ala, Leu-Leu-Gly-Leu (SEQ. ID NO: 43), Leu-Asn-Ala, and Lys-Leu-Val. Preferred peptides sequences are Val-Cit and Val-Lys.

In another embodiment, the amino acid located the closest to the drug moiety is selected from the group consisting of: Ala, Asn, Asp, Cit, Cys, Gln, Glu, Gly, Ile, Leu, Lys, Met, Phe, Pro, Ser, Thr, Trp, Tyr, and Val. In yet another embodiment, the amino acid located the closest to the drug moiety is selected from the group consisting of: Ala, Asn, Asp, Cys, Gln, Glu, Gly, Ile, Leu, Met, Phe, Pro, Ser, Thr, Trp, Tyr, and Val.

One of skill in the art can readily evaluate an array of peptide sequences to determine their utility in the present invention without resort to undue experimentation. See, for example, Zimmerman, M., et al., (1977) *Analytical Biochemistry* 78:47-51; Lee, D., et al., (1999) *Bioorganic and Medicinal Chemistry Letters* 9:1667-72; and Rano, T. A., et al., (1997) *Chemistry and Biology* 4:149-55.

A conjugate of this invention may optionally contain two or more linkers. These linkers may be the same or different. For example, a peptidyl linker may be used to connect the drug to the ligand and a second peptidyl linker may attach a diagnostic agent to the complex. Other uses for additional linkers include linking analytical agents, biomolecules, targeting agents, and detectable labels to the antibody-partner complex.

Hydrazine Linkers (H)

In another embodiment, the conjugate of the invention comprises a hydrazine self-immolative linker, wherein the conjugate has the structure:

$$X^4\text{-}(L^4)_p\text{-}H\text{-}(L^1)_m\text{-}D$$

wherein D, $L^1$, $L^4$, p, m, and $X^4$ are as defined above and described further herein, and H is a linker comprising the structure:

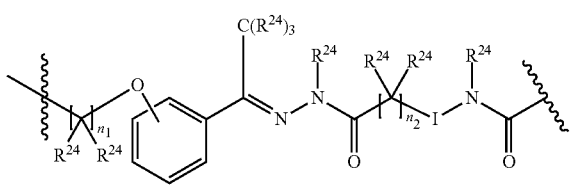

wherein $n_1$ is an integer from 1-10; $n_2$ is 0, 1, or 2; each $R^{24}$ is a member independently selected from the group consisting of H, substituted alkyl, unsubstituted alkyl, substituted heteroalkyl, and unsubstituted heteroalkyl; and I is either a bond (i.e., the bond between the carbon of the backbone and the adjacent nitrogen) or:

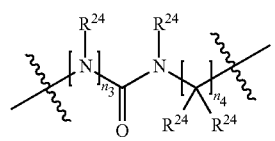

wherein $n_3$ is 0 or 1, with the proviso that when $n_3$ is 0, $n_2$ is not 0; and $n_4$ is 1, 2, or 3.

In one embodiment, the substitution on the phenyl ring is a para substitution. In preferred embodiments, $n_1$ is 2, 3, or 4 or $n_1$ is 3. In preferred embodiments, $n_2$ is 1. In preferred embodiments, I is a bond (i.e., the bond between the carbon of the backbone and the adjacent nitrogen). In one aspect, the hydrazine linker, H, can form a 6-membered self immolative linker upon cleavage, for example, when $n_3$ is 0 and $n_4$ is 2. In another aspect, the hydrazine linker, H, can form two 5-membered self immolative linkers upon cleavage. In yet other aspects, H forms a 5-membered self immolative linker, H forms a 7-membered self immolative linker, or H forms a 5-membered self immolative linker and a 6-membered self immolative linker, upon cleavage. The rate of cleavage is affected by the size of the ring formed upon cleavage. Thus, depending upon the rate of cleavage desired, an appropriate size ring to be formed upon cleavage can be selected.

Another hydrazine structure, H, has the formula:

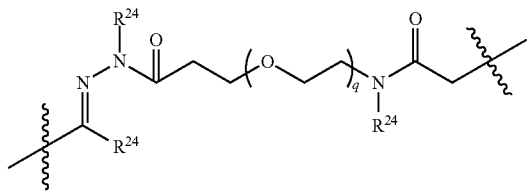

where q is 0, 1, 2, 3, 4, 5, or 6; and each $R^{24}$ is a member independently selected from the group consisting of H, substituted alkyl, unsubstituted alkyl, substituted heteroalkyl, and unsubstituted heteroalkyl. This hydrazine structure can also form five-, six-, or seven-membered rings and additional components can be added to form multiple rings.

The preparation, cleavage chemistry and cyclization kinetics of the various hydrazine linkers is disclosed in WO 2005/112919, the disclosure of which is incorporated herein by reference.

Disulfide Linkers (J)

In yet another embodiment, the linker comprises an enzymatically cleavable disulfide group. In one embodiment, the invention provides a cytotoxic antibody-partner compound having a structure according to Formula (d):

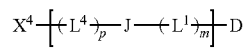

wherein D, $L^1$, $L^4$, p, m, and $X^4$ are as defined above and described further herein, and J is a disulfide linker comprising a group having the structure:

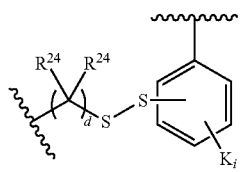

wherein each $R^{24}$ is a member independently selected from the group consisting of H, substituted alkyl, unsubstituted alkyl, substituted heteroalkyl, and unsubstituted heteroalkyl; each K is a member independently selected from the group consisting of substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl, unsubstituted heterocycloalkyl, halogen, $NO_2$, $NR^{21}R^{22}$, $NR^{21}COR^{22}$, $OCONR^{21}R^{22}$, $OCOR^{21}$, and $OR^{21}$ wherein $R^{21}$ and $R^{22}$ are independently selected from the group consisting of H, substituted alkyl, unsubstituted alkyl, substituted heteroalkyl, unsubstituted heteroalkyl, substituted aryl, unsubstituted aryl, substituted heteroaryl, unsubstituted heteroaryl, substituted heterocycloalkyl and unsubstituted heterocycloalkyl; i is an integer of 0, 1, 2, 3, or 4; and d is an integer of 0, 1, 2, 3, 4, 5, or 6.

The aromatic ring of a disulfides linker can be substituted with one or more "K" groups. A "K" group is a substituent on the aromatic ring that replaces a hydrogen otherwise attached to one of the four non-substituted carbons that are part of the ring structure. The "K" group may be a single atom, such as a halogen, or may be a multi-atom group, such as alkyl, heteroalkyl, amino, nitro, hydroxy, alkoxy, haloalkyl, and cyano. Exemplary K substituents independently include, but are not limited to, F, Cl, Br, I, $NO_2$, OH, $OCH_3$, $NHCOCH_3$, $N(CH_3)_2$, $NHCOCF_3$ and methyl. For "$K_i$", i is an integer of 0, 1, 2, 3, or 4. In a specific embodiment, i is 0.

In a preferred embodiment, the linker comprises an enzymatically cleavable disulfide group of the following formula:

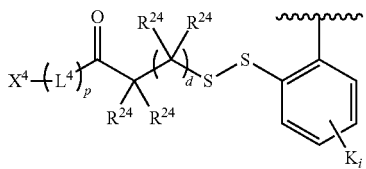

wherein $L^4$, $X^4$, p, and $R^{24}$ are as described above, and d is 0, 1, 2, 3, 4, 5, or 6. In a particular embodiment, d is 1 or 2.

A more specific disulfide linker is shown in the formula below:

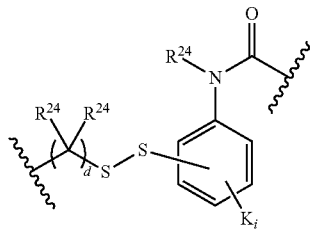

Preferably, d is 1 or 2 and each K is H.
Another disulfide linker is shown in the formula below:

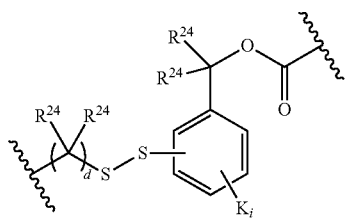

Preferably, d is 1 or 2 and each K is H.
In various embodiments, the disulfides are ortho to the amine. In another specific embodiment, a is 0. In preferred embodiments, $R^{24}$ is independently selected from H and $CH_3$.

The preparation and chemistry of disulfide linkers such as those described above is disclosed in WO 2005/112919, the disclosure of which is incorporated herein by reference.

For further discussion of types of cytotoxins, linkers and other methods for conjugating therapeutic agents to antibodies, see also U.S. Pat. No. 7,087,600; U.S. Pat. No. 6,989,452; U.S. Pat. No. 7,129,261; US 2006/0004081; US 2006/0247295; WO 02/096910; WO 2007/051081; WO 2005/112919; WO 2007/059404; WO 2008/083312; PCT application no. PCT/US2008/054362; Saito et al. (2003) Adv. Drug Deliv. Rev. 55:199-215; Trail et al. (2003) Cancer Immunol. Immunother. 52:328-337; Payne. (2003) Cancer Cell 3:207-212; Allen (2002) Nat. Rev. Cancer 2:750-763; Pastan and Kreitman (2002) Curr. Opin. Investig. Drugs 3:1089-1091; Senter and Springer (2001) Adv. Drug Deliv. Rev. 53:247-264, each of which is hereby incorporated by reference in its entirety.

Cytotoxins as Partner Molecules

In one aspect, the present invention features an antibody conjugated to a partner molecule, such as a cytotoxin, a drug (e.g., an immunosuppressant) or a radiotoxin. Such conjugates are also referred to as "immunotoxins." A cytotoxin or cytotoxic agent includes any agent that is detrimental to (e.g., kills) cells.

Examples of partner molecules of the present invention include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Examples of partner molecules also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, tubulysin, dibromomannitol, streptozotocin, mitomycin C, cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other preferred examples of partner molecules that can be conjugated to an antibody of the invention include calicheamicins, maytansines and auristatins, and derivatives thereof.

Preferred examples of partner molecule are analogs and derivatives of CC-1065 and the structurally related duocarmycins. Despite its potent and broad antitumor activity, CC-1065 cannot be used in humans because it causes delayed death in experimental animals, prompting a search for analogs or derivatives with a better therapeutic index.

Many analogues and derivatives of CC-1065 and the duocarmycins are known in the art. The research into the structure, synthesis and properties of many of the compounds has been reviewed. See, for example, Boger et al., Angew. Chem. Int. Ed. Engl. 35: 1438 (1996); and Boger et al., Chem. Rev. 97: 787 (1997). Other disclosures relating to CC-1065 analogs or derivatives include: U.S. Pat. No. 5,101,038; U.S. Pat. No. 5,641,780; U.S. Pat. No. 5,187,186; U.S. Pat. No. 5,070,092; U.S. Pat. No. 5,703,080; U.S. Pat. No. 5,070,092; U.S. Pat. No. 5,641,780; U.S. Pat. No. 5,101,038; U.S. Pat. No. 5,084,468; U.S. Pat. No. 5,739,350; U.S. Pat. No. 4,978,757, U.S. Pat. No. 5,332,837 and U.S. Pat. No. 4,912,227; WO 96/10405; and EP 0,537,575 A1

In a particularly preferred aspect, the partner molecule is a CC-1065/duocarmycin analog having a structure according to the following formula (e):

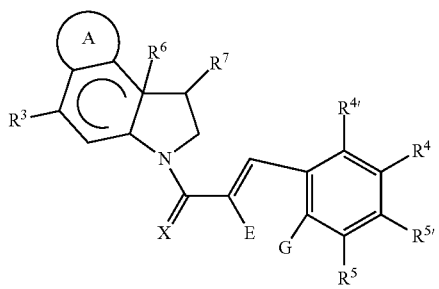

(e)

in which ring system A is a member selected from substituted or unsubstituted aryl substituted or unsubstituted heteroaryl and substituted or unsubstituted heterocycloalkyl groups. Exemplary ring systems A include phenyl and pyrrole.

The symbols E and G are independently selected from H, substituted or unsubstituted alkyl, substituted or unsubstituted heteroalkyl, a heteroatom, a single bond or E and G are optionally joined to form a ring system selected from substituted or unsubstituted aryl, substituted or unsubstituted heteroaryl and substituted or unsubstituted heterocycloalkyl.

The symbol X represents a member selected from O, S and $NR^{23}$. $R^{23}$ is a member selected from H, substituted or unsubstituted alkyl, substituted or unsubstituted heteroalkyl, and acyl.

The symbol $R^3$ represents a member selected from (=O), $SR^{11}$, $NHR^{11}$ and $OR^{11}$, in which $R^{11}$ is H, substituted or unsubstituted alkyl, substituted or unsubstituted heteroalkyl, monophosphates, diphosphates, triphosphates, sulfonates, acyl, $C(O)R^{12}R^{13}$, $C(O)OR^{12}$, $C(O)NR^{12}R^{13}$, $P(O)(OR^{12})_2$, $C(O)CHR^{12}R^{13}$, $SR^{12}$ or $SiR^{12}R^{13}R^{14}$. The symbols $R^{12}$, $R^{13}$, and $R^{14}$ independently represent H, substituted or unsubstituted alkyl, substituted or unsubstituted heteroalkyl and substituted or unsubstituted aryl, where $R^{12}$ and $R^{13}$ together with the nitrogen or carbon atom to which they are attached are optionally joined to form a substituted or unsubstituted heterocycloalkyl ring system having from 4 to 6 members, optionally containing two or more heteroatoms.

$R^4$, $R^{4'}$, $R^5$ and $R^{5'}$ are members independently selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}$=$NR^{16}$, and $O(CH_2)_nN(CH_3)_2$, where n is an integer from 1 to 20, or any adjacent pair of $R^4$, $R^{4'}$, $R^5$ and $R^{5'}$, together with the carbon atoms to which they are attached, are joined to form a substituted or unsubstituted cycloalkyl or heterocycloalkyl ring system having from 4 to 6 members. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms. One exemplary structure is aniline.

One of $R^3$, $R^4$, $R^{4'}$, $R^5$, and $R^{5'}$ joins the cytotoxin to a linker or enzyme cleavable substrate of the present invention, as described herein, for example to $L^1$ or $L^3$, if present or to F, H, or J.

$R^6$ is a single bond which is either present or absent. When $R^6$ is present, $R^6$ and $R^7$ are joined to form a cyclopropyl ring.

$R^7$ is $CH_2$—$X^1$ or —$CH_2$—. When $R^7$ is —$CH_2$— it is a component of the cyclopropane ring. The symbol $X^1$ represents a leaving group such as a halogen, for example Cl, Br or F. The combinations of $R^6$ and $R^7$ are interpreted in a manner that does not violate the principles of chemical valence.

$X^1$ may be any leaving group. Useful leaving groups include, but are not limited to, halogens, azides, sulfonic esters (e.g., alkylsulfonyl, arylsulfonyl), oxonium ions, alkyl perchlorates, ammonioalkanesulfonate esters, alkylfluorosulfonates and fluorinated compounds (e.g., triflates, nonaflates, tresylates) and the like. Particular halogens useful as leaving groups are F, Cl and Br.

The curved line within the six-membered ring indicates that the ring may have one or more degrees of unsaturation, and it may be aromatic. Thus, ring structures such as those set forth below, and related structures, are within the scope of Formula (f):

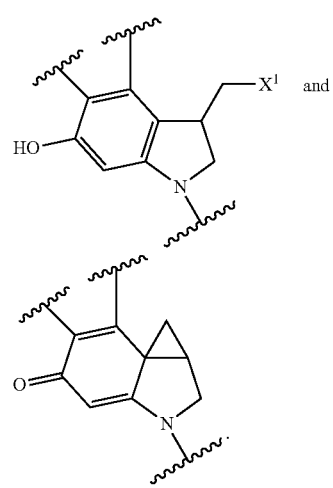

(f)

In one embodiment, $R^{11}$ includes a moiety, $X^5$, that does not self-cyclize and links the drug to $L^1$ or $L^3$, if present, or to F, H, or J. The moiety, $X^5$, is preferably cleavable using an enzyme and, when cleaved, provides the active drug. As an example, $R^{11}$ can have the following structure (with the right side coupling to the remainder of the drug):

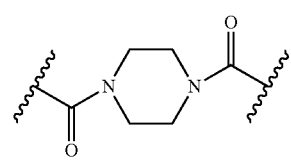 [SMILES: *C(=O)N1CCN(C(*)=O)CC1]

In some embodiments, at least one of $R^4$, $R^{4'}$, $R^5$, and $R^{5'}$ links said drug to $L^1$, if present, or to F, H, J, or $X^2$, and $R^3$ is selected from $SR^{11}$, $NHR^{11}$ and $OR^{11}$. $R^{11}$ is selected from —$SO(OH)_2$, —$PO(OH)_2$, -$AA_n$, —$Si(CH_3)_2C(CH_3)_3$, —$C(O)OPhNH(AA)_m$,

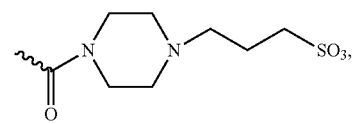

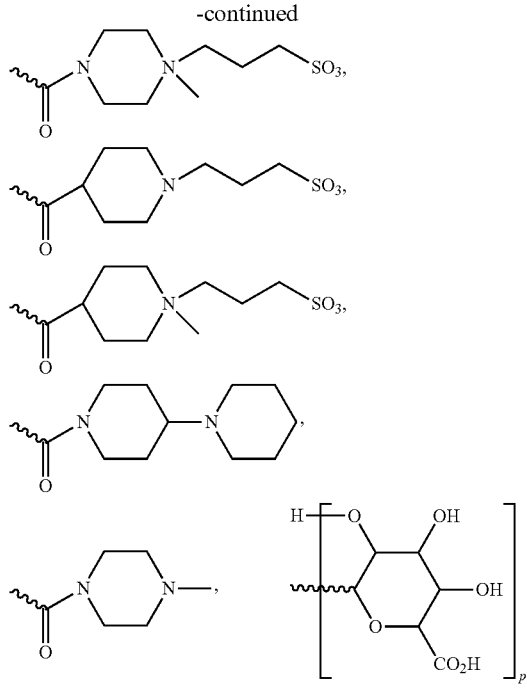

or any other sugar or combination of sugars

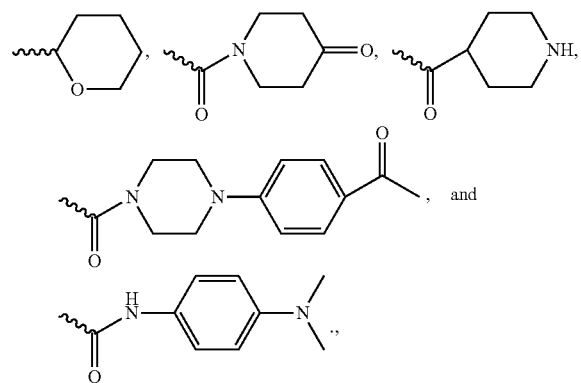

and pharmaceutically acceptable salts thereof, where n is any integer in the range of 1 to 10, m is any integer in the range of 1 to 4, is any integer in the range of 1 to 6, and AA is any natural or non-natural amino acid. Where the compound of formula (e) is conjugated via $R^4$, $R^{4\prime}$, $R^5$, or $R^6$, $R^3$ preferably comprises a cleavable blocking group whose presence blocks the cytotoxic activity of the compound but is cleavable under conditions found at the intended site of action by a mechanism different from that for cleavage of the linker conjugating the cytotoxin to the antibody. In this way, if there is adventitiouis cleavage of the conjugate in the plasma, the blocking group attenuates the cytotoxicity of the released cytotoxin. For instance, if the conjugate has a hydrazone or disulfide linker, the blocking group can be an enzymatically cleavable amide. Or, if the linker is a peptidyl one cleavable by a protease, the blocking group can be an ester or carbamate cleavable by a carboxyesterase.

For example, in a preferred embodiment, D is a cytotoxin having a structure (j):

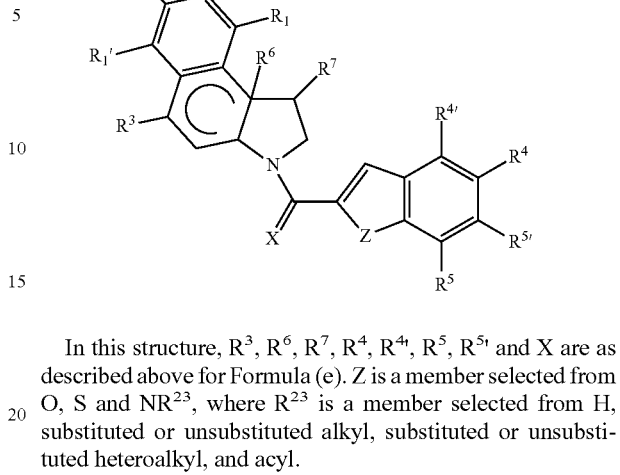

In this structure, $R^3$, $R^6$, $R^7$, $R^4$, $R^{4\prime}$, $R^5$, $R^{5\prime}$ and X are as described above for Formula (e). Z is a member selected from O, S and $NR^{23}$, where $R^{23}$ is a member selected from H, substituted or unsubstituted alkyl, substituted or unsubstituted heteroalkyl, and acyl.

$R^1$ is H, substituted or unsubstituted lower alkyl, $C(O)R^8$, or $CO_2R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl.

$R^{1\prime}$ is H, substituted or unsubstituted lower alkyl, or $C(O)R^8$, wherein $R^8$ is a member selected from $NR^9R^{10}$ and $OR^9$, in which $R^9$ and $R^{10}$ are members independently selected from H, substituted or unsubstituted alkyl and substituted or unsubstituted heteroalkyl.

$R^2$ is H, or substituted or unsubstituted lower alkyl or unsubstituted heteroalkyl or cyano or alkoxy; and $R^{2\prime}$ is H, or substituted or unsubstituted lower alkyl or unsubstituted heteroalkyl.

One of $R^3$, $R^4$, $R^{4\prime}$, $R^5$, or $R^{5\prime}$ links the cytotoxin to $L^1$ or $L^3$, if present, or to F, H, or.

A further embodiment has the formula:

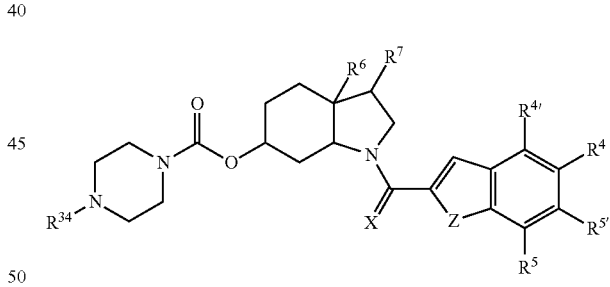

In this structure, A, $R^6$, $R^7$, X, $R^4$, $R^{4\prime}$, $R^5$, and $R^{5\prime}$ are as described above for Formula (e). Z is a member selected from O, S and $NR^{23}$, where $R^{23}$ is a member selected from H, substituted or unsubstituted alkyl, substituted or unsubstituted heteroalkyl, and acyl;

$R^{34}$ is $C(=O)R^{33}$ or $C_1$-$C_6$ alkyl, where $R^{33}$ is selected from H, substituted or unsubstituted alkyl, substituted or unsubstituted aryl, substituted or unsubstituted heteroaryl, substituted or unsubstituted heterocycloalkyl, halogen, $NO_2$, $NR^{15}R^{16}$, $NC(O)R^{15}$, $OC(O)NR^{15}R^{16}$, $OC(O)OR^{15}$, $C(O)R^{15}$, $SR^{15}$, $OR^{15}$, $CR^{15}=NR^{16}$, and $O(CH_2)_nN(CH_3)_2$, where n is an integer from 1 to 20. $R^{15}$ and $R^{16}$ independently represent H, substituted or unsubstituted alkyl, substituted or unsubstituted heteroalkyl, substituted or unsubstituted aryl, substituted or unsubstituted heteroaryl, substituted or unsubstituted heterocycloalkyl and substituted or unsubstituted peptidyl, where $R^{15}$ and $R^{16}$ together with the nitrogen atom to which they are attached are optionally joined to form a substituted or unsubstituted heterocycloalkyl ring system having from 4 to 6 members, optionally containing two or more heteroatoms.

Preferably, A is substituted or unsubstituted phenyl or substituted or unsubstituted pyrrole. Moreover, any selection of substituents described herein for $R^{11}$ is also applicable to $R^{33}$.

Markers as Partner Molecules

Where the partner molecule is a marker, it can be any moiety having or generating a detectable physical or chemical property, thereby indicating its presence in a particular tissue or cell. Markers (sometimes also called reporter groups) have been well developed in the area of immunoassays, biomedical research, and medical diagnosis. A marker may be detected by spectroscopic, photochemical, biochemical, immunochemical, electrical, optical or chemical means. Examples include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The marker is preferably a member selected from the group consisting of radioactive isotopes, fluorescent agents, fluorescent agent precursors, chromophores, enzymes and combinations thereof. Examples of suitable enzymes are horseradish peroxidase, alkaline phosphatase, β-galactosidase, and glucose oxidase. Fluorescent agents include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Markers can be attached by indirect means: a ligand molecule (e.g., biotin) is covalently bound to an antibody. The ligand then binds to another molecule (e.g., streptavidin), which is either inherently detectable or covalently bound to a signal system, such as a detectable enzyme, a fluorescent compound, or a chemiluminescent compound.

Examples of Conjugates

Specific examples of partner molecule-linker combinations suitable for conjugation to an antibody of this invention are shown following:

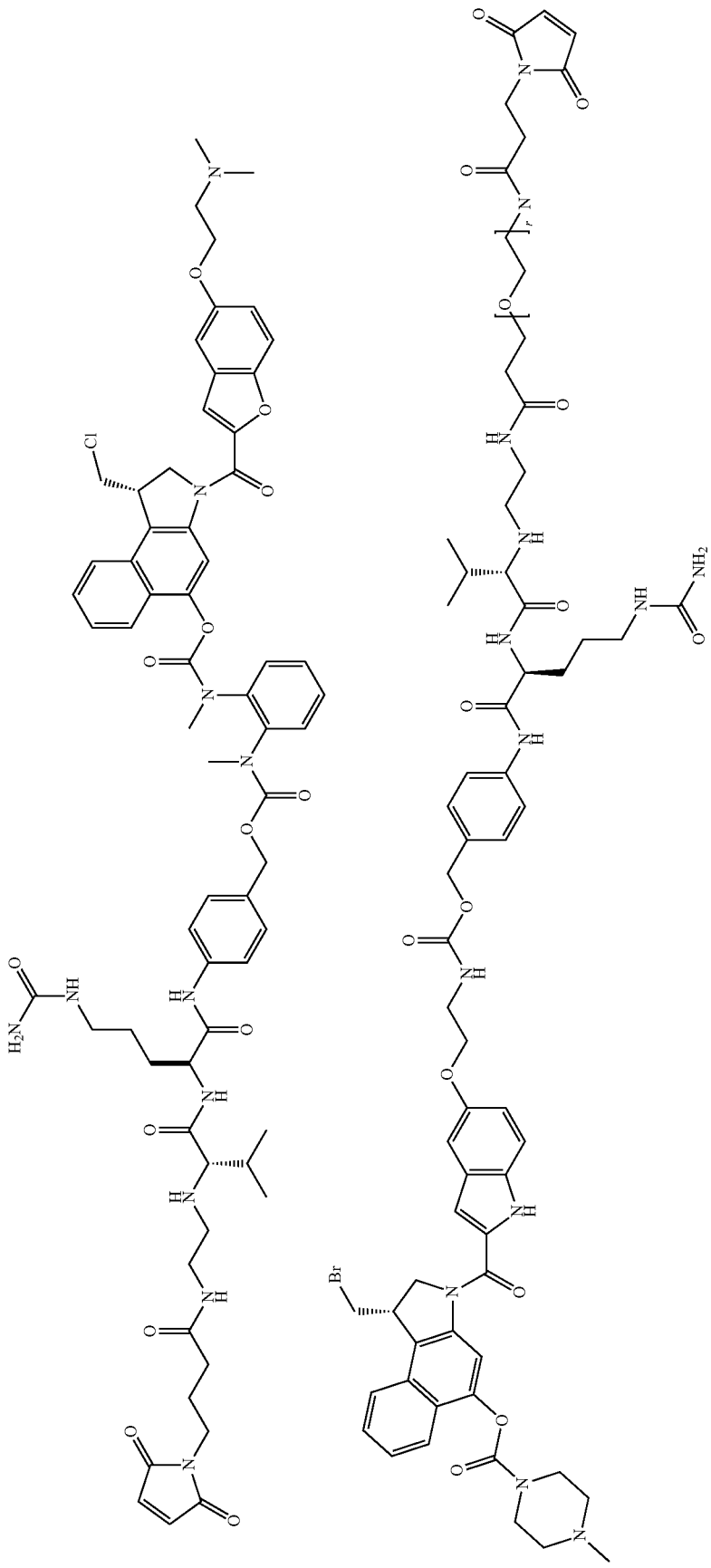

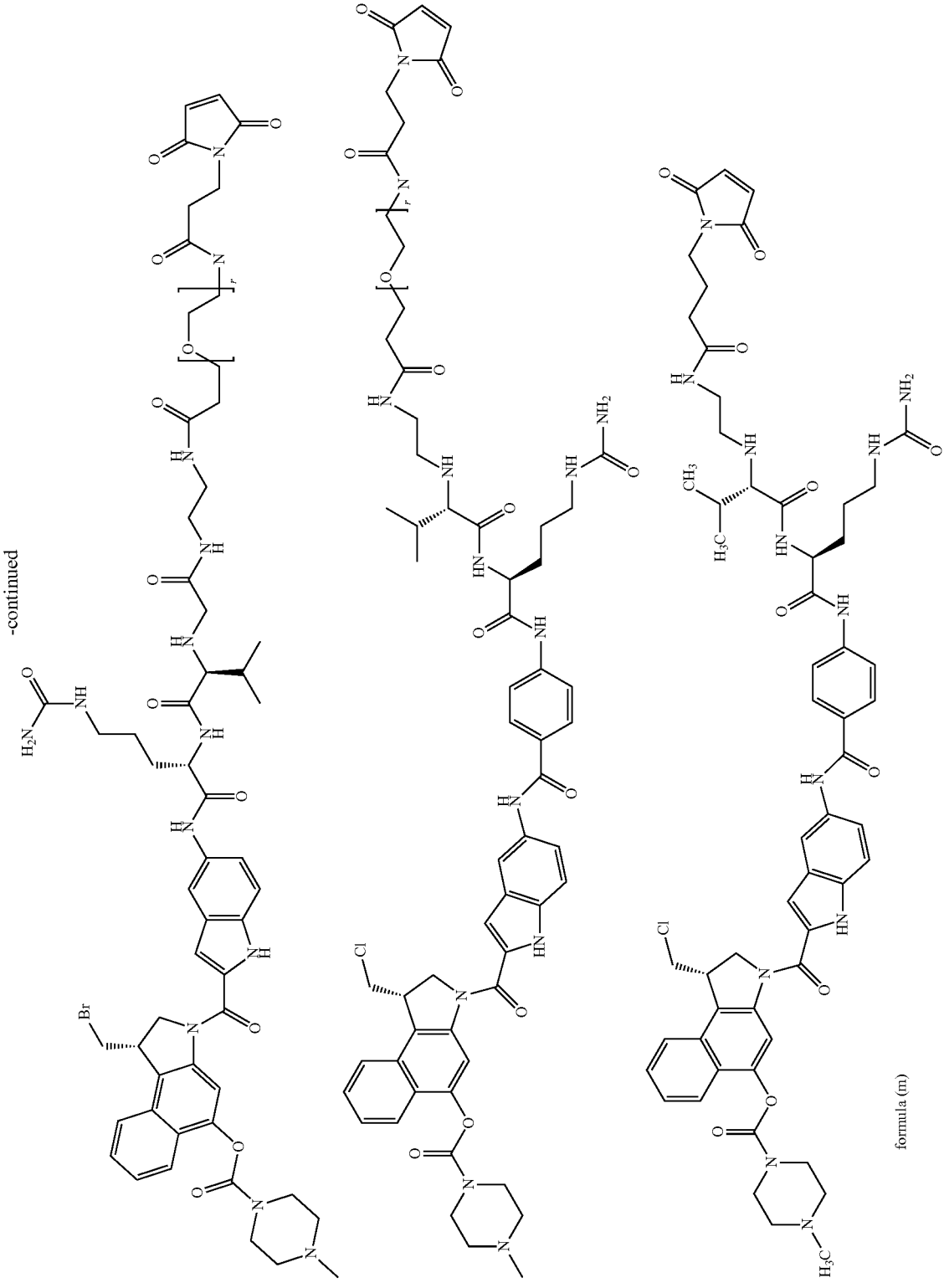
formula (m)

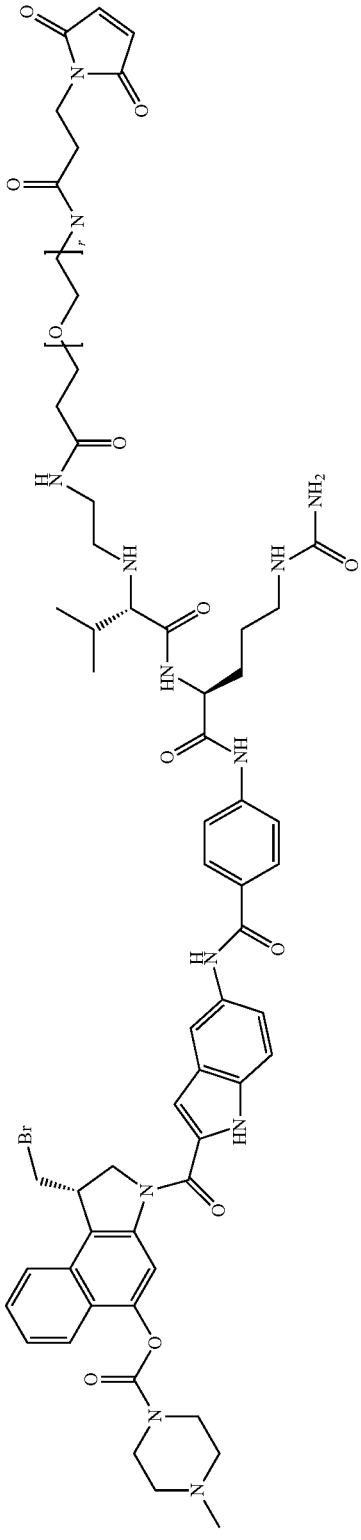
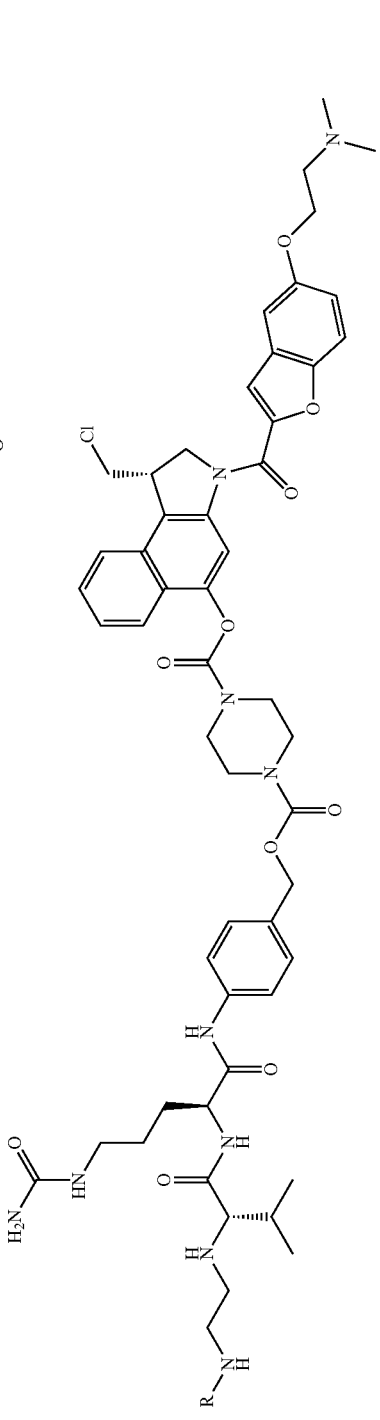
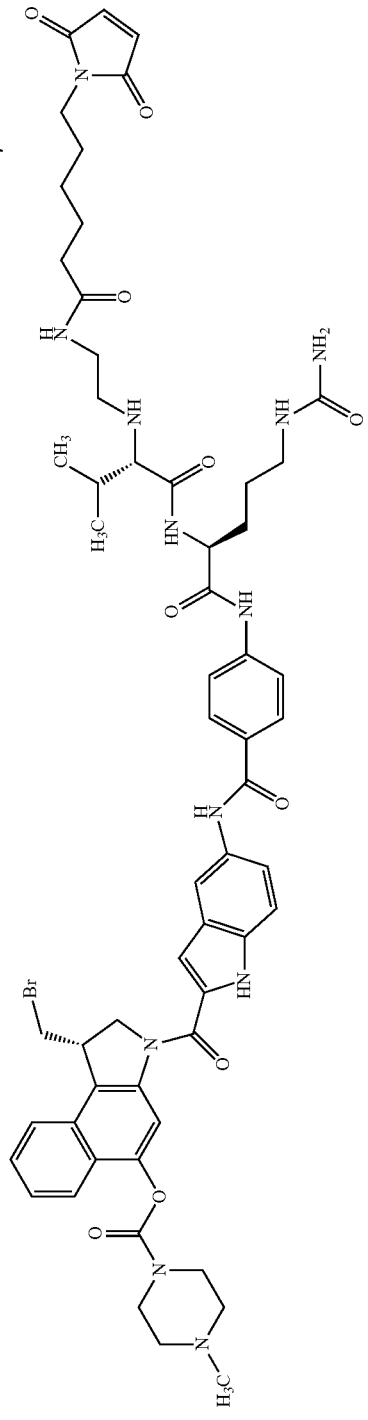

-continued
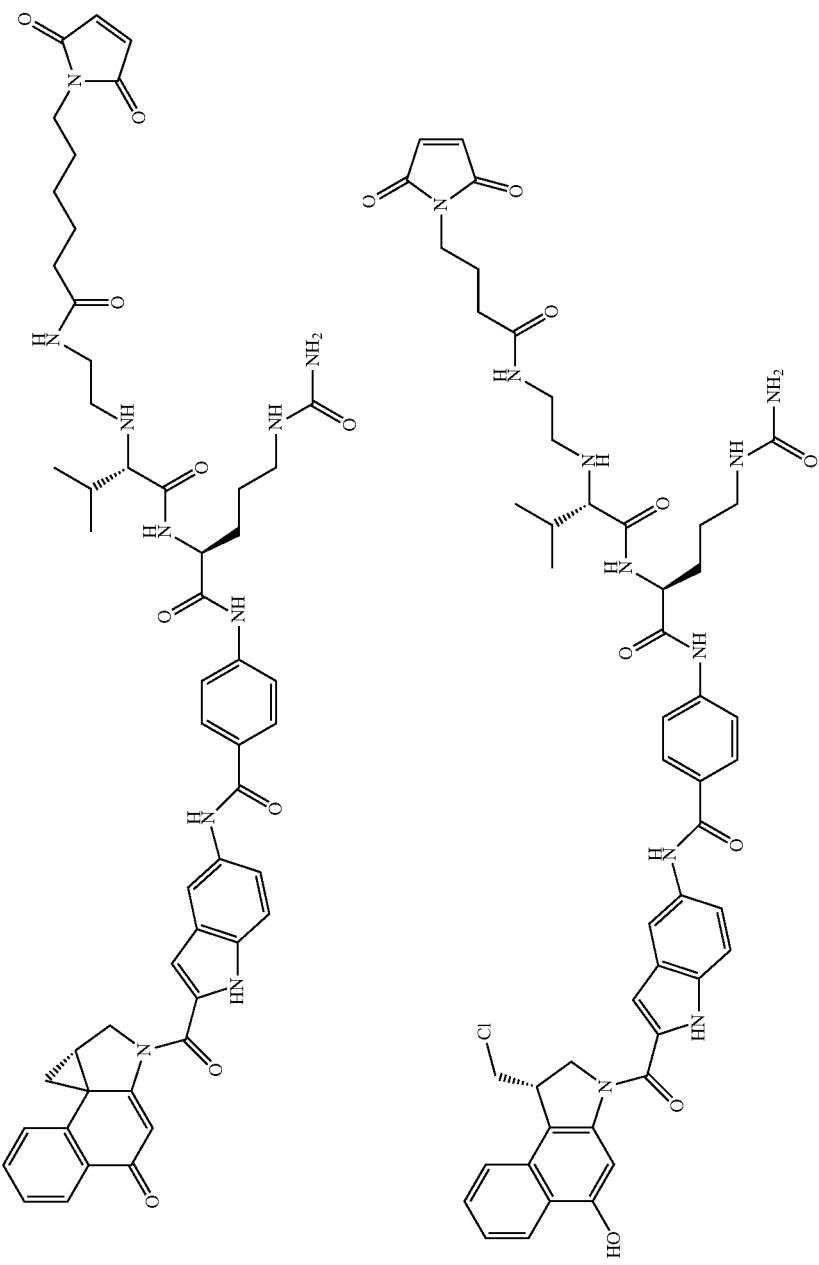

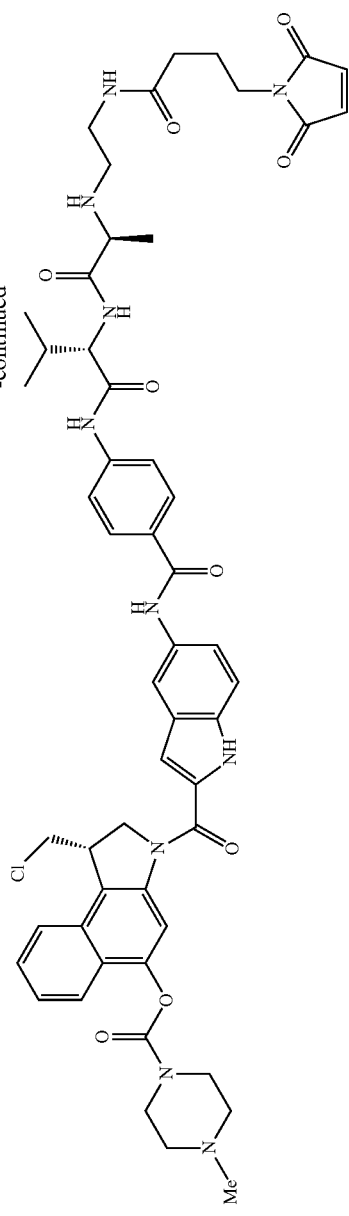
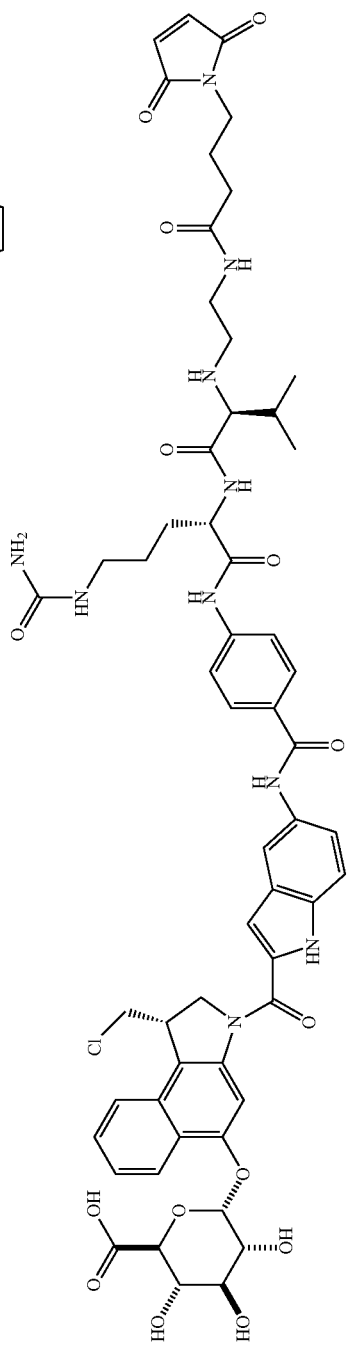
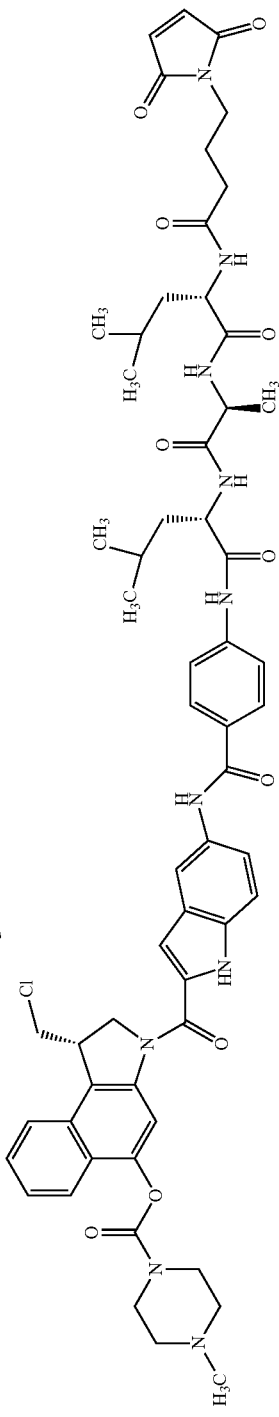

-continued
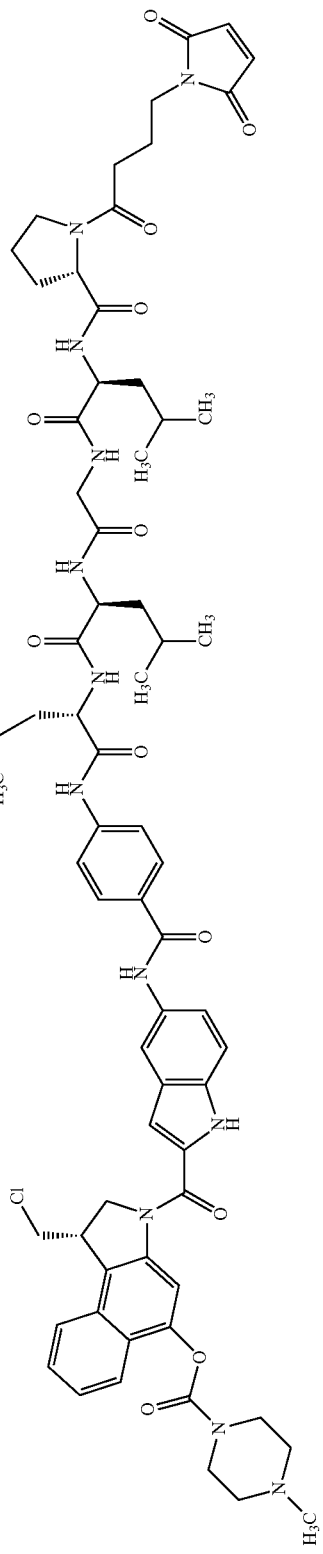
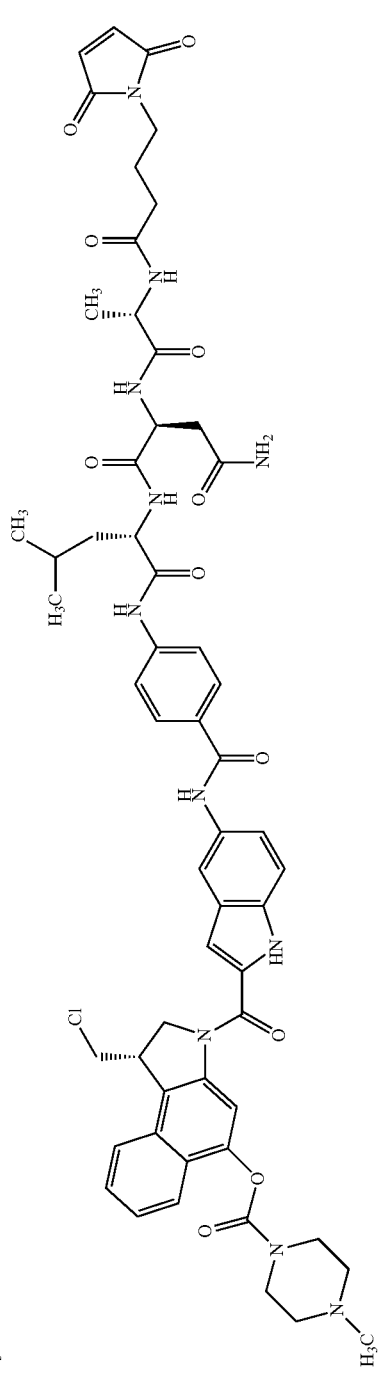

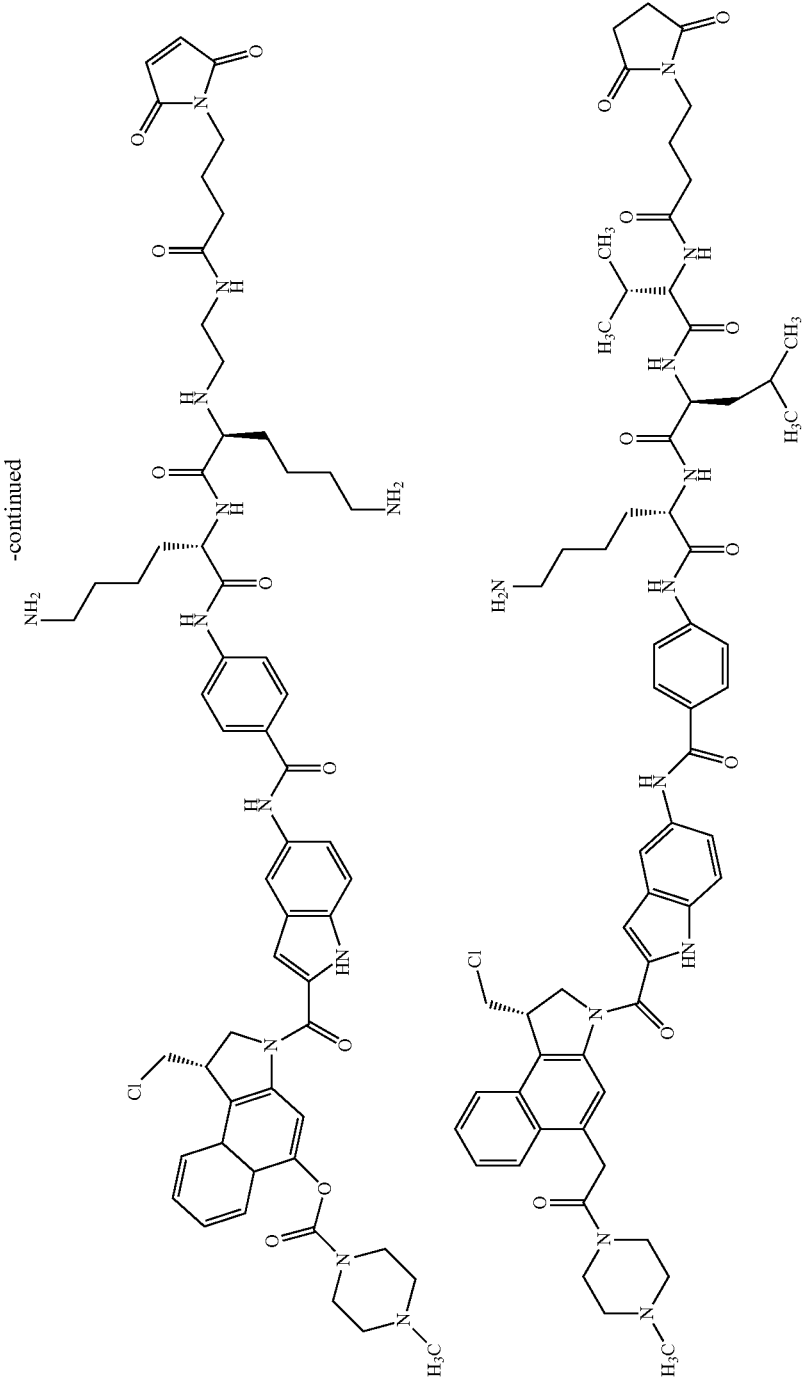

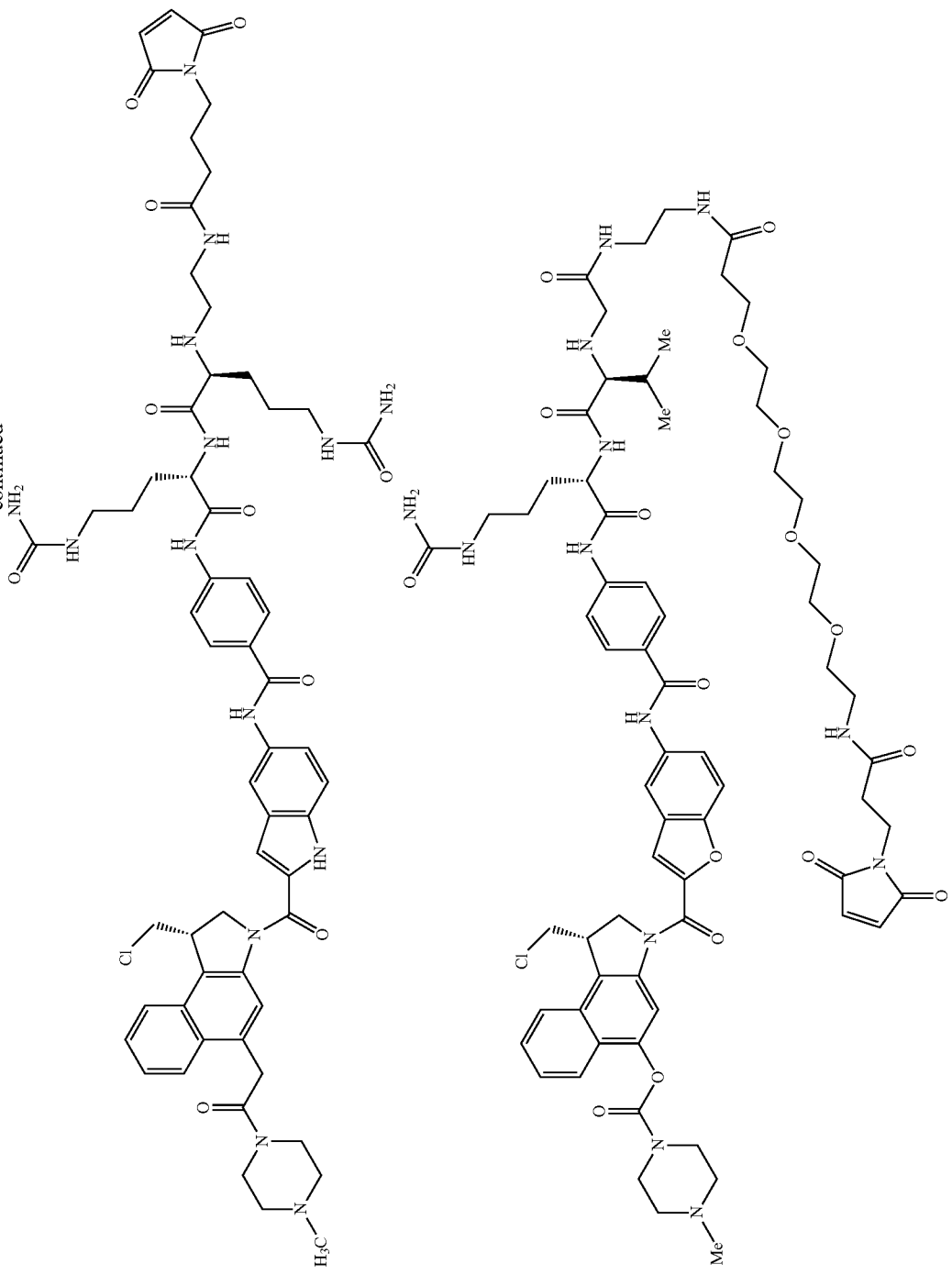

-continued
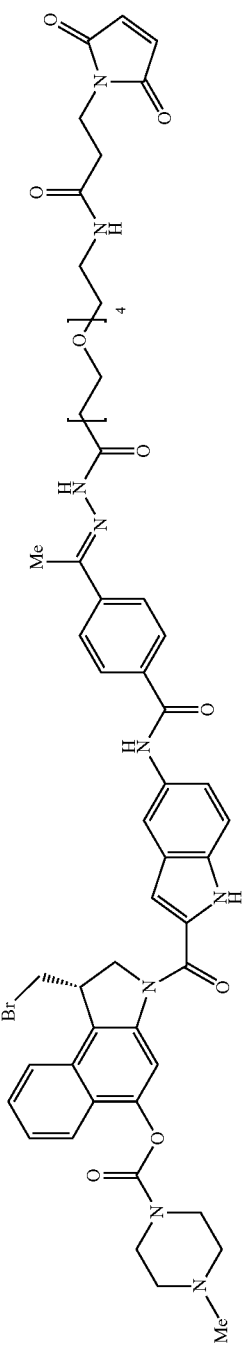
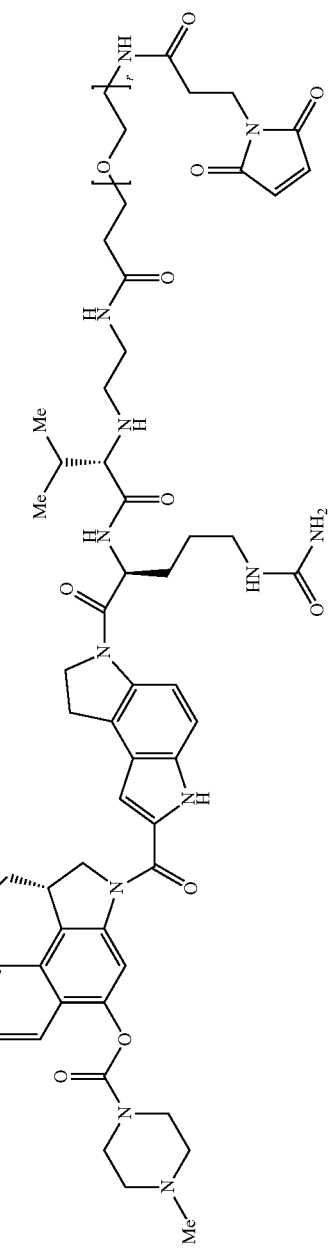
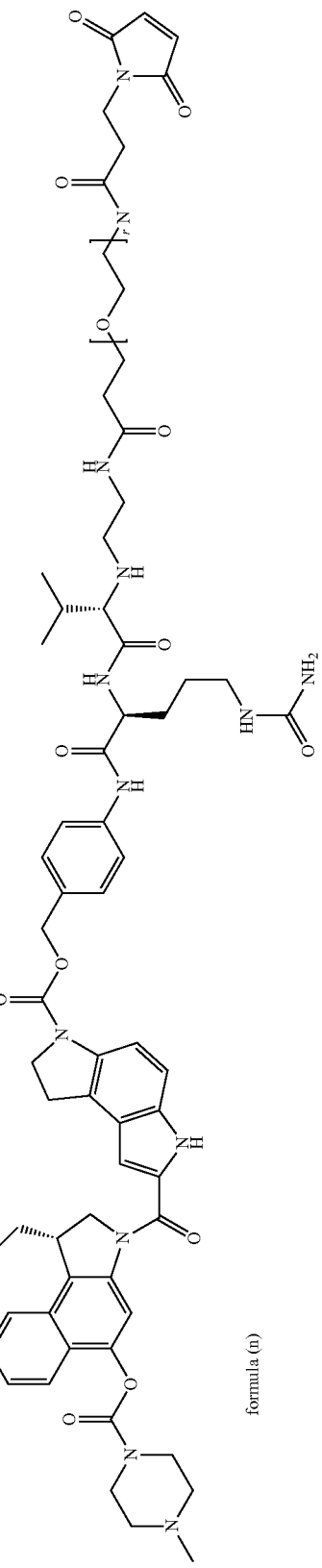
formula (n)

-continued
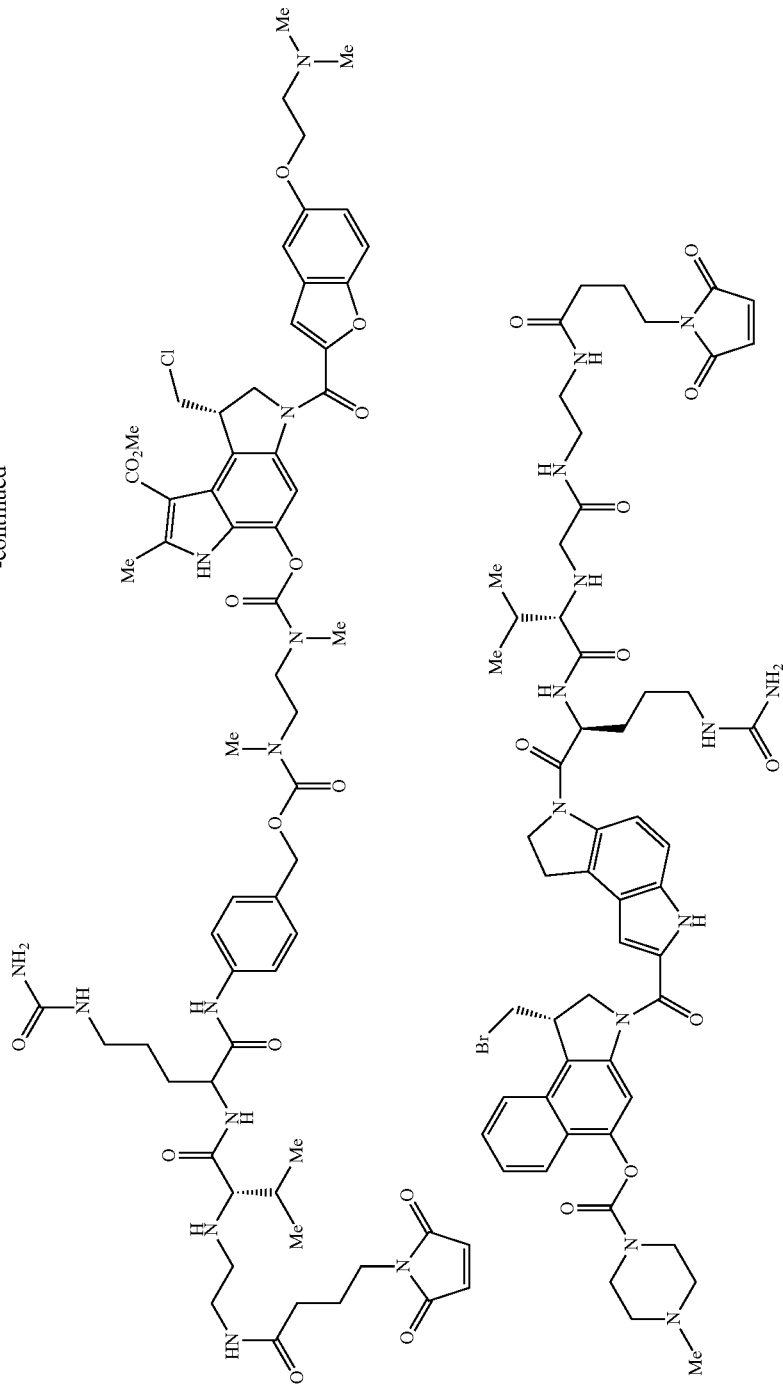

-continued
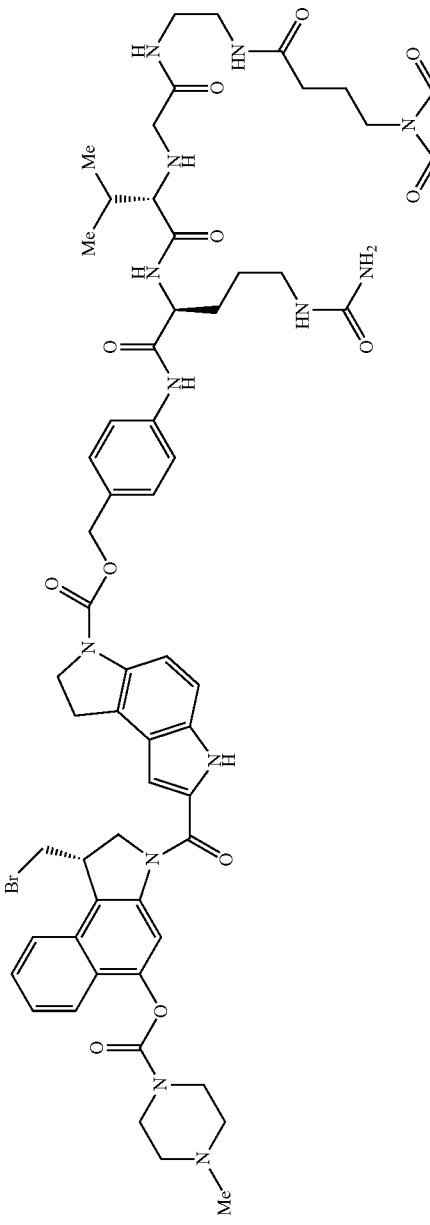 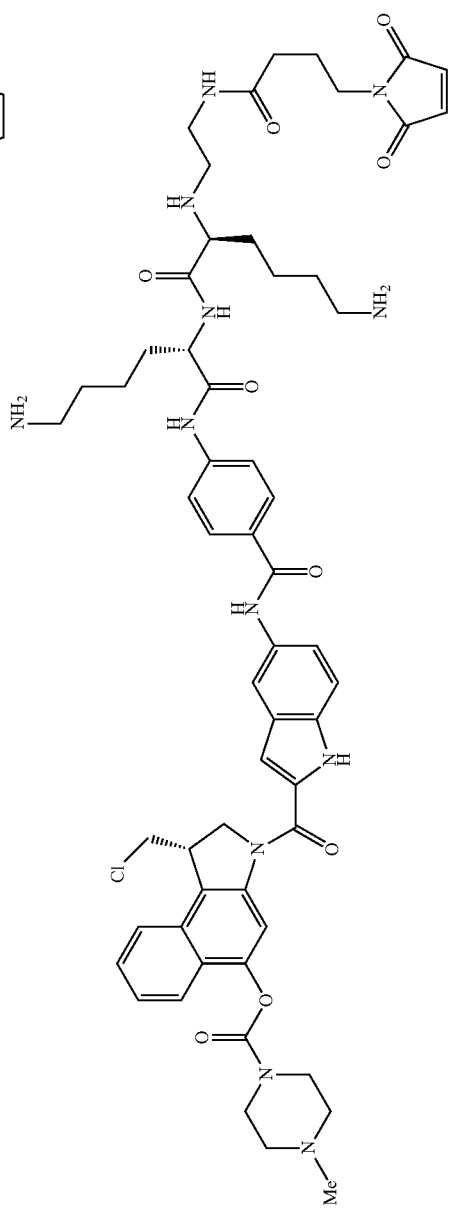

-continued
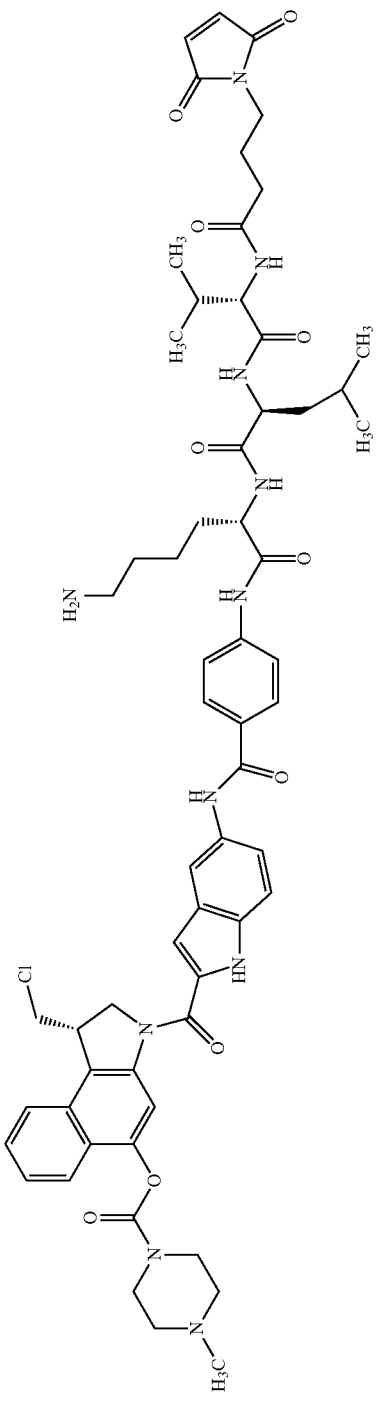
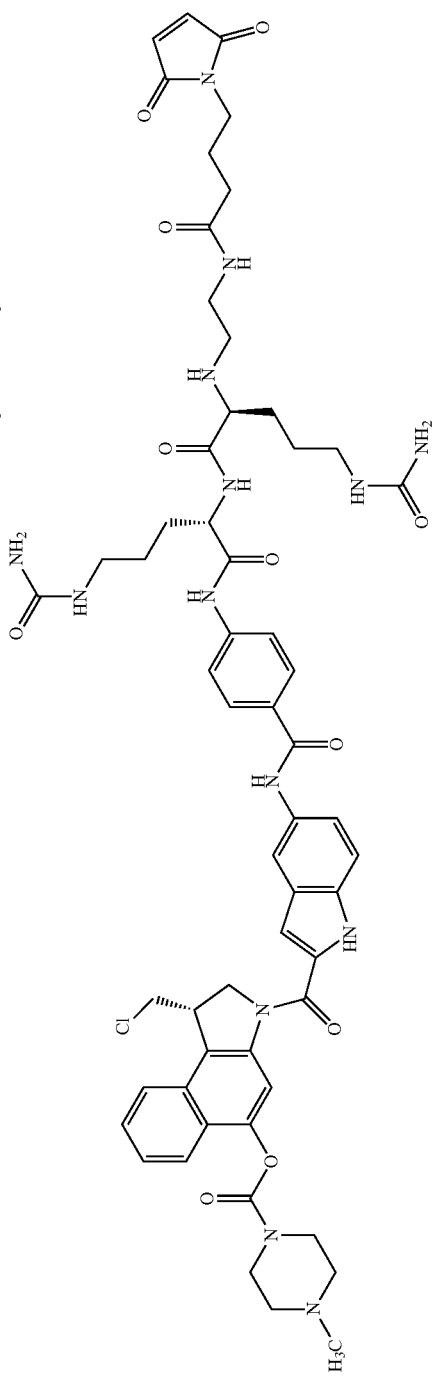

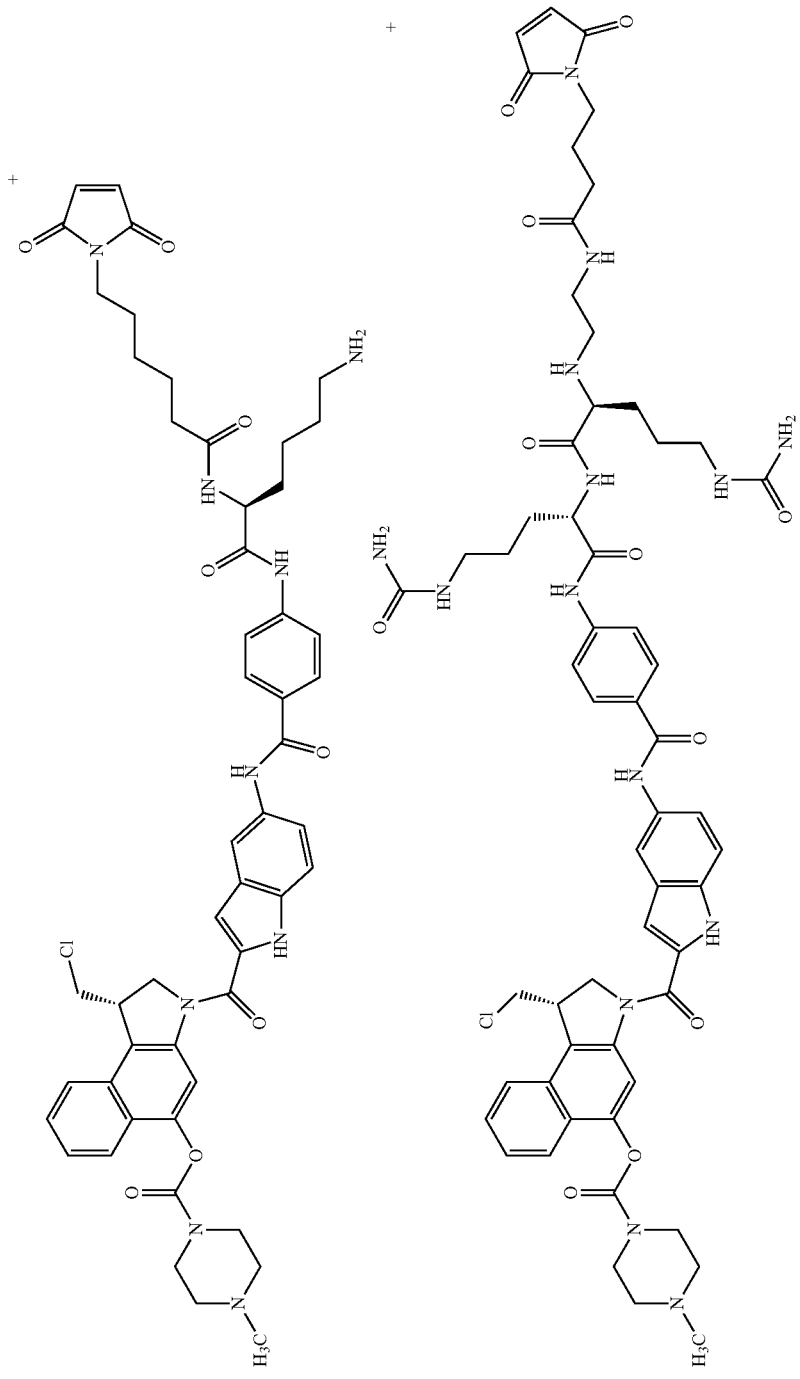

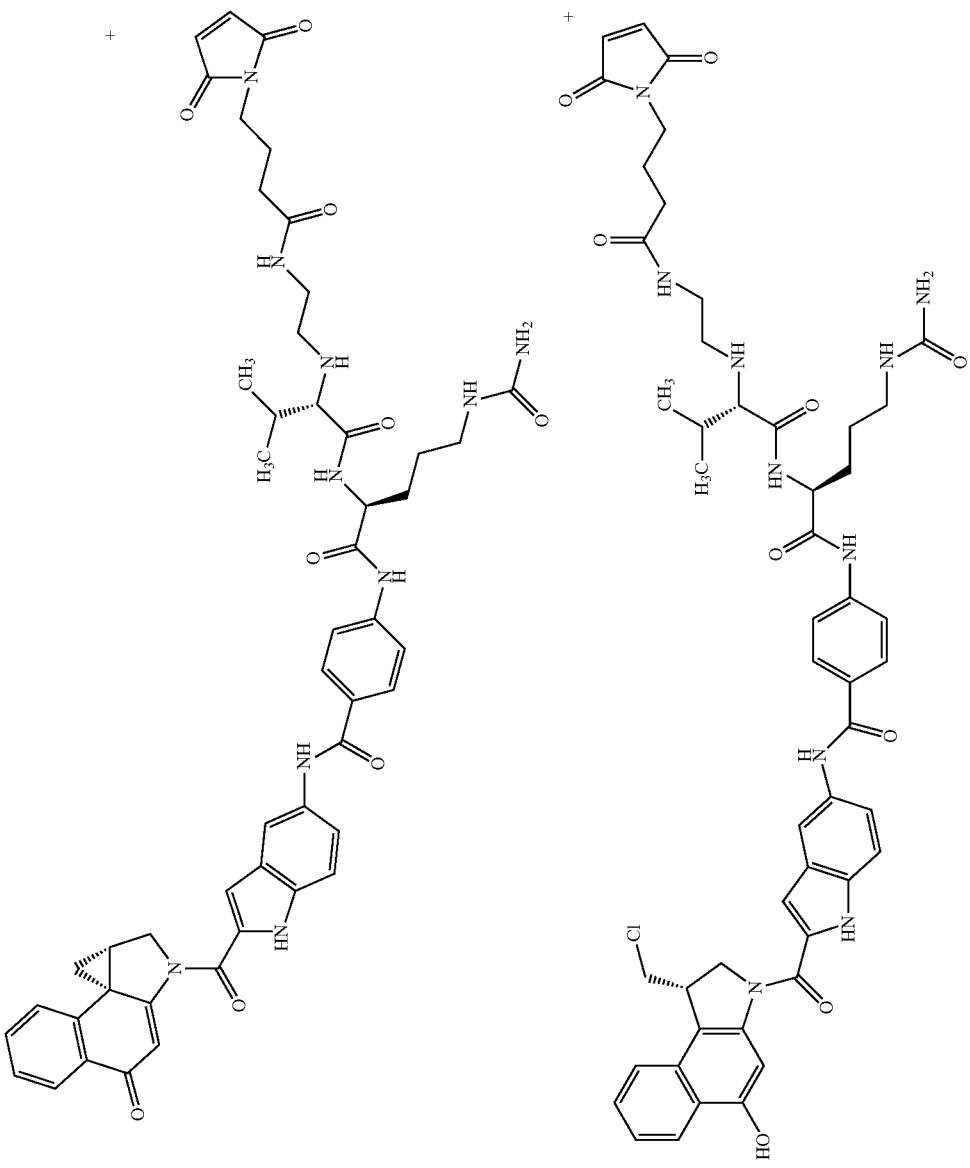

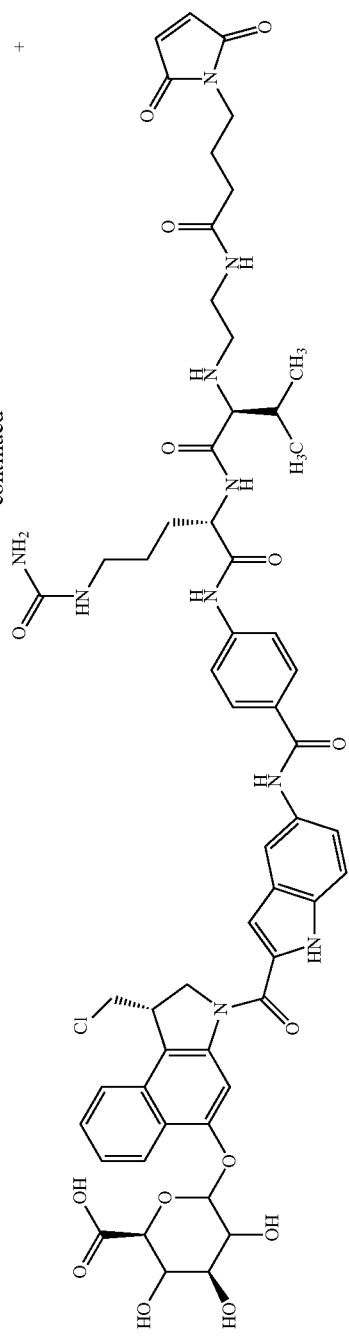

In the foregoing compounds, where the subscript r is present in a formula, it is an integer in the range of 0 to 24. R, wherever it occurs, is

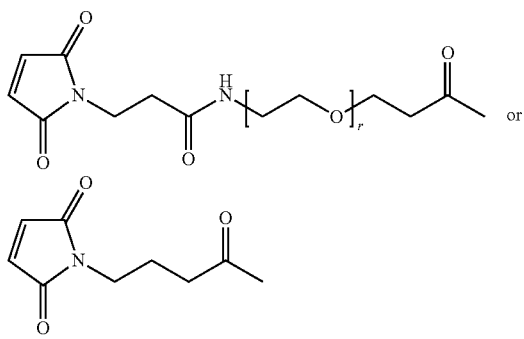

Each of the foregoing compounds has a maleimide group and is ready for conjugation to an antibody via a sulfhydryl group thereon.

Conjugation to the antibodies of this invention can also be effected by other types of chemical functionalities, as described hereinabove in the context of bispecific molecules.

Pharmaceutical Compositions

In another aspect, the present disclosure provides a pharmaceutical composition, comprising one or a combination of monoclonal antibodies, or antigen-binding portion(s) thereof, of the present disclosure, formulated together with a pharmaceutically acceptable carrier.

Pharmaceutical compositions of this disclosure also can be administered in combination therapy, i.e., combined with other agents. For example, the combination therapy can include an anti-mesothelin antibody of the present disclosure combined with at least one other anti-cancer agent. Examples of therapeutic agents that can be used in combination therapy are described in greater detail below.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate it.

The pharmaceutical compounds of this disclosure may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of this disclosure also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of this disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

The compositions may also contain adjuvants such as preservatives, wetting agents, emulsifying agents and dispersing agents. Prevention of the presence of microorganisms may be ensured both by sterilization procedures, supra, and by the inclusion of various antibacterial and antifungal agents, for example, paraben, chlorobutanol, phenol, sorbic acid, and the like. It may also be desirable to include isotonic agents, such as sugars, sodium chloride, and the like. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of this disclosure is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride.

Sterile injectable solutions can be prepared by microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) to yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of this disclosure are dictated by and directly dependent on (a) the unique characteristics of the active compound and the particular therapeutic effect to be achieved, and (b) the limitations inherent in the art of compounding such an active compound for the treatment of sensitivity in individuals.

For administration of an antibody of this invention, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/mL and in some methods about 25-300 μg/mL.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

For use in the prophylaxis and/or treatment of diseases related to abnormal cellular proliferation, a circulating concentration of administered compound of about 0.001 μM to 20 μM is preferred, with about 0.01 μM to 5 μM being preferred.

Patient doses for oral administration of the compounds described herein, typically range from about 1 mg/day to about 10,000 mg/day, more typically from about 10 mg/day to about 1,000 mg/day, and most typically from about 50 mg/day to about 500 mg/day. Stated in terms of patient body weight, typical dosages range from about 0.01 to about 150 mg/kg/day, more typically from about 0.1 to about 15 mg/kg/day, and most typically from about 1 to about 10 mg/kg/day, for example 5 mg/kg/day or 3 mg/kg/day.

In at least some embodiments, patient doses that retard or inhibit tumor growth can be 1 μmol/kg/day or less. For example, the patient doses can be 0.9, 0.6, 0.5, 0.45, 0.3, 0.2, 0.15, or 0.1 μmol/kg/day or less (referring to moles of the drug). Preferably, the antibody-drug conjugate retards growth of the tumor when administered in the daily dosage amount over a period of at least five days.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient, and like factors well known in the medical arts.

A "therapeutically effective dosage" of an anti-mesothelin antibody of this disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present disclosure can be administered via one or more routes of administration using one or more of a variety of methods known in the art. As will be appreciated by the skilled artisan, the route and/or mode of administration will vary depending upon the desired results. Preferred routes of administration for antibodies of this disclosure include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of this disclosure can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, a therapeutic composition of this disclosure can be administered with a needleless hypodermic injection device, such as those disclosed in U.S. Pat. Nos. 5,399,163; 5,383,851; 5,312,335; 5,064,413; 4,941,880; 4,790,824; or 4,596,556. Examples of implants and modules useful in the present disclosure include: U.S. Pat. No. 4,487,603 (implantable micro-infusion pump for dispensing medication at a controlled rate); U.S. Pat. No. 4,486,194 (therapeutic device for administering medicants through the skin); U.S. Pat. No. 4,447,233 (infusion pump for delivering medication at a precise infusion rate); U.S. Pat. No. 4,447,224 (variable flow implantable infusion apparatus for continuous drug delivery); U.S. Pat. No. 4,439,196 (osmotic drug delivery system having multi-chamber compartments); and U.S. Pat. No. 4,475,196 (osmotic drug delivery system). These patents are incorporated herein by reference. Many other implants, delivery systems, and modules are known to those skilled in the art.

The antibodies of this disclosure can be formulated to ensure proper distribution in vivo. For example, the blood-brain barrier (BBB) excludes many highly hydrophilic compounds. To ensure that the therapeutic compounds of this disclosure cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (Bloeman et al. (1995) *FEBS Lett.* 357:140; Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269: 9090); see also Keinanen and Laukkanen (1994) *FEBS Lett.* 346:123; Killion and Fidler (1994) *Immunomethods* 4:273.

Uses and Methods of the Invention

The antibodies, particularly the human antibodies, antibody compositions, antibody-partner molecule conjugate compositions and methods of the present invention have numerous in vitro and in vivo diagnostic and therapeutic utilities involving the diagnosis and treatment of mesothelin-mediated disorders. For example, these molecules can be administered to cells in culture, in vitro or ex vivo, or to human subjects, to treat, prevent and to diagnose a variety of disorders. As used herein, the term "subject" is intended to include human and non-human animals. Non-human animals include all vertebrates, e.g., mammals and non-mammals, such as non-human primates, sheep, dogs, cats, cows, horses, chickens, amphibians, and reptiles. Preferred subjects include human patients having disorders mediated by mesothelin activity, particularly human patients having a disorder associated with aberrant mesothelin expression. When antibody-partner molecule conjugates to mesothelin are administered together with another agent, the two can be administered in either order or simultaneously.

Given the specific binding of the antibodies of the invention for mesothelin, the antibodies of the invention can be used to specifically detect mesothelin expression and, moreover, can be used to purify mesothelin via immunoaffinity purification.

In one embodiment, the compositions of the invention can be used to detect levels of mesothelin, which levels can then be linked to certain disease symptoms. Alternatively, the compositions can be used to inhibit or block mesothelin function which, in turn, can be linked to the prevention or amelioration of certain disease symptoms, thereby implicating mesothelin as a mediator of the disease. This can be achieved by contacting a sample and a control sample with the anti-mesothelin antibody under conditions that allow for the formation of a complex between the antibody and mesothelin. Any complexes formed between the antibody and mesothelin are detected and compared in the sample and the control.

In another embodiment, the compositions of the invention can be initially tested for binding activity associated with therapeutic or diagnostic use in vitro. For example, compositions of the invention can be tested using flow cytometric assays known in the art.

The compositions of the invention have additional utility in therapy and diagnosis of mesothelin-related diseases. For example, the immunoconjugates can be used to elicit in vivo or in vitro one or more of the following biological activities: to inhibit the growth of and/or kill a cell expressing mesothelin; to mediate phagocytosis or ADCC of a cell expressing mesothelin in the presence of human effector cells, or to block mesothelin ligand binding to mesothelin.

In a particular embodiment, the compositions are used in vivo to treat, prevent or diagnose a variety of mesothelin-related diseases. Examples of mesothelin-related diseases include, among others, ovarian, pancreatic, stomach, lung, uterine, endometrial, bile duct, gastric/esophageal, colorectal, and breast cancers.

The compositions of the invention can comprise agents including, among others, anti-neoplastic agents such as doxorubicin (adriamycin), cisplatin, bleomycin sulfate, carmustine, chlorambucil, cyclophosphamide and hydroxyurea which, by themselves, are only effective at levels which are toxic or subtoxic to a patient. Cisplatin is intravenously administered as a 100 mg/kg dose once every four weeks and adriamycin is intravenously administered as a 60-75 mg/mL dose once every 21 days. Co-administration of the human anti-mesothelin antibodies, or antigen binding fragments thereof, of the present invention with chemotherapeutic agents provides two anti-cancer agents which operate via different mechanisms and yield a cytotoxic effect to human tumor cells. Such co-administration can solve problems due to development of resistance to drugs or a change in the antigenicity of the tumor cells, which would render them unreactive with the antibody.

Bispecific and multispecific molecules of the invention can also be used to modulate FcγR or FcγR levels on effector cells, such as by capping and elimination of receptors on the cell surface. Mixtures of anti-Fc receptors can also be used for this purpose.

The compositions of the invention which have complement binding sites, such as portions from IgG1, -2, or -3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions of the invention can also be administered together with complement. Thus, the instant disclosure provides compositions comprising human antibodies, multispecific or bispecific molecules and serum or complement. These compositions can be advantageous when the complement is located in close proximity to the human antibodies, multispecific or bispecific molecules. Alternatively, the human antibodies, multispecific or bispecific molecules of the invention and the complement or serum can be administered separately.

Also within the scope of the present invention are kits comprising the antibody compositions of the invention and instructions for use. The kit can further contain one or more additional reagents, such as an immunosuppressive reagent, a cytotoxic agent or a radiotoxic agent, or one or more additional human antibodies of the invention (e.g., a human antibody having a complementary activity which binds to an epitope in the mesothelin antigen distinct from the first human antibody).

Accordingly, patients treated with antibody compositions of the invention can be additionally administered (prior to, simultaneously with, or following administration of a composition of the invention) with another therapeutic agent, such as a cytotoxic or radiotoxic agent, which enhances or augments the therapeutic effect of the composition.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In a particular embodiment, the invention provides methods for detecting the presence of mesothelin antigen in a sample, or measuring the amount of mesothelin antigen, comprising contacting the sample, and a control sample, with a human monoclonal antibody, or an antigen binding portion thereof, which specifically binds to mesothelin, under conditions that allow for formation of a complex between the antibody or portion thereof and mesothelin. The formation of a complex is then detected, wherein a difference in complex formation between the sample compared to the control sample is indicative the presence of mesothelin antigen in the sample.

In other embodiments, the invention provides methods for treating a mesothelin-mediated disorder in a subject, e.g., ovarian, pancreatic, stomach, lung, uterine, endometrial, bile duct, gastric/esophageal, colorectal, and breast cancers.

In yet another embodiment, immunoconjugates of the invention can be used to partner molecules to cells that express mesothelin by linking such partner molecules to the antibody. For example, an anti-mesothelin antibody can be conjugated to any of the toxin compounds described in U.S. Pat. Nos. 6,281,354; 6,548,530; 2003/0050331; 2003/0064984; 2003/0073852; and 2004/0087497; or WO 03/022806. Thus, the invention also provides methods for localizing ex vivo or in vivo cells expressing mesothelin (e.g., with a detectable label, such as a radioisotope, a fluorescent compound, an enzyme, or an enzyme co-factor). Alternatively, the immunoconjugates can be used to kill cells that have mesothelin cell surface receptors by targeting cytotoxins or radiotoxins conjugated to mesothelin-binding antibodies In view of the association of mesothelin with certain tumors, the invention provides a method of inhibiting the growth of a mesothelin-expressing tumor cell, comprising contacting the tumor cell with an anti-mesothelin antibody of the disclosure such that growth of the tumor cells is inhibited. In a preferred embodiment, the antibody is conjugated to a therapeutic agent, such as a cytotoxin. In particularly preferred embodiments, the mesothelin-expressing tumor cell is a mesothelioma cell, or a tumor cell associated with ovarian, pancreatic, stomach, lung, uterine, endometrial, bile duct, gastric/esophageal, colorectal, and breast cancers. In other preferred embodiments, the mesothelin-expressing tumor cell is a mesothelioma cell, a pancreatic tumor cell, an ovarian tumor cell, a stomach tumor cell, a lung tumor cell or an endometrial tumor cell. In still other embodiments, the tumor cell is from a cancer selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

Furthermore, in another aspect, the anti-mesothelin antibodies and antibody drug conjugates thereof can be used in the treatment of cancer in a subject. Accordingly, the invention provides a method of treating cancer in a subject comprising administering to the subject an antibody of the disclosure such that the cancer is treated in the subject. For example, in a particularly preferred embodiment, the antibodies can be used in the treatment of mesotheliomas, ovarian cancers or pancreatic cancers. In other preferred embodiments, the antibodies are used in the treatment of mesotheliomas, pancreatic cancers, ovarian cancers, stomach cancers, lung cancers or endometrial cancers. In still other embodiments, the antibodies are used in the treatment of a cancer selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

The antibody can be used alone or in combination other cancer treatments, such as surgery and/or radiation, and/or with other anti-neoplastic agents, such as the anti-neoplastic agents discussed and set forth above, including chemotherapeutic drugs and other anti-tumor antigen antibodies, such as those that bind CD20, Her2, PSMA, Campath-1, EGFR and the like.

Optionally, antibodies to mesothelin can be combined with an immunogenic agent, such as a vaccine comprising cancerous cells, purified tumor antigens (including, recombinant proteins, peptides, and carbohydrate molecules), cells, and cells transfected with genes encoding immune stimulating cytokines (He et al (2004) *J. Immunol.* 173:4919-28). Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) *Proc. Natl. Acad. Sci. USA.* 90: 3539-43).

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in as a tumor vaccine is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) *Science* 269:1585-1588; Tamura, Y. et al. (1997) *Science* 278:117-120).

Dendritic cells (DC) are potent antigen presenting cells that can be used to prime antigen-specific responses. DC's can be produced ex vivo and loaded with various protein and peptide antigens as well as tumor cell extracts (Nestle, F. et al. (1998) *Nature Medicine* 4: 328-332). DCs may also be transduced by genetic means to express these tumor antigens as well. DCs have also been fused directly to tumor cells for the purposes of immunization (Kugler, A. et al. (2000) *Nature Medicine* 6:332-336). As a method of vaccination, DC immunization may be effectively combined with anti-mesothelin antibody treatment to activate anti-tumor responses.

The use of anti-mesothelin antibodies may also be combined with standard cancer treatments. Anti-mesothelin antibody treatment may be effectively combined with chemotherapeutic regimes. In these instances, it may be possible to reduce the dose of chemotherapeutic reagent administered (Mokyr, M. et al. (1998) *Cancer Research* 58: 5301-5304). Other combination therapies that may result in synergy with anti-mesothelin antibody treatment are radiation, surgery, and hormone deprivation. Angiogenesis inhibitors may also be combined with anti-mesothelin antibody treatment.

Anti-mesothelin antibody treatment can also be used in combination with bispecific antibodies that target Fc alpha or Fc gamma receptor-expressing effectors cells to tumor cells (see, e.g., U.S. Pat. Nos. 5,922,845 and 5,837,243). For example anti-Fc receptor/anti tumor antigen (e.g., Her-2/neu) bispecific antibodies have been used to target macrophages to sites of tumor. This targeting may more effectively activate tumor specific responses. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of immunosuppressive proteins expressed by the tumors. These include TGF-beta (Kehrl, J. et al. (1986) *J. Exp. Med.* 163: 1037-1050), IL-10 (Howard, M. & O'Garra, A. (1992) *Immunology Today* 13: 198-200), and Fas ligand (Hahne, M. et al. (1996) *Science* 274: 1363-1365). Antibodies to each of these entities may be used in combination with anti-mesothelin to counteract the effects of the immunosuppressive agent and favor tumor immune responses by the host.

Other antibodies which may be used to activate host immune responsiveness can be used in combination with anti-mesothelin. These include molecules on the surface of dendritic cells which activate DC function and antigen presentation. Anti-CD40 antibodies are able to substitute effectively for T cell helper activity (Ridge, J. et al. (1998) *Nature* 393: 474-478) and can be used in conjuction with anti-mesothelin antibodies (Ito, N. et al. (2000) *Immunobiology* 201 (5) 527-40). Antibodies to T cell costimulatory molecules such as CTLA-4 (e.g., U.S. Pat. Nos. 5,811,097, and 6,984,720), OX-40 (Weinberg, A. et al. (2000) *Immunol* 164: 2160-2169), 4-1BB (Melero, I. et al. (1997) *Nature Medicine* 3: 682-685 (1997), *ICOS* (Hutloff, A. et al. (1999) *Nature* 397: 262-266), PD-1 and/or PD-L1 may also provide for increased levels of T cell activation and thus, such T cell activating antibodies can be used in combination with the anti-mesothelin antibodies of the invention.

Bone marrow transplantation is currently being used to treat a variety of tumors of hematopoietic origin. While graft versus host disease is a consequence of this treatment, therapeutic benefit may be obtained from graft vs. tumor responses. Thus, anti-mesothelin antibody treatment can be used in combination with bone marrow transplantation as part of a tumor treatment regimen.

The present disclosure is further illustrated by the following examples, which should not be construed as further limiting. The contents of all figures and all references, Genbank sequences, patents and published patent applications cited throughout this application are expressly incorporated herein by reference in their entirety.

Example 1

Generation of Human Monoclonal Antibodies Against Mesothelin Protein

Anti-mesothelin human monoclonal antibodies were generated using transgenic mice that express human antibody genes, as follows.

Antigen

A mesothelin soluble fusion protein was used as the antigen for immunization. The soluble fusion protein was composed of the 40 kD portion of mesothelin (which is membrane-associated via a GPI-linkage in native mesothelin) linked to a His tag at its C-terminus. This fusion protein is referred to herein as "hu mesothelin-his fusion protein". The fusion protein was generated by standard recombinant DNA methods and expressed in transfected CHO cells, which secreted the soluble fusion protein into the culture supernatant. The CHO host cells used for transfection were obtained from Invitrogen (Cat #11619-012). The secreted soluble fusion protein was purified for use as immunogen. Furthermore, supernatant from the transfected CHO cells secreting hu mesothelin-his fusion protein was used in the ELISA assays for screening HuMAbs (described further below).

Transgenic Mice

Fully human monoclonal antibodies to human mesothelin were prepared using mice from the HCo7×hu Lamda strain of a transgenic mouse of the HuMab Mouse™ type ("Hco7×hu mouse"). In this strain, the endogenous mouse kappa light chain gene has been homozygously disrupted as described in Chen et al. (1993) *EMBO J.* 12:811-820 and the endogenous mouse heavy chain gene has been homozygously disrupted as described in Example 1 of WO 2001/09187. Furthermore, this mouse strain carries a human kappa light chain transgene, KCo5, as described in Fishwild et al. (1996) *Nature Biotechnology* 14:845-851, a yeast artificial chromosome (YAC) carrying most of the human lambda light chain locus, as described in WO 2000/026373, and a human heavy chain transgene, HCo7, as described in U.S. Pat. Nos. 5,545,806; 5,625,825; and 5,545,807.

Immunization of Mice

To generate fully human monoclonal antibodies to human mesothelin, HCo7×hu mice were immunized with purified hu mesothelin-his fusion protein. General immunization schemes are described in Lonberg, N. et al (1994) *Nature* 368(6474): 856-859; Fishwild, D. et al. (1996) *Nature Biotechnology* 14: 845-851 and WO 98/24884. The mice were 3-4 months of age upon the first infusion of antigen. A purified recombinant human mesothelin-his antigen preparation (10 µg purified from transfected mammalian cells expressing the fusion protein) was used to immunize the mice intraperitonealy and subcutaneously. The antigen was mixed 1:1 with RIBI adjuvant (Sigma Cat#M6536).

The mice were immunized 9 times at weekly intervals. The immune response was monitored by retro orbital bleeds. The plasma was screened by an indirect ELISA analysis (as described below), and mice with highest titers for anti-human mesothelin human IgG were used for fusions. Mice received a final boost by intravenous (IV) and intraperitoneal (IP) injection of soluble antigen 2 and 3 days before sacrifice and removal of the spleen.

Selection of Mice Producing Anti-Human Mesothelin Human Monoclonal Antibodies

To select the Hco7×hu mice producing high titers of anti-mesothelin antibodies, an indirect ELISA assay was used to monitor serum antibody titers, as follows. His-tag antibody coated microtiter plates (Novagen Cat. #71184) were hydrated and blocked with 300 µL/well of 1% BSA/DPBS for 10 to 15 minutes. After several washes, supernatant from CHO cells secreting hu mesothelin-his fusion protein, titered for maximum signal, was added (50 µl/well) and incubated for 1 hour. After washing plates with DPBS/Tween, dilutions of plasma from mesothelin immunized mice (starting at 1:50 dilution and serially diluted 1:2 11 times) were added to each well and incubated for 1 hour. The plates were washed with DPBS/Tween and incubated for 1 hour with goat-anti-human IgG polyclonal antibodies conjugated with horseradish peroxidase (Jackson ImmunoResearch Labs Cat. #115-036-098). ABTS (2,2'-azino-bis[3-ethylbenthiazolin 6-sulfonic acid]) substrate (Sigma Cat. #S9941) was then added and plates were analyzed spectrophotometrically at OD 415 nm.

Titer was defined as the dilution of serum that produced an OD two times the background OD. Titer was calculated using an Excel template. Mice that developed the highest titers of anti-human mesothelin antibodies were used for fusions. Fusions were performed as described below and hybridoma supernatants were tested for anti-human mesothelin activity using two different ELISA assay formats, also described below.

Generation of Hybridomas Producing Human Monoclonal Antibodies to Mesothelin Protein Mouse splenocytes isolated from high titer HCo7×hu mice and a mouse myeloma fusion partner were fused with an electric field based electrofusion using a Cyto Pulse large chamber cell fusion electroporator (Cyto Pulse Sciences, Inc., Glen Burnie, Md.). Single cell suspensions of splenic lymphocytes from immunized mice were fused to an equal number of P3X63 Ag8.6.53 (ATCC CRL 1580) nonsecreting mouse myeloma cells. Resulting cells were plated at $2.0 \times 10^4$ cells/well in flat bottom microtiter plates in selective DMEM medium containing high glucose (Cellgro #10-013-CM) and 10% fetal calf serum (Hyclone #SH30071.03), and supplemented with beta-mercaptoethanol (1000×, Gibco #21985-023), 7 mM HEPES (Cellgro 25-060-C1), additional 2 mM L-glutamine (Cellgro 25-005-Cl), HAT (50×, Sigma #H-0262), 5% Hybridoma Cloning Factor (BioVeris #210001), 10% P388DI (ATCC #CRL TIB-63) conditioned medium and Penicillin-Streptomycin (100×, Cellgro #30-002-CI). After about 7 days, some of the medium containing HAT was replaced with medium containing HT (Cellgro #25-047-CI).

After 10 to 12 days, individual wells were screened in a direct ELISA assay for wells containing human IgG/human kappa light chain or human IgG/human lambda light chain antibodies. In the direct ELISA format, microtiter plates were coated with goat anti-human IgG F(ab')$_2$ Fc fragment specific (Jackson ImmunoResearch Labs, Cat. #109-006-098), 2.5 µg/mL, 50 µl/wells, incubated for 1 hour and then blocked with 300 µL/well of 1% BSA/DPBS for 15 minutes. Blocking buffer was removed and supernatant from fusion plates was added (50 µL/well) and incubated for 1 hour. The plates were washed with DPBS/Tween and then incubated for 1 hour with goat-anti-human kappa light chain polyclonal antibodies conjugated with horseradish peroxidase (Bethyl Cat. #A80-115P) or goat-anti-human lambda light chain polyclonal antibodies conjugated with horseradish peroxidase (Biosource Cat. #10904). After washing, the plates were developed with ABTS substrate and analyzed spectrophotometrically at OD 415 nm. Wells with an elevated OD>0.75, were selected for further analysis.

Hybridoma cells from wells positive for human IgG/human kappa light chain or human IgG/human lambda light chain antibodies were transferred to 24-well cultures. A few days later, cell supernatant from individual wells was rescreened for specificity using an indirect ELISA to identify human IgG antibody producing hybridomas specific to human mesothelin. The protocol for the indirect ELISA used for the secondary screen of the hybridomas was the same protocol as described above for testing serum antibody titers in the Hco7×hu mice, except that the sample supernatant was from hu IgG/hu kappa or hu IgG/hu lambda positive cultures.

The hybridomas were cloned by serial dilution and screened two times. Multiple characterization assays (described in the following examples) were performed using supernatants from overgrown 24-well cultures prior to cloning. Ten anbitodies were selected and their characteristics were confirmed using clonal in vitro produced and purified antibody. Three antibodies, 3C10 (original clone name:

1382.210.3C10.1.6), 6A4 (original clone name: 1382.210.6A4.1.6) and 7B1 (original clone name: 1382.210.7B1.2.18), were selected for sequencing and further analysis.

Example 2

Structural Characterization of Antibodies 3C10, 6A4 and 7B1

The cDNA sequences encoding the heavy and light chain variable regions of the mAbs expressed by the 3C10, 6A4 and 7B1 clones, as described in Example 1, were sequenced using standard DNA sequencing techniques and the expressed proteins were characterized by standard protein chemistry analysis. All three clones were found to express an antibody comprising an IgG1 heavy chain and a kappa light chain.

The nucleotide and amino acid sequences of the $V_H$ of 3C10 are shown in FIG. 1A and in SEQ ID NO: 25 and 19, respectively. The nucleotide and amino acid sequences of the kappa $V_L$ of 3C10 are shown in FIG. 1B and in SEQ ID NO: 28 and 22, respectively.

Comparison of the 3C10 heavy chain immunoglobulin sequence to the known human germline immunoglobulin heavy chain sequences demonstrated that the 3C10 heavy chain utilizes a $V_H$ segment from human germline $V_H$ 3-33, a D segment from human germline D3-10 and a JH segment from human germline JH 4B. Further analysis of the 3C10 $V_H$ sequence using the Kabat system of CDR region determination led to the delineation of the heavy chain CDR1, CDR2 and CD3 regions as shown in FIG. 1A and in SEQ ID NOs: 1, 4 and 7, respectively.

Comparison of the 3C10 light chain immunoglobulin sequence to the known human germline immunoglobulin light chain sequences demonstrated that the 3C10 kappa light chain utilizes a $V_K$ segment from human germline $V_K$ L6 and a $J_K$ segment from human germline JK 4. Further analysis of the 3C10 $V_K$ sequence using the Kabat system of CDR region determination led to the delineation of the light chain CDR1, CDR2 and CD3 regions as shown in FIG. 1B and in SEQ ID NOs: 10, 13 and 16, respectively.

The nucleotide and amino acid sequences of the $V_H$ of 6A4 are shown in FIG. 2A and in SEQ ID NO: 26 and 20, respectively. The nucleotide and amino acid sequences of the $V_L$ of 6A4 are shown in FIG. 2B and in SEQ ID NO: 29 and 23, respectively.

Comparison of the 6A4 heavy chain immunoglobulin sequence to the known human germline immunoglobulin heavy chain sequences demonstrated that the 6A4 heavy chain utilizes a $V_H$ segment from human germline $V_H$ 3-33, a D segment from the human germline D3-10, and a JH segment from human germline JH 4B. Further analysis of the 6A4 $V_H$ sequence using the Kabat system of CDR region determination led to the delineation of the heavy chain CDR1, CDR2 and CD3 regions as shown in FIG. 2A and in SEQ ID NOs: 2, 5 and 8, respectively.

Comparison of the 6A4 light chain immunoglobulin sequence to the known human germline immunoglobulin light chain sequences demonstrated that the 6A4 kappa light chain utilizes a $V_k$ segment from human germline $V_K$ L6 and a $J_K$ segment from human germline JK 4. Further analysis of the 6A4 $V_k$ sequence using the Kabat system of CDR region determination led to the delineation of the light chain CDR1, CDR2 and CD3 regions as shown in FIG. 2B and in SEQ ID NOs: 11, 14 and 17, respectively.

The nucleotide and amino acid sequences of the $W_I$ of 7B1 are shown in FIG. 3A and in SEQ ID NO: 27 and 21, respectively. The nucleotide and amino acid sequences of the $V_L$ of 7B1 are shown in FIG. 3B and in SEQ ID NO: 30 and 24, respectively.

Comparison of the 7B1 heavy chain immunoglobulin sequence to the known human germline immunoglobulin heavy chain sequences demonstrated that the 7B1 heavy chain utilizes a $V_H$ segment from human germline $V_H$ 3-7, a D segment from the human germline D3-10, and a JH segment from human germline JH 6B. Further analysis of the 7B1 $V_H$ sequence using the Kabat system of CDR region determination led to the delineation of the heavy chain CDR1, CDR2 and CD3 regions as shown in FIG. 3A and in SEQ ID NOs: 3, 6 and 9, respectively.

Comparison of the 7B1 light chain immunoglobulin sequence to the known human germline immunoglobulin light chain sequences demonstrated that the 7B1 kappa light chain utilizes a $V_k$ segment from human germline $V_K$ A27 and a $J_K$ segment from human germline JK 2. Further analysis of the 7B1 $V_k$ sequence using the Kabat system of CDR region determination led to the delineation of the light chain CDR1, CDR2 and CD3 regions as shown in FIG. 3B and in SEQ ID NOs: 12, 15 and 18, respectively.

FIG. 4 shows the alignment of the 3C10 and 6A4 heavy chain variable amino acid sequences (SEQ ID NOs: 19 and 20, respectively) with the germline $V_H$ 3-33 encoded amino acid sequence (SEQ ID NO: 31). The CDR1, CDR2 and CDR3 regions are delineated.

FIG. 5 shows the alignment of the 3C10 and 6A4 kappa light chain variable amino acid sequences (SEQ ID NOs: 22 and 23, respectively) with the germline $V_K$ L6 encoded amino acid sequence (SEQ ID NO: 33). The CDR1, CDR2 and CDR3 regions are delineated.

FIG. 6 shows the alignment of the 7B1 heavy chain variable amino acid sequence (SEQ ID NO: 21) with the germline $V_H$ 3-7 encoded amino acid sequence (SEQ ID NO: 32). The CDR1, CDR2 and CDR3 regions are delineated.

FIG. 7 shows the alignment of the 7B1 kappa light chain variable amino acid sequence (SEQ ID NO: 24) with the germline $V_K$ A27 encoded amino acid sequence (SEQ ID NO: 34). The CDR1, CDR2 and CDR3 regions are delineated.

The 3C10, 6A4 and 7B1 variable regions can be converted to full-length antibodies of any desired isotype using standard recombinant DNA techniques. For example, DNA encoding the $V_H$ and $V_L$ regions can be cloned into an expression vector that carries the heavy and light chain constant regions such that the variable regions are operatively linked to the constant regions. Alternatively, separate vectors can be used for expression of the full-length heavy chain and the full-length light chain. Non-limiting examples of expression vectors suitable for use in creating full-length antibodies include the pIE vectors described in US 2005/0153394 by Black.

Example 3

Characterization of Binding Properties of Mesothelin Monoclonal Antibodies

In this example, the binding of mAbs 3C10, 6A4 and 7B1 to cell surface mesothelin was examined by flow cytometry. Furthermore, binding kinetics to mesothelin were analyzed by BIACORE analysis.

A. Flow Cytometry Studies

To test the ability of the antibodies to bind to cell surface mesothelin protein, the antibodies were incubated with four different mesothelin-expressing cells: OVCAR3 (ATCC Designation HTB-161, a human ovarian cancer cell line), NCI-H226 (ATCC Designation CRL-5826, a human lung-derived mesothelioma), CFPAC-1 (ATCC Designation CRL-1918, a human pancreatic cancer cell line), and KB (ATCC Designation CCL-17, a human oral carcinoma cell line). For the flow cytometry studies, the 3C10, 6A4 and 7B1 monoclonal antibodies were diluted with cold 1×PBS+0.1% BSA to 40 μg/mL. For the binding reaction, 50 μl of diluted antibody solution was added to a 50 μl cell suspension containing $4 \times 10^5$ cells and the mixture was incubated on ice for 30-60 minutes. The cells were then washed three times with 1×PBS+0.1% BSA. A 1:50 dilution of R-phycoerythrin-labeled goat anti-human IgG FγF(ab)$_2$ fragment (Jackson ImmunoResearch Labs, Cat. #109-116-098) was added and the mixture was incubated on ice for 1 hour, followed by washing twice with cold 1×PBS+0.1% BSA. After the final wash, 200 μl of cold 1×PBS+0.1% BSA was added to each solution and analysis of antibody binding was carried out by FACS.

The results of the flow cytometry analysis are summarized below in Table 1, which shows $EC_{50}$ for binding to the four different cell lines. The results demonstrate that all three monoclonal antibodies bind effectively to cell-surface human mesothelin.

TABLE 1

Binding of Anti-Mesothelin Antibodies to Cells Expressing Human Mesothelin

| Antibody | OVCAR3 Cells $EC_{50}$ (nM) | NCI-H226 Cells $EC_{50}$ (nM) | CFPAC-1 Cells $EC_{50}$ (nM) | KB Cells $EC_{50}$ (nM) |
|---|---|---|---|---|
| 3C10 | 0.2126 | 0.1968 | 0.1933 | 0.1441 |
| 6A4 | 0.1697 | 0.1556 | 0.1932 | 0.1815 |
| 7B1 | 0.1103 | 0.6642 | 0.0643 | 0.06793 |

B. BIACORE Analysis

The binding of the 3C10, 6A4 and 7B1 antibodies to recombinant soluble mesothelin his-fusion protein was examined by BIAcore™ using a capture method. The 3C10, 6A4 and 7B1 antibodies each were separately captured on a protein G (Pierce, Rockford, Ill.) coated CM5 chip at high density (4000RUs). The coating was performed based on the standard immobilization procedure recommended by the manufacturer. After the 3C10, 6A4 or 7B1 purified antibody was captured on protein G, a concentration series of recombinant human mesothelin His-fusion protein (450, 225, 112.5, 56, and 28 nM) was injected over the captured antibody for 2 minutes at a flow rate of 25 μL/mL. The antigen was allowed to dissociate for 8 minutes. Isotype controls were run on the chip, and the data used to subtract non-specific binding. All the analyses were carried out on a Biacore 2000 or 3000 surface plasmon resonance instrument, using BIAcore Control software v 4.01. Data was analyzed using BiaEvaluation v4.01 software.

The results are shown in Table 2 below. The BIAcore results for 3C10, 6A4 and 7B1 confirm the flow cytometry results that all three antibodies are capable of binding with high affinity to human mesothelin.

TABLE 2

Binding Affinity and Kinetics of Anti-Mesothelin Antibodies to Recombinant Human Mesothelin

| Antibody | $K_D \times 10^{-9}$ (M) | $k_{on}$ (1/Ms) $\times 10^4$ | $k_{off}$ (1/s) $\times 10^{-4}$ |
|---|---|---|---|
| 3C10 | 5.8 | 6.30 | 3.62 |
| 6A4 | 5.9 | 6.39 | 3.77 |
| 7B1 | 2.4 | 7.15 | 1.71 |

To investigate the epitopes bound by the 3C10, 6A4 and 7B1 mAbs, epitope binning analyses were performed with BIAcore. 3C10 and 7B1 mAbs were covalently linked to a CM5 chip (carboxy methyl dextran coated chip) via primary amines, using the standard amine coupling chemistry and kit provided by Biacore. Mixtures of antibody-antigen complex were flowed across the immobilized antibodies. The antibody concentrations were a two-fold dilution series starting at between 50 and 500 nM. The mesothelin concentration was between 22 and 44 nM. Antibodies and mesothelin were pre-incubated for at least 1 hour prior to injection. Antibody-antigen mixtures (15 uL) were injected at a flow rate of 6 μl/min Antibodies that have overlapping epitopes will compete out (decreasing response with increasing antibody concentration) whereas those with distinct epitopes will simultaneously bind to the antigen (increasing response with increasing antibody concentration). The results were that 3C10 mAb bound to the same (or very similar epitope) as the previously described mouse anti-mesothelin mAb K1. The 7B1 mAb bound to a distinct epitope from 3C10 and K1. The 6A4 mAb was able to block both 3C10 and 6A4 binding to recombinant mesothelin.

Example 4

Characterization of Stability of Mesothelin Monoclonal Antibodies

In this example, the stability of mAbs 3C10, 6A4 and 7B1 was examined in chemical unfolding and thermal stability analyses, as follows.

The stability of the anti-mesothelin monoclonal antibodies were compared by measuring the midpoint of chemical denaturation by fluorescence spectroscopy. Fluorescence measurements of chemical denaturation were performed on a SPEX Fluorolog 3.22 equipped with a Micromax plate reader (SPEX, Edison, N.J.). The measurements were performed on antibody samples that had been left to equilibrate for 20 hours in 16 different concentrations of guanidinium hydrochloride (GdHCL) in PBS buffer ranging from 0 to 6 Molar. The measurements were made in black, low volume, non-binding surface 384-well plates (Corning, Acton, Mass.) and required 1 μM of antibody in a well volume of 12 μL. Fluorescence was excited at 280 nm and the emission spectra were measured between 320 and 400 nm. The scan speed was 1 second per nm and slits were set to 5 nm bandpass. A buffer blank was performed using PBS and automatically subtracted from the data. Data was fitted to a two-state denaturation model using the GraphPad Prism software. The results, expressed as the molar concentration of GdHCl that was the unfolding midpoint, are shown below in Table 3.

TABLE 3

Chemical Stability of anti-Mesothelin Antibodies

| Antibody | Unfolding Midpoint (GdHCl, M) |
|---|---|
| 3C10 | 2.50 |
| 6A4 | 2.67 |
| 7B1 | 2.21 |

The thermal stability of the anti-mesothelin monoclonal antibodies was determined by calorimetric analysis of the melting temperature of the antibodies.

Calorimetric measurements of melting temperatures ($T_m$) were performed on a VP-Capillary DSC differential scanning microcalorimeter platform that is combined with an autosampler (MicroCal LLC, Northampton, Mass., USA). Denaturation data on the antibodies was obtained by heating the samples, at a concentration of 0.25 mg/mL, from 30 to 95° C. at a rate of 1° C./min. The antibody samples were present in phosphate-buffered saline (PBS) at pH 7.4. The same buffer was used in the reference cell to obtain the molar heat capacity by comparison. The observed thermograms were baseline corrected and normalized data analyzed based on a non-2-state model, using the software Origin v7.0. The results, expressed as temperature (in ° C.) at which peaks indicative of antibody melting were observed, are shown in Table 4 below.

TABLE 4

Thermal Stability of Mesothelin Antibodies

| Antibody | Peak 1 (° C.) | Peak 2 (° C.) | Peak 3 (° C.) |
| --- | --- | --- | --- |
| 3C10 | 67 | | 81 |
| 6A4 | 69 | | 81 |
| 7B1 | 69.8 | 72.7 | 82 |

The results above indicate that the 3C10, 6A4 and 7B1 antibodies have desirable chemical and thermal stability properties.

Example 5

Internalization of Mesothelin Antibodies

In this example, the ability of the 3C10, 6A4 and 7B1 antibodies to be internalized by mesothelin-expressing cells was examined, as follows.

In the first series of analyses, a Hum-ZAP assay was used to examine antibody internalization. In the Hum-ZAP assay (kits for which are commercially available from Advanced Targeting Systems, San Diego, Calif.), the anti-mesothelin antibodies were reacted with mesothelin-expressing cells and with a goat anti-human IgG antibody conjugated to the toxin saporin (a ribosome inactivating protein). Upon internalization of the primary anti-mesothelin antibody, the secondary saporin-conjugated antibody is also taken inside the cell, resulting in protein synthesis inhibition and eventual cell death after 2-4 days.

More specifically, cells were diluted to $5 \times 10^4$ cells/mL in cell culture medium. 50 µl of diluted cells were added to each well of a flat-bottomed 96 well tissue culture plate and incubated overnight in a 37° C., 5% $CO_2$ incubator. Antibodies were diluted with culture medium to a concentration of 4 µg/mL and 0.4 µg/mL. 25 µl of diluted antibody was added to the cultured cells so the final antibody concentrations were 1 µg/mL and 0.1 µg/mL. Cell and antibody were incubated for 10 minutes before addition of 25 µl of 8 µg/mL Hum-zap reagent. The mixture was incubated at 37° C., 5% $CO_2$ for 72 hours. 100 µl of Celltiter-Glo (a viability dye) was added to each well and gently swirled for 2 minutes. After 10 minutes at room temperature, plates were read on a Promega Veritas Microplate Luminator.

The Hum-ZAP assay was conducted using the mesothelin-expressing cell lines NCI-H226, CFPAC-1 and KB (described in Example 3) as target cells, as well as CHO cells transfected to express mesothelin on the cell surface via a GPI-linkage (CHO-mesothelin). The results are expressed qualitatively below in Table 5:

TABLE 5

Internalization of Mesothelin Antibodies Using Hum-ZAP Assay

| Antibody | CHO—Mesothelin | NCI-H226 | CFPAC-1 | KB |
| --- | --- | --- | --- | --- |
| 3C10 | + | N.D | N.D | + |
| 6A4 | + | + | + | + |
| 7B1 | + | N.D | N.D | +/− |

N.D. = Not determined

The Hum-ZAP assay results demonstrate that the 6A4 antibody was internalized by all four cell lines. The 3C10 and 7B1 antibodies also were internalized by the CHO-mesothelin cells. Still further, the 3C10 antibody was internalized by the KB cells, whereas the 7B1 antibody was internalized less well by the KB cells than the other two antibodies.

In the second series of analyses, the internalization of the 6A4 antibody by the NCI-H226 cell line was further examined using an immunofluoresence assay. In this assay, NCI-H226 were grown to 80% confluency. The adherent cells were lifted with a cell dissociation buffer (Cell Stripper) and $1.35 \times 10^6$ cells were transferred to a 15 ml conical tube and washed once with FACS buffer (PBS+2% fetal bovine serum). The cells were incubated with 6A4 antibody at 20 µg/mL in a volume of 450 µL FACS buffer (PBS+2% fetal bovine serum) at 4° C. for 30 min followed by washing with cold FACS buffer. Cells were then stained with a detection antibody, a goat anti-human IgG antibody conjugated to Rhodamine at 20 µg/mL in FACS Buffer at 4° C. for 30 minutes, followed by washing with cold FACS buffer. This receptor/antibody complex was further resuspended in 450 µL FACS buffer and incubated with the cells at 37° C./5% $CO_2$ for specified times (zero, 5, 10, 15, 30, 60, 120 minutes, and overnight) to allow for internalization. At specified time points, 50 µL aliquots, corresponding to 150,000 cells, were transferred into 96-well plates and stained with a wheat germ agglutinin-Alexa Fluor 488 conjugate (Invitrogen, Cat. #W11261), which stains the cell surface. The cell aliquots were incubated on ice for 30 minutes with 10 µg/mL WGA in FACS Buffer, followed by washing with FACS Buffer. Finally, the cells were washed with FACS buffer and fixed by addition of 2% paraformaldehyde and analyzed by fluorescence microscopy for associated immunofluorescence using excitation/emission wavelengths 495/519 and 554/570 for Alexa488 and Rhodamine respectively. The results confirmed that the 6A4 mAb is effectively internalized by the NCI-H226 cells.

Example 6

Inhibition of Binding of Mesothelin to CA125 by Anti-Mesothelin mAbs

To test the ability of the anti-mesothelin antibodies to inhibit binding of mesothelin to CA125, an in vitro heterotypic cell adhesion assay was performed. In this assay, the ability of the antibodies to inhibit adhesion of OVCAR3 cells (an ovarian cancer cell line that expresses CA125) to CHO cells transfected to express mesothelin on their cell surface (CHO-mesothelin) was examined. Adhesion of OVCAR3 cells (described further in Example 3) to CHO-mesothelin cells is mediated by the interaction of mesothelin with CA125.

To test antibody inhibition of the mesothelin/CA125 interaction, OVCAR cells were plated at a density of $4 \times 10^4$ cells/200 µl per well in a 96-well plate 24 hours prior to the assay to obtain a subconfluent culture of cells. After 24 hours, medium was removed and fresh medium containing 1% bovine serum albumin (BSA) plus 10 µg/mL of antibody (3C10, 7B1, 6A4, isotype control or no antibody) was added to the wells. Cells were incubated at 37° C. with 5% $CO_2$ for 30 minutes. CHO-S (parental cells) and CHO-Mesothelin cells were incubated 30 minutes with Calcein AM (5 µM for $6 \times 10^6$ cells/mL), washed with medium and added to the OVCAR cultures and incubated for 60 minutes at 37° C.

Following the incubation, samples were washed 4 times with PBS to remove unattached cells. Attached cells were measured by adding 100 µl/well PBS and reading plates with the Synergy-HT Fluorescence reader at 494 nm/517 nm.

The results are illustrated in FIG. 8. The results show that OVCAR3 cells adhered to CHO-mesothelin cells in the absence of antibodies, but did not adhere to control CHO-S cells that did not express mesothelin on their cell surface. Furthermore, the presence of the 3C10 mAb or the 6A4 mAb resulted in approximately 68.7% inhibition or 84.8% inhibition, respectively, in cell adhesion, as compared to a control antibody (DT). In contrast, the 7B1 mAb did not exhibit the ability to inhibit the interaction of mesothelin with CA125, indicating that the epitope to which 7B1 binds on mesothelin (which differs from the 3C10 and 6A4 epitopes) does not block the mesothelin-CA125 interaction region.

Example 7

Antibody-Dependent Cellular Cytotoxicity

To determine the ability of antibody 6A4 to kill mesothelin-expressing cells in the presence of effector cells via antibody dependent cellular cytotoxicity (ADCC), a fluorescence cytotoxicity assay was used. CHO cells transfected to express the 40 kD membrane-associated portion of mesothelin on their cell surface (CHO-mesothelin cells) were used as the target cells.

Human effector cells were prepared from whole blood as follows. Human peripheral blood mononuclear cells were purified from heparinized whole blood by standard Ficoll-paque separation. The cells were resuspended in RPMI1640 media containing 10% FBS (heat-inactivated) and 200 U/mL of human IL-2 and incubated overnight at 37° C. The following day, the cells were collected and washed four times in culture media and resuspended at $2 \times 10^7$ cells/mL. Target CHO-mesothelin cells were prepared by incubating with BATDA reagent (Perkin Elmer, Wellesley, Mass.) at 2.5 µl BATDA per $1 \times 10^6$ target cells/mL for 20 minutes at 37° C. The target cells were washed four times, spun down and brought to a final volume of $1 \times 10^5$ cells/mL.

The CHO-mesothelin cells were tested for antibody specific ADCC to the human anti-mesothelin 6A4 monoclonal antibody using the Delfia fluorescence emission analysis as follows. CHO-mesothelin cells (100 µl of labeled target cells, $10^4$ cells/well) were incubated with 50 µl of effector cells ($10^6$ cells/well) and 50 µl of antibody (10 ug/mL final concentration). A target to effector ratio of 1:100 was used throughout the analyses. In all studies, a human IgG1 isotype control was used as a negative control. Cells were spun down at 2000 rpm and incubated for one hour incubation at 37° C. The supernatants were then collected, submitted to centrifugation and 20 µl of supernatant was transferred to a flat bottom plate, to which 180 µl of Eu solution (Perkin Elmer, Wellesley, Mass.) was added and read in a RubyStar reader (BMG Labtech). The % lysis was calculated as follows: (sample release−spontaneous release*100)/(maximum release−spontaneous release), where the spontaneous release is the fluorescence from wells which contain target cells plus effector cells and maximum release is the fluorescence from wells containing target cells and have been treated with 2% Triton-X.

The results are summarized below in Table 6, which shows the $EC_{50}$ in nM.

TABLE 6

| Antibody Dependent Cellular Cytotoxicity Mediated by 6A4 Antibody | |
| --- | --- |
| Antibody | $EC_{50}$ (nM) |
| 6A4 | 63.10 |
| Isotype Control | 682.7 |

The results demonstrate that the 6A4 monoclonal antibody exhibits ADCC activity against a cell line expressing mesothelin on its cell surface.

Example 8

Tumor Growth Inhibition In Vivo by Anti-Mesothelin mAb 6A4

In this example, the ability of the 6A4 mAb, either as a naked antibody or as a cytotoxin conjugate, to inhibit tumor growth in mouse models in vivo, was examined. The cytotoxin conjugate of 6A4 is referred to herein as 6A4-Cytotoxin A, which is composed of the 6A4 antibody linked to Cytotoxin A. The Cytotoxin A cytotoxin, and preparation thereof, is described further in WO 2008/083312, the entire content of which is specifically incorporated herein by reference. The 6A4-Cytotoxin A conjugate was prepared as follows:

Antibody 6A4 was concentrated to approximately 5 mg/mL, buffer exchanged into 100 mM phosphate buffer, 50 mM NaCl, 2 mM DTPA pH 8.0 and thiolated by addition of an 8 to 10-fold molar excess of 2-Imminothiolane for 60 minutes at room temperature. Following thiolation, the antibody was buffer exchanged into 50 mM HEPES buffer, containing 5 mM glycine, 2 mM DTPA, and 0.5% Povidone (10 K) pH 5.5. Thiolation was quantified with 4,4"-dithiodipyridine by measuring thiopyridine release at 324 nM. Conjugation was achieved by addition of maleimide containing drug Cytotoxin A at a 3:1 molar ratio of drug to thiols. Incubation was at room temperature for 60 minutes followed by the addition of 10:1 molar ratio of N-ethylmaleimide (NEM) to thiols to the reaction mix. After incubation in the presence of NEM, the resulting conjugates were purified by size-exclusion chromatography on a Sephacryl-200 column run in 50 mM HEPES, 5 mM glycine, 100 mM NaCl, pH 6.0. Fractions containing monomeric antibody conjugate were pooled and concentrated by ultrafiltration. Antibody conjugate concentration and substitution ratios were determined by measuring absorbance at 280 and 340 nm.

Cytotoxin A has the structure shown below:

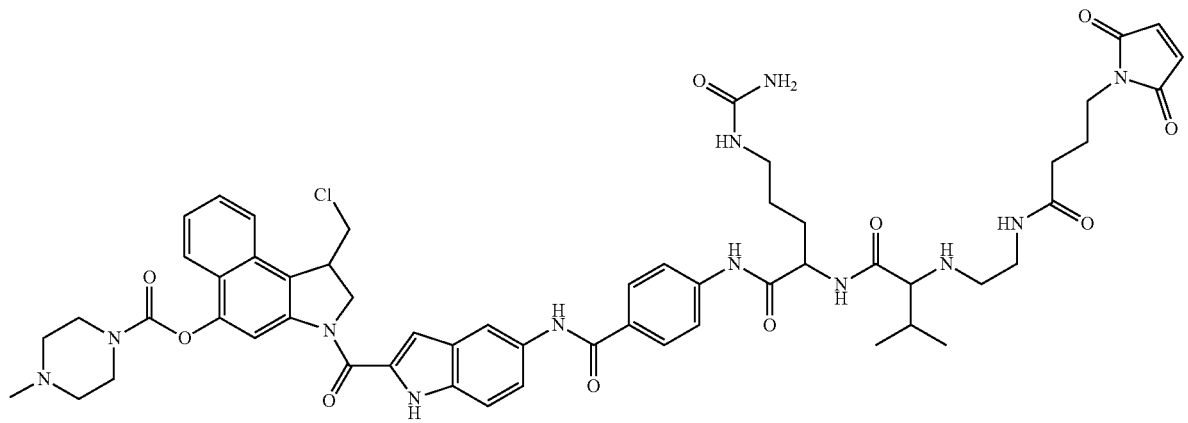

Cytotoxin A

Those skilled in the art will appreciate that although the term "cytotoxin" is employed, the structure shown actually encompasses both the cytotoxin proper (partner molecule) and a linker moiety for joining the cytotoxin to the antibody and that, after cleavage of the conjugate, the toxin is released in a prodrug form that is then hydrolyzed to the toxin proper. Thus, strictly speaking, the partner molecule in a conjugate of this invention can be viewed either as the prodrug form or the cytotoxin proper.

(10 mg/kg or 30 mg/kg) or with 6A4-Cytotoxin A conjugate (0.1 µmole/kg), along with controls: vehicle alone (PBS, Q3D×4), an isotype-matched human IgG1 antibody (4A3) or an isotype-matched human IgG1 antibody linked to the Cytotoxin A cytotoxin (iso-Cytotoxin A).

The 6A4 antibody, and its controls, were administered on days 40, 43, 47 and 51. The 6A4-Cytotoxin A conjugate, and its controls, were administered on days 40 and 64. Tumor volume was measured at regular intervals until day 105.

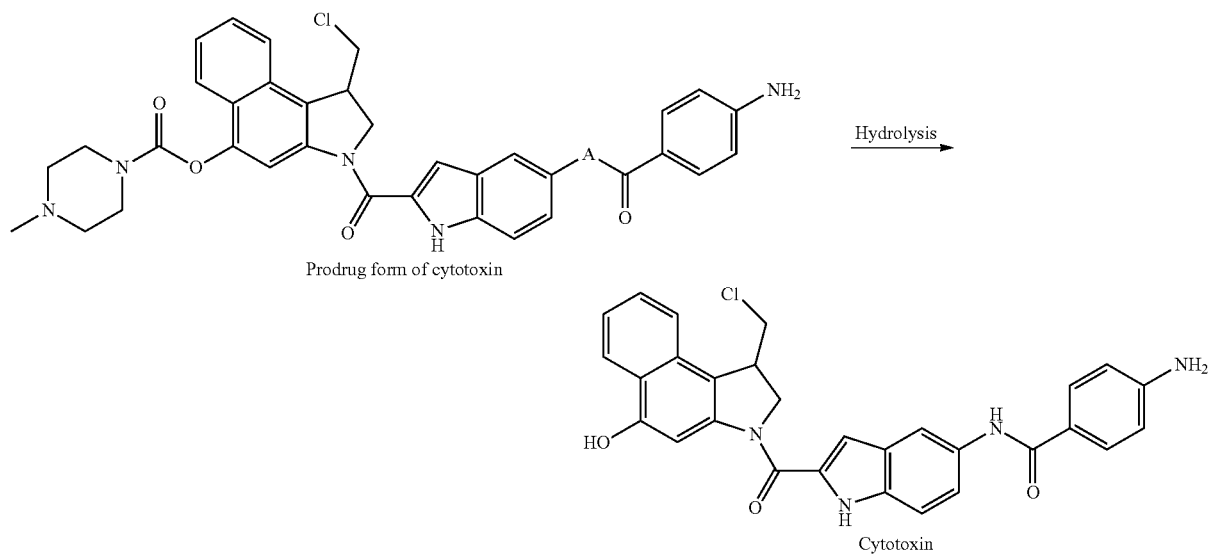

Prodrug form of cytotoxin

Cytotoxin

In a first series of analyses, the effect of 6A4 and 6A4-Cytotoxin A on the growth of NCI-H226 cells (a lung-derived mesothelioma; ATCC Designation CRL-5826) in a mouse xenograft model was examined. In this xenograft model, SCID mice (CB17, from Taconic, Germantown, N.Y.) were implanted with $9 \times 10^6$ NCI-H226 cells/mouse and the NCI-H226 cells were allowed to grow for 36 days. On day 40, at which time the mean tumor volume was 87 mm³, the mice were randomized and treated intraperitoneally (i.p.) with 6A4

Figure 9A:
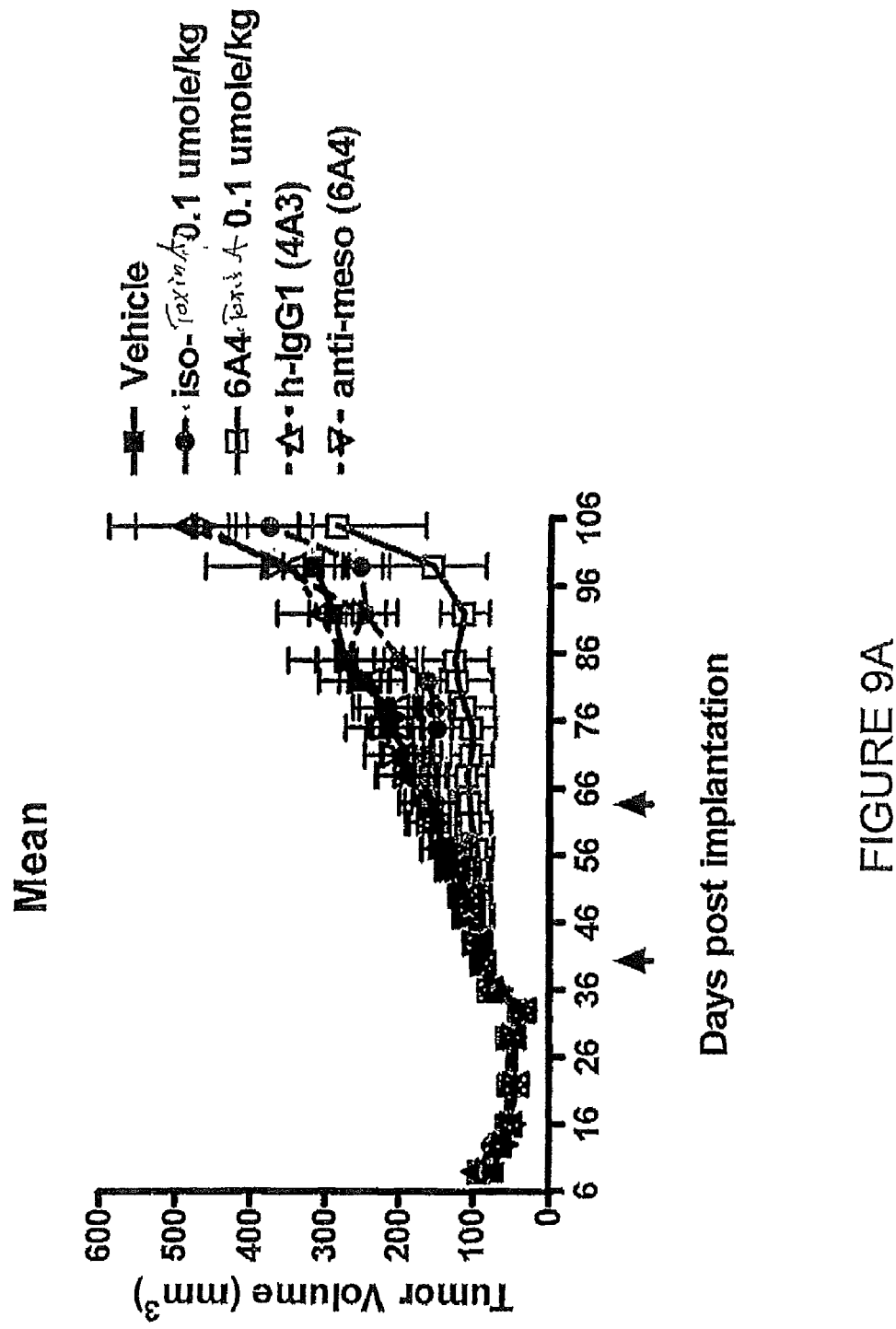
FIGS. 9A and 9B show the results of an in vivo study using an NCI-H226 (lung mesothelioma) xenograft mouse model.
Figure 9B:
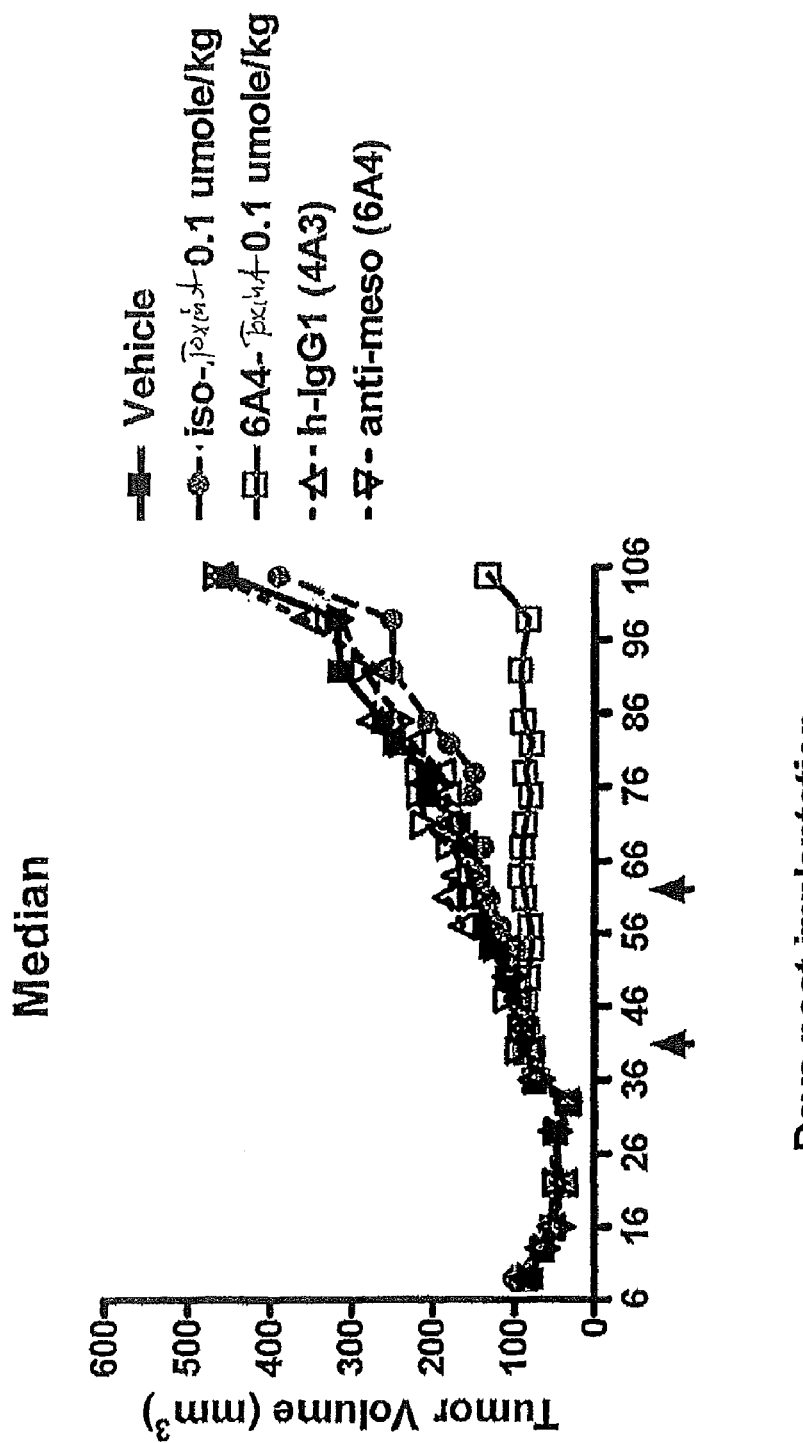

FIGS. 9A and 9B show the mean tumor volume and median tumor volume, respectively, in mice treated with vehicle alone, 6A4-Cytotoxin A (0.1 µmole/kg), iso-Cytotoxin A (0.1 µmole/kg), unconjugated 6A4 and unconjugated isotype control (4A3). As would be expected, given that the mouse xenograft model employed in the instant study is immuno-compromised and therefore would not be expected to mount a robust ADCC response, treatment with the naked 6A4 antibody did not show an effect on NCI-H226 tumor cell volume (i.e., did not inhibit tumor growth). In contrast, treatment with the 6A4-Cytotoxin A conjugate significantly inhibited tumor growth, as illustrated in the graphs of FIGS. 9A and 9B.

In a second series of analyses, the effect of 6A4 and 6A4-Cytotoxin A on the growth of HPAC cells (human pancreatic adenocarcinoma; ATCC Designation CRL-2119) in a mouse xenograft model was examined. HPAC cells ($5 \times 10^6$ cells/mouse) were implanted into CB17 SCID mice and allowed to grow for 8 days. On day 8, at which time the mean tumor volume was 96 mm$^3$, the mice were randomized and treated intraperitoneally (i.p.) with 6A4 (10 mg/kg or 30 mg/kg) or with 6A4-Cytotoxin A conjugate (0.15 mole/kg), along with controls: vehicle alone (PBS, Q3D×4), an isotype-matched human IgG1 antibody (4A3; 30 mg/kg) or an isotype-matched human IgG1 antibody linked to the Cytotoxin A cytotoxin (2A10-Cytotoxin A; 0.15 μmole/kg) and unconjugated 6A4 (8 mg/kg) or unconjugated isotype control (2A10; 8.7 mg/kg, SD) at equivalent protein dose. The 6A4 antibody, and its controls, were administered with a dose schedule of Q3D×4 (every three days for four times). The 6A4-Cytotoxin A conjugate, and its controls, were administered with a dose schedule of a single dose (SD). Tumor volume was measured at regular intervals until day 57.

Figure 10A:
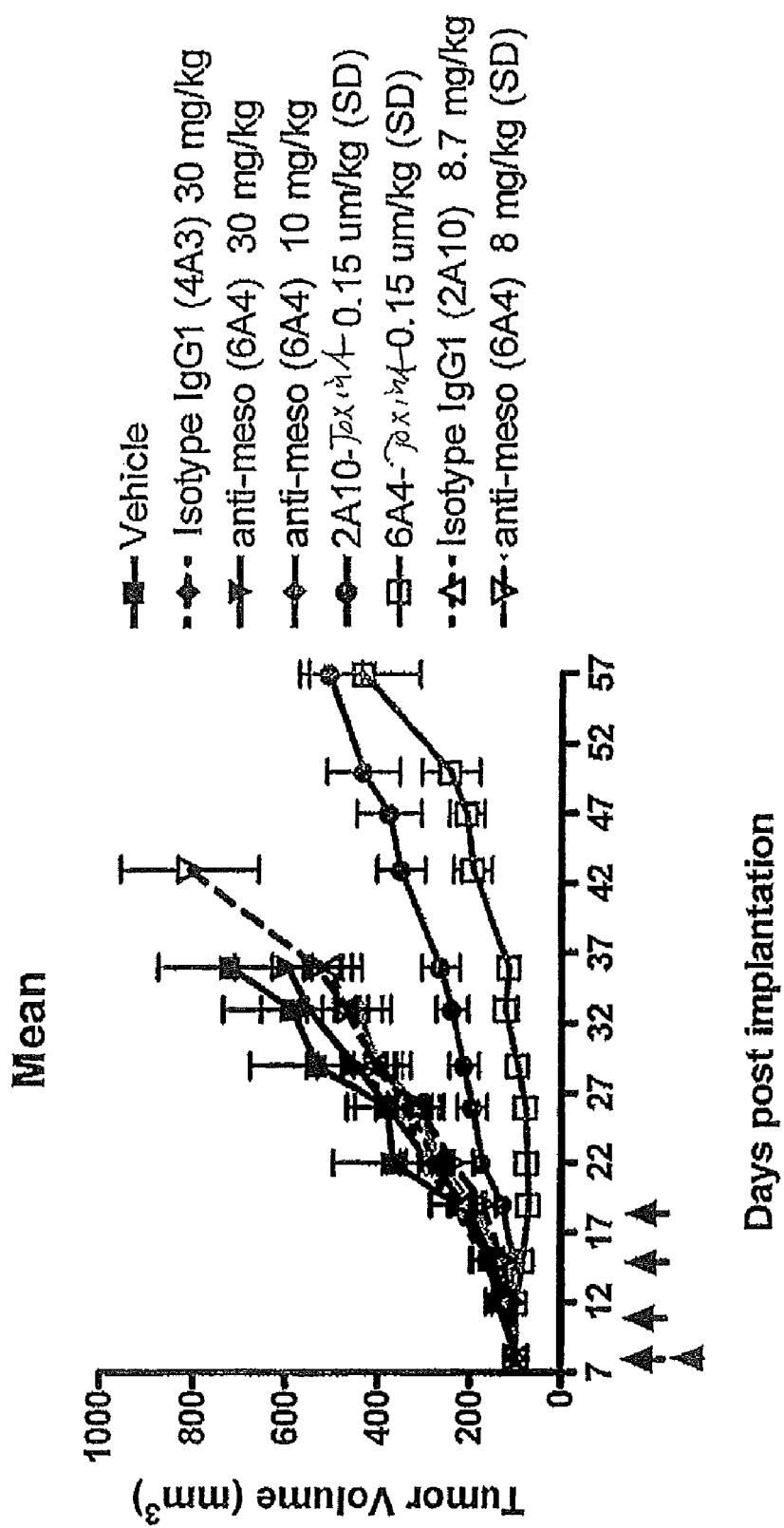
FIGS. 10A and 10B show the results of an in vivo study using an HPAC (human pancreatic carcinoma) xenograft mouse model.
Figure 10B:
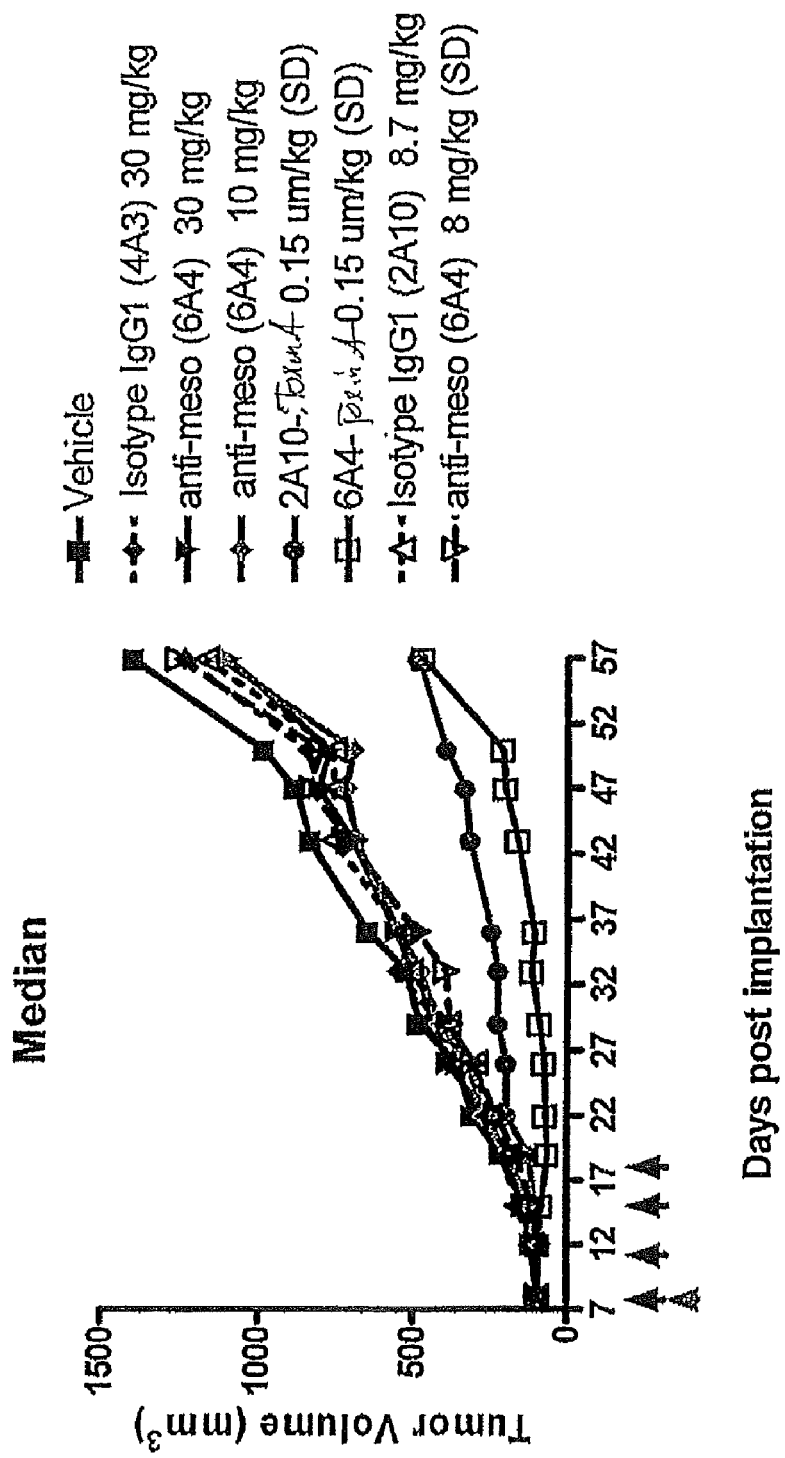

The results are shown in the graphs of FIGS. 10A and 10B. FIGS. 10A and 10B show the mean tumor volume and median tumor volume, respectively, in mice treated with vehicle alone, 6A4-Cytotoxin A (0.15 mole/kg), isotype-matched conjugate (2A10-Cytotoxin A; 0.15 μmole/kg), weight-equivalent unconjugated 6A4 (8 mg/kg), unconjugated isotype control (2A10; 8.7 mg/kg) at equivalent protein dose, naked 6A4 (10 mg/kg or 30 mg/kg) or isotype-matched IgG1 naked mAb (4A3; 30 mg/kg). The data indicate that treatment with the naked 6A4 antibody resulted in an inhibition of the growth of the HPAC tumor cells, even though the mouse xenograft model would not be expected to mount a robust ADCC response. Again, as was the case with the previous example, treatment with the 6A4-Cytotoxin A conjugate was shown to be very effective in inhibiting the growth of the HPAC tumor cells.

In a third series of analyses, the effect of 6A4-Cytotoxin A on the growth of ovarian cancer derived OVCAR3 cells (ATCC Designation HTB-161) in a mouse xenograft model was examined. In this xenograft model, CB17 SCID mice were implanted with 5×106 OVCAR3 cells per mouse and the OVCAR3 cells were allowed to grow for 42 days. On day 42, the mean tumor volume was approximately 100 mm3. The mice were treated intraperitoneally (i.p.) with 6A4-Cytotoxin A conjugate at a 0.1 or 0.3 μmole/kg dose. As controls, mice were treated with vehicle alone (PBS, Q3D×4) or 0.1 or 0.3 μmole/kg of an isotype-matched human IgG1 antibody linked to Cytotoxin A.

Figure 11:
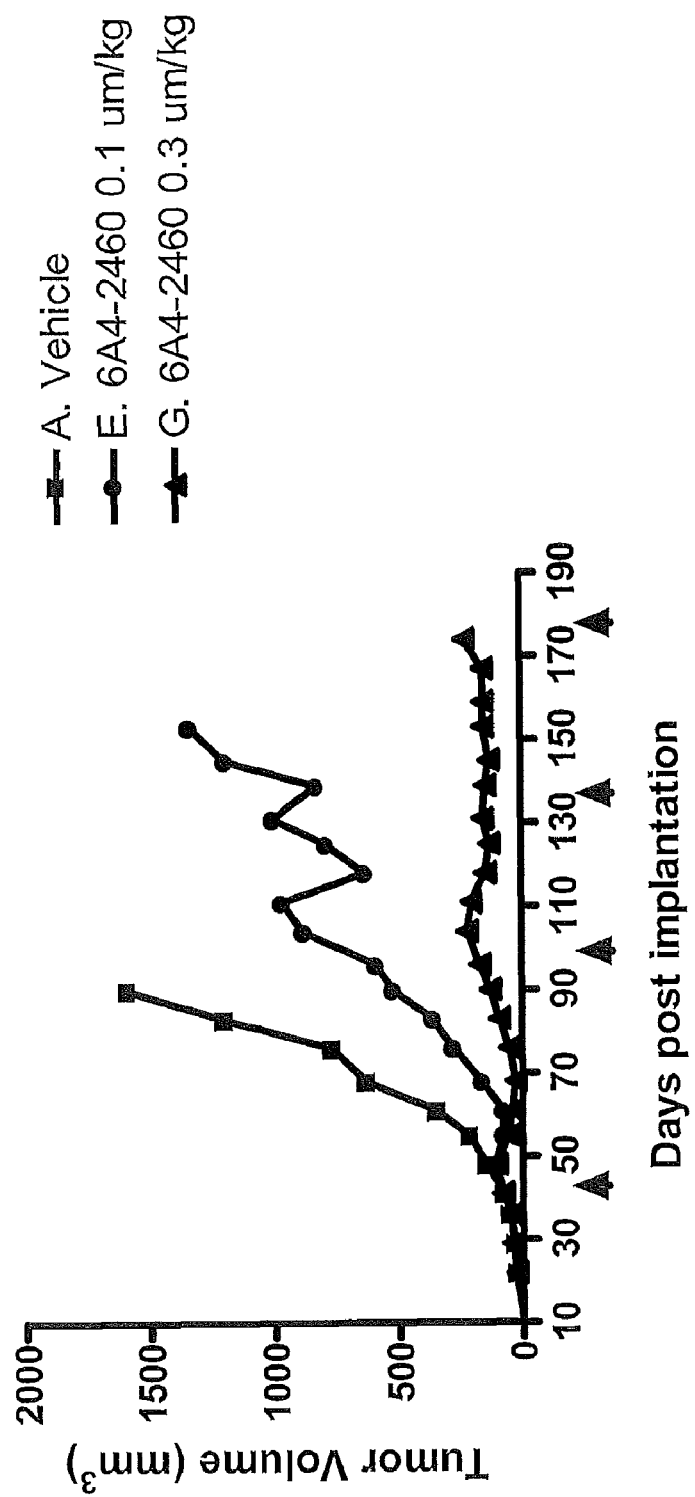
FIG. 11 is a graph showing that ovarian cancer tumor volumes were reduced an immunoconjugate of this invention in an ovarian cancer mouse xenograft model.

The 6A4-Cytotoxin A conjugate and its controls were administered on days 42, 96, 132 and 176. As shown in FIG. 11, treatment with the 6A4-Cytotoxin A conjugate significantly inhibited tumor growth. Tumor growth was controlled throughout this example, including through the final dosing at day 176, for the 0.3 μmol/kg dose of 6A4-Cytotoxin A. Tumor growth was controlled until day 150 with the 0.1 mol/kg dose of 6A4-Cytotoxin A. The isotype controls were not effective in controlling the tumors (data not shown).

In summary, a cytotoxin conjugate of 6A4 antibody (at a dose of 0.1-0.15 μmole/kg) significantly inhibited tumor growth in vivo in three different xenograft mouse models.

Example 9

ADCC Mediated by Non-Fucosylated 6A4

In this example, non-fucosylated 6A4 (6A4nf) antibodies were shown to be efficient mediators of ADCC in lung and ovarian cancers. A Delfia fluorescence emission analysis showed that non-fucosylated 6A4 killed mesothelin-expressing H226 (NSCLC) and OVCAR3 (ovarian cancer) cells in the presence of effector cells via ADCC. First, human effector cells were prepared from whole blood as follows: Human peripheral blood mononuclear cells were purified from heparinized whole blood by standard Ficoll-paque separation. The cells were resuspended in RPMI1640 media containing 10% FBS (heat-inactivated) and 200 U/mL of human IL-2 and incubated overnight at 37° C. The following day, the cells were collected and washed four times in culture media and resuspended at $2 \times 10^7$ cells/mL.

Figure 12A:
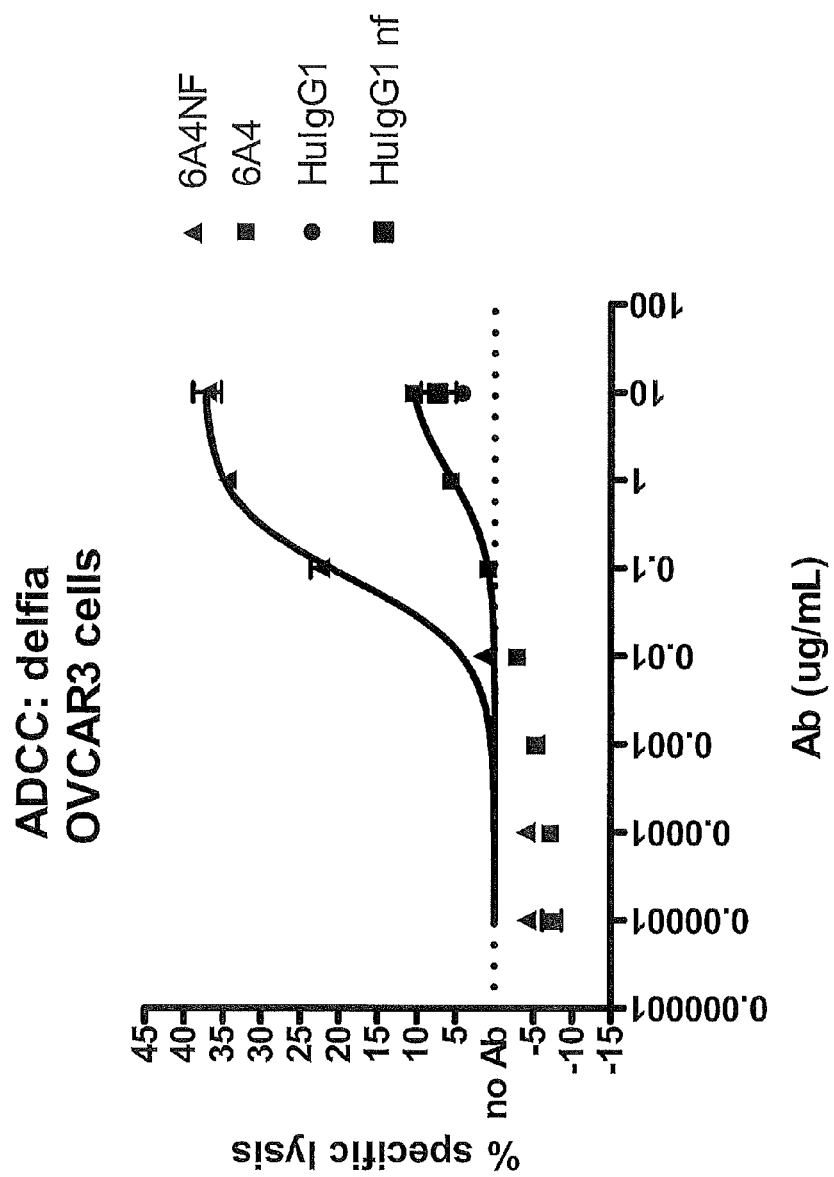
FIG. 12 shows ADCC of ovarian cancer cells (OVCAR3 cells, FIG. 12a) and NSCLC cells (H226 cells, FIG. 12b) by a non-fucosylated antibody of this invention.
Figure 12B:
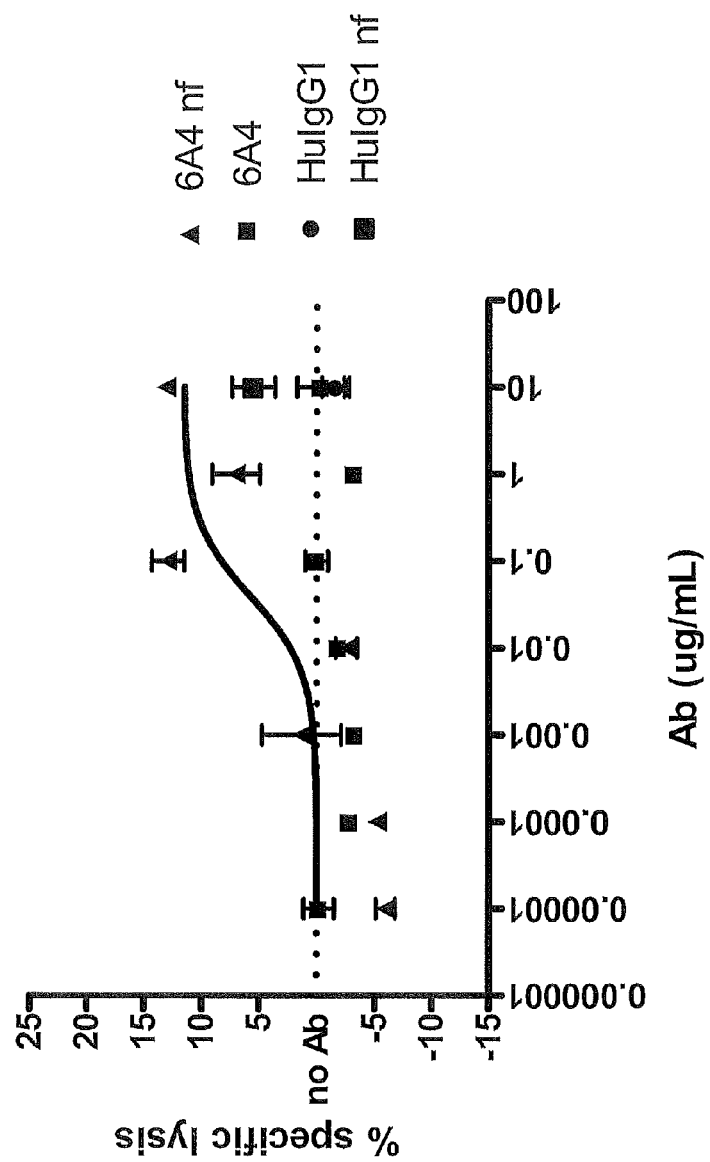

Second, labeled H226 or OVCAR3 cells were prepared by incubating them with BATDA reagent (Perkin Elmer, Wellesley, Mass.). Third, the target cells were mixed with effector cells and antibody. 100 μl of labeled target cells ($10^4$ cells/well) were incubated with 50 μl of effector cells ($10^6$ cells/well) and 50 μl of antibody (10 μg/mL final concentration). A target to effector ratio of 1:100 was used throughout the analyses. A human IgG1 (HuIgG1) isotype control was used as a negative control. Fourth, cell lysis was quantified. Cells were spun down at 2000 rpm and incubated for one hour incubation at 37° C. The supernatants were then collected, submitted to centrifugation and 20 μl of supernatant was transferred to a flat bottom plate. 180 μl of Eu solution (Perkin Elmer, Wellesley, Mass.) was added and read in a RubyStar reader (BMG Labtech). The percent lysis was calculated as follows: ((sample release−spontaneous release)×100) divided by (maximum release−spontaneous release) where the spontaneous release is the fluorescence from wells which contain target cells plus effector cells and maximum release is the fluorescence from wells containing target cells and have been treated with 2% Triton-X. Significant increases in ADCC activity was observed using non-fucosylated 6A4 on OVCAR3 cells (FIG. 12a) and H226 cells (FIG. 12b).

Example 10

Non-Fucosylated 6A4 Inhibited Tumor Growth In Vivo

In another example, 6A4nf, in combination with Gemcitabine, significantly slowed the growth of H226 cells in a mouse xenograft model. CB17 SCID mice were implanted with $9 \times 10^6$ H226 cells per mouse and the allowed to grow. On day 23, the mean tumor volume was approximately 100 mm3. The mice were randomized and treated intraperitoneally with 6A4nf, 80 mg/kg of Gemcitabine, the combination 6A4nf plus Gemcitabine, a vehicle control, or an IgG1 isotype control. 6A4nf was administered at either 10 mg/kg or 30 mg/kg. H226 growth was inhibited by all combinations of 6A4nf plus Gemcitabine. Maximal inhibition was achieved when 6A4nf was administered at 30 mg/kg in combination with Gemcitabine and suggested a dose-dependent effect.

Example 11

Mesothelin Expression on Tumor Cells

Immunohistochemistry using antibody 6A4 was used to show its ability to bind to human tumors and determine the range of expression of mesothelin in tumors. 6A4 was pre-complexed with a FITC-labeled Goat anti Human Fab (Jackson #109-097-003) so that the final concentration of 6A4 was 6 ug/mL. This complex was then used with standard IHC methods to determine binding. 6A4 was shown to bind to ovarian cancers, pancreatic cancers, lung cancers, mesotheliomas, and cancers of the head and neck. Additional examples of 6A4 binding to head and neck cancers include cancers from epiglottis, larynx, salivary gland, tongue, and tonsil tissues.

Example 12

6A4-Cytotoxin a is not Toxic in Cynomologus Monkeys

6A4-Cytotoxin A was shown to not be toxic in Cynomolgus monkeys. These animals show similar mesothelin expression patterns to those in humans. Also, the 6A4 antibody binds to the cynomolgus mesothelin protein with the same affinity as it does to the human mesothelin protein. Thus, cynomolgus monkeys were suitable to assess the on target toxicities of 6A4-Cytotoxin A.

6A4-Cytotoxin A was dosed intravenously to two male and two female cynomolgus monkeys. Two doses of 0.4 µmol/kg were given on days 1 and 15. The animals were observed for behavioral changes, signs of toxicity, and blood was drawn for analysis. The animals did not show signs of toxic effects.

On days 4, 3, 7, 14, 21, and 28, blood was drawn and multiple parameters were measured. No significant changes were observed in white blood cells, red blood cells, platelets, reticulocytes, neutrophil percentages, lymphocyte percentages, monocytes percentages, eosinophils percentages, basophile percentages, unstained cell percentages, hemoglobin, hematocrit, mcv, mch, mchc, protime, apt, albumin, total-protein, globulin, bilirubin, urea-nitrogen, creatinine, alkaline phosphatase, alanine transferase, aspartate transferase, glutamyl transferase, glucose, cholesterol, calcium, chloride, phosphorus, potassium, sodium, and triglycerides.

Following necropsy at day 28, no drug related changes were observed in the following organs: adrenal glands, aorta, sternum, brain, cecum, colon, duodenum, esophagus, eyes, optic nerve, femur, gallbladder, heart, ileum, jejunum, kidneys, lymph node, liver, lymph node, mes, lungs, mammary gland, sciatic nerve ovaries, pancreas, pituitary, parathyroid, rectum salivary gland, skin, skeletal muscle, spleen, stomach, thyroid glands, thymus, spinal cord, trachea, urinary bladder, uterus, vagina, cervix, injection site, oviducts, ureters, and peyer's patches.

SUMMARY OF SEQUENCE LISTING

| SEQ ID NO: | SEQUENCE |
|---|---|
| 1 | $V_H$ CDR1 a.a. 3C10 |
| 2 | $V_H$ CDR1 a.a. 6A4 |
| 3 | $V_H$ CDR1 a.a. 7B1 |
| 4 | $V_H$ CDR2 a.a. 3C10 |
| 5 | $V_H$ CDR2 a.a. 6A4 |
| 6 | $V_H$ CDR2 a.a. 7B1 |
| 7 | $V_H$ CDR3 a.a. 3C10 |
| 8 | $V_H$ CDR3 a.a. 6A4 |
| 9 | $V_H$ CDR3 a.a. 7B1 |
| 10 | $V_K$ CDR1 a.a. 3C10 |
| 11 | $V_K$ CDR1 a.a. 6A4 |
| 12 | $V_K$ CDR1 a.a. 7B1 |
| 13 | $V_K$ CDR2 a.a. 3C10 |
| 14 | $V_K$ CDR2 a.a. 6A4 |
| 15 | $V_K$ CDR2 a.a. 7B1 |
| 16 | $V_K$ CDR3 a.a. 3C10 |
| 17 | $V_K$ CDR3 a.a. 6A4 |
| 18 | $V_K$ CDR3 a.a. 7B1 |
| 19 | $V_H$ a.a. 3C10 |
| 20 | $V_H$ a.a. 6A4 |
| 21 | $V_H$ a.a. 7B1 |
| 22 | $V_K$ a.a. 3C10 |
| 23 | $V_K$ a.a. 6A4 |
| 24 | $V_K$ a.a. 7B1 |
| 25 | $V_H$ n.t. 3C10 |
| 26 | $V_H$ n.t. 6A4 |
| 27 | $V_H$ n.t. 7B1 |
| 28 | $V_K$ n.t. 3C10 |
| 29 | $V_K$ n.t. 6A4 |
| 30 | $V_K$ n.t. 7B1 |
| 31 | $V_H$ 3-33 germline a.a. |
| 32 | $V_H$ 3-7 germline a.a. |
| 33 | $V_k$ L6 germline a.a. |
| 34 | $V_k$ A27 germline a.a. |
| 35 | 3C10 VH fragment presented in FIG. 4 |
| 36 | 6A4 VH fragment presented in FIG. 4 |
| 37 | JK4 fragment presented in FIG. 5 |
| 38 | JH6b fragment presented in FIG. 6 |
| 39 | JK2 fragment presented in FIG. 7 |
| 40 | Peptide conjugate sequence |
| 41 | Peptide conjugate sequence |
| 42 | Peptide conjugate sequence |
| 43 | Peptide conjugate sequence |

What is claimed:

1. An isolated human monoclonal antibody, or an antigen-binding portion thereof, wherein the antibody binds human mesothelin and exhibits at least one, two, three, four or all five of the following properties:
   (a) binds to human mesothelin with a $K_D$ of $1\times10^{-8}$ M or less;
   (b) is internalized by mesothelin-expressing cells;
   (c) inhibits binding of mesothelin to ovarian cancer antigen CA125;
   (d) exhibits antibody dependent cellular cytotoxicity (ADCC) against mesothelin-expressing cells; or
   (e) inhibits growth of mesothelin-expressing cells in vivo when conjugated to a cytotoxin;
said isolated human monoclonal antibody, or antigen-binding portion thereof comprising
   (i) a heavy chain variable region CDR1 comprising SEQ ID NO:3;
   (ii) a heavy chain variable region CDR2 comprising SEQ ID NO:6;
   (iii) a heavy chain variable region CDR3 comprising SEQ ID NO:9;
   (iv) a light chain variable region CDR1 comprising SEQ ID NO:12;
   (v) a light chain variable region CDR2 comprising SEQ ID NO:15; and
   (vi) a light chain variable region CDR3 comprising SEQ ID NO:18.

2. The isolated human monoclonal antibody, or an antigen-binding portion thereof, of claim 1, which binds to human mesothelin with a $K_D$ of $5\times10^{-9}$ M or less.

3. The isolated monoclonal antibody, or antigen binding portion thereof, of claim 1 comprising:
   (a) a heavy chain variable region comprising the amino acid sequence of SEQ ID NO:21; and
   (b) a light chain variable region comprising the amino acid sequence of SEQ ID NO:24;
wherein the antibody specifically binds a human mesothelin protein.

4. A composition comprising the antibody, or antigen-binding portion thereof, of claim 1, and a pharmaceutically acceptable carrier.

5. A composition comprising the antibody, or antigen-binding portion thereof, of claim 1, conjugated to a partner molecule, and wherein the partner molecule is a therapeutic agent.

6. The composition of claim 5, wherein the therapeutic agent is a cytotoxin.

7. The isolated human monoclonal antibody, or an antigen binding fragment thereof, of claim 1, wherein said isolated human monoclonal antibody, or antigen binding portion thereof, lacks fucose residues.

* * * * *

SEQUENCE LISTING

```
<160> NUMBER OF SEQ ID NOS: 43

<210> SEQ ID NO 1
<211> LENGTH: 5
<212> TYPE: PRT
<213> ORGANISM: Homo sapiens

<400> SEQUENCE: 1

Ile Tyr Gly Met His
1               5

<210> SEQ ID NO 2
```

```
<211> LENGTH: 5
<212> TYPE: PRT
<213> ORGANISM: Homo sapiens

<400> SEQUENCE: 2

Ile Tyr Gly Met His
1               5

<210> SEQ ID NO 3
<211> LENGTH: 5
<212> TYPE: PRT
<213> ORGANISM: Homo sapiens

<400> SEQUENCE: 3

Arg Tyr Trp Met Ser
1               5

<210> SEQ ID NO 4
<211> LENGTH: 17
<212> TYPE: PRT
<213> ORGANISM: Homo sapiens

<400> SEQUENCE: 4

Val Ile Trp Tyr Asp Gly Ser His Glu Tyr Tyr Ala Asp Ser Val Lys
1               5                   10                  15
Gly

<210> SEQ ID NO 5
<211> LENGTH: 17
<212> TYPE: PRT
<213> ORGANISM: Homo sapiens

<400> SEQUENCE: 5

Val Leu Trp Tyr Asp Gly Ser His Glu Tyr Tyr Ala Asp Ser Val Lys
1               5                   10                  15
Gly

<210> SEQ ID NO 6
<211> LENGTH: 17
<212> TYPE: PRT
<213> ORGANISM: Homo sapiens

<400> SEQUENCE: 6

Ser Ile Lys Gln Ala Gly Ser Glu Lys Thr Tyr Val Asp Ser Val Lys
1               5                   10                  15
Gly

<210> SEQ ID NO 7
<211> LENGTH: 13
<212> TYPE: PRT
<213> ORGANISM: Homo sapiens

<400> SEQUENCE: 7

Asp Gly Asp Tyr Tyr Asp Ser Gly Ser Pro Leu Asp Tyr
1               5                   10

<210> SEQ ID NO 8
<211> LENGTH: 13
<212> TYPE: PRT
<213> ORGANISM: Homo sapiens

<400> SEQUENCE: 8

Asp Gly Asp Tyr Tyr Asp Ser Gly Ser Pro Leu Asp Tyr
1               5                   10
```

<210> SEQ ID NO 9
<211> LENGTH: 22
<212> TYPE: PRT
<213> ORGANISM: Homo sapiens

<400> SEQUENCE: 9

Glu Gly Ala Tyr Tyr Asp Ser Ala Ser Tyr Tyr Pro Tyr Tyr
1               5                   10                  15

Tyr Tyr Ser Met Asp Val
            20

<210> SEQ ID NO 10
<211> LENGTH: 11
<212> TYPE: PRT
<213> ORGANISM: Homo sapiens

<400> SEQUENCE: 10

Arg Ala Ser Gln Ser Val Ser Ser Tyr Leu Ala
1               5                   10

<210> SEQ ID NO 11
<211> LENGTH: 11
<212> TYPE: PRT
<213> ORGANISM: Homo sapiens

<400> SEQUENCE: 11

Arg Ala Ser Gln Ser Val Ser Ser Tyr Leu Ala
1               5                   10

<210> SEQ ID NO 12
<211> LENGTH: 12
<212> TYPE: PRT
<213> ORGANISM: Homo sapiens

<400> SEQUENCE: 12

Arg Ala Ser Gln Ser Val Ser Ser Ser Tyr Leu Ala
1               5                   10

<210> SEQ ID NO 13
<211> LENGTH: 7
<212> TYPE: PRT
<213> ORGANISM: Homo sapiens

<400> SEQUENCE: 13

Asp Ala Ser Asn Arg Ala Thr
1               5

<210> SEQ ID NO 14
<211> LENGTH: 7
<212> TYPE: PRT
<213> ORGANISM: Homo sapiens

<400> SEQUENCE: 14

Asp Ala Ser Asn Arg Ala Thr
1               5

<210> SEQ ID NO 15
<211> LENGTH: 7
<212> TYPE: PRT
<213> ORGANISM: Homo sapiens

<400> SEQUENCE: 15

Gly Ala Ser Ser Arg Ala Thr
1               5

<210> SEQ ID NO 16
<211> LENGTH: 9
<212> TYPE: PRT
<213> ORGANISM: Homo sapiens

<400> SEQUENCE: 16

Gln Gln Arg Ser Asn Trp Pro Leu Thr
1               5

<210> SEQ ID NO 17
<211> LENGTH: 9
<212> TYPE: PRT
<213> ORGANISM: Homo sapiens

<400> SEQUENCE: 17

Gln Gln Arg Ser Asn Trp Pro Leu Thr
1               5

<210> SEQ ID NO 18
<211> LENGTH: 9
<212> TYPE: PRT
<213> ORGANISM: Homo sapiens

<400> SEQUENCE: 18

Gln Gln Tyr Gly Ser Ser Gln Tyr Thr
1               5

<210> SEQ ID NO 19
<211> LENGTH: 122
<212> TYPE: PRT
<213> ORGANISM: Homo sapiens

<400> SEQUENCE: 19

Gln Val Tyr Leu Val Glu Ser Gly Gly Gly Val Val Gln Pro Gly Arg
1               5                   10                  15

Ser Leu Arg Leu Ser Cys Ala Ala Ser Gly Ile Thr Phe Ser Ile Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser His Glu Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Asn Ser Leu Arg Ala Glu Asp Thr Ala Val Tyr Tyr Cys
                85                  90                  95

Ala Arg Asp Gly Asp Tyr Tyr Asp Ser Gly Ser Pro Leu Asp Tyr Trp
            100                 105                 110

Gly Gln Gly Thr Leu Val Thr Val Ser Ser
        115                 120

<210> SEQ ID NO 20
<211> LENGTH: 122
<212> TYPE: PRT
<213> ORGANISM: Homo sapiens

<400> SEQUENCE: 20

Gln Val His Leu Val Glu Ser Gly Gly Gly Val Val Gln Pro Gly Arg
1               5                   10                  15

Ser Leu Arg Leu Ser Cys Val Ala Ser Gly Ile Thr Phe Arg Ile Tyr
            20                  25                  30

```
Gly Met His Trp Val Arg Gln Ala Pro Gly Lys Gly Leu Glu Trp Val
            35                  40                  45
Ala Val Leu Trp Tyr Asp Gly Ser His Glu Tyr Tyr Ala Asp Ser Val
        50                  55                  60
Lys Gly Arg Phe Thr Ile Ser Arg Asp Asn Ser Lys Asn Thr Leu Tyr
 65                  70                  75                  80
Leu Gln Met Asn Ser Leu Arg Ala Glu Asp Thr Ala Ile Tyr Tyr Cys
                85                  90                  95
Ala Arg Asp Gly Asp Tyr Tyr Asp Ser Gly Ser Pro Leu Asp Tyr Trp
            100                 105                 110
Gly Gln Gly Thr Leu Val Thr Val Ser Ser
        115                 120
```

<210> SEQ ID NO 21
<211> LENGTH: 131
<212> TYPE: PRT
<213> ORGANISM: Homo sapiens

<400> SEQUENCE: 21

```
Glu Val His Leu Val Glu Ser Gly Gly Leu Val Gln Pro Gly Gly
 1               5                  10                  15
Ser Leu Arg Leu Ser Cys Ala Ala Ser Gly Phe Thr Phe Ser Arg Tyr
            20                  25                  30
Trp Met Ser Trp Val Arg Gln Ala Gln Gly Lys Gly Leu Glu Trp Val
            35                  40                  45
Ala Ser Ile Lys Gln Ala Gly Ser Glu Lys Thr Tyr Val Asp Ser Val
        50                  55                  60
Lys Gly Arg Phe Thr Ile Ser Arg Asp Asn Ala Lys Asn Ser Leu Ser
 65                  70                  75                  80
Leu Gln Met Asn Ser Leu Arg Ala Glu Asp Thr Ala Val Tyr Tyr Cys
                85                  90                  95
Ala Arg Glu Gly Ala Tyr Tyr Tyr Asp Ser Ala Ser Tyr Tyr Pro Tyr
            100                 105                 110
Tyr Tyr Tyr Tyr Ser Met Asp Val Trp Gly Gln Gly Thr Thr Val Thr
            115                 120                 125
Val Ser Ser
    130
```

<210> SEQ ID NO 22
<211> LENGTH: 107
<212> TYPE: PRT
<213> ORGANISM: Homo sapiens

<400> SEQUENCE: 22

```
Glu Ile Val Leu Thr Gln Ser Pro Ala Thr Leu Ser Leu Ser Pro Gly
 1               5                  10                  15
Glu Arg Ala Thr Leu Ser Cys Arg Ala Ser Gln Ser Val Ser Ser Tyr
            20                  25                  30
Leu Ala Trp Tyr Gln Gln Lys Pro Gly Gln Ala Pro Arg Leu Leu Ile
            35                  40                  45
Tyr Asp Ala Ser Asn Arg Ala Thr Gly Ile Pro Ala Arg Phe Ser Gly
        50                  55                  60
Ser Gly Ser Gly Thr Asp Phe Thr Leu Thr Ile Ser Ser Leu Glu Pro
 65                  70                  75                  80
Glu Asp Phe Ala Val Tyr Tyr Cys Gln Gln Arg Ser Asn Trp Pro Leu
                85                  90                  95
Thr Phe Gly Gly Gly Thr Lys Val Glu Ile Lys
```

<210> SEQ ID NO 23
<211> LENGTH: 107
<212> TYPE: PRT
<213> ORGANISM: Homo sapiens

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 24
<211> LENGTH: 108
<212> TYPE: PRT
<213> ORGANISM: Homo sapiens

<400> SEQUENCE: 24

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Gln
                85                  90                  95

Tyr Thr Phe Gly Gln Gly Thr Lys Leu Glu Ile Lys
            100                 105

<210> SEQ ID NO 25
<211> LENGTH: 366
<212> TYPE: DNA
<213> ORGANISM: Homo sapiens

<400> SEQUENCE: 25
caggtgtacc tggtggagtc tgggggaggc gtggtccagc ccggggaggtc cctgagactc      60 tcctgtgcag cgtctggaat caccttcagt atctatggca tgcactgggt ccgccaggct     120
ccaggcaagg ggctggagtg gtggcagtt atatggtatg atggaagtca tgaatactat     180
gcagactccg tgaagggccg attcaccatc tccagagaca attccaagaa cacgctgtat     240
ctgctaatga acagcctgag agccgaggac acggctgtgt attactgtgc gagagatggc     300
gattattatg attcggggag tcctcttgac tactggggcc agggaaccct ggtcaccgtc     360

```
tcctca                                                              366

<210> SEQ ID NO 26
<211> LENGTH: 366
<212> TYPE: DNA
<213> ORGANISM: Homo sapiens

<400> SEQUENCE: 26
caggtgcacc tggtggagtc tgggggaggc gtggtccagc ctgggaggtc cctgagactc     60
tcctgtgtag cgtctggaat caccttcagg atctatggca tgcactgggt ccgccaggct    120
ccaggcaagg ggctggagtg ggtggcagtt ttatggtatg atggaagtca tgaatactat    180
gcagactccg tgaagggccg attcaccatc tccagagaca attccaagaa cacgctatat    240
ctgcaaatga acagcctgag agccgaggac acggctatat attactgtgc gagagatggc    300
gattactatg attcggggag tcctcttgac tactggggcc agggaaccct ggtcaccgtc    360
tcctca                                                              366

<210> SEQ ID NO 27
<211> LENGTH: 393
<212> TYPE: DNA
<213> ORGANISM: Homo sapiens

<400> SEQUENCE: 27
gaggttcacc tggtggagtc tgggggaggc ttggtccagc ctgggggtc cctgagactc      60 tcctgtgcag cctctggatt cacctttagt agatactgga tgagctgggt ccgccaggct    120
caagggaaag ggctggagtg ggtggccagc ataaagcaag ctggaagtga gaaaacctat    180
gtggactctg tgaagggccg attcaccatc tccagagaca cgccaagaa ctcactgtct     240 ctgcaaatga acagcctgag agccgaggac acggctgttt attactgtgc gagggagggg    300
gcatattact atgattcggc gagttattac ccttactact actactacag tatggacgtc    360
tggggccaag ggaccacggt caccgtctcc tca                                 393

<210> SEQ ID NO 28
<211> LENGTH: 321
<212> TYPE: DNA
<213> ORGANISM: Homo sapiens

<400> SEQUENCE: 28
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggccgctcac tttcggcgga    300
gggaccaagg tggagatcaa a                                              321

<210> SEQ ID NO 29
<211> LENGTH: 321
<212> TYPE: DNA
<213> ORGANISM: Homo sapiens

<400> SEQUENCE: 29
gaaattgtgt tgacacagtc tccagccacc ctgtctttgt ctccagggga aagagccacc     60
ctctcctgca gggccagtca gagtgttagc agctacttag cctggtacca acagaaacct    120
ggccaggctc ccaggctcct catctatgat gcatccaaca gggccactgg catcccagcc    180
```

```
aggttcagtg gcagtgggtc tgggacagac ttcactctca ccatcagcag cctagagcct        240
gaagattttg cagtttatta ctgtcagcag cgtagcaact ggccgctcac tttcggcgga        300
gggaccaagg tggagatcaa a                                                  321
```

<210> SEQ ID NO 30
<211> LENGTH: 318
<212> TYPE: DNA
<213> ORGANISM: Homo sapiens

<400> SEQUENCE: 30

```
gtgttgacgc agtctccagg caccctgtct ttgtctccag ggaaagagc caccctctcc          60 tgcagggcca gtcagagtgt tagcagcagc tacttagcct ggtaccagca gaaacctggc        120
caggctccca ggctcctcat ctatggtgca tccagcaggg ccactggcat cccagacagg        180
ttcagtggca gtgggtctgg gacagacttc actctcacca tcagcagact ggagcctgaa        240
gattttgcag tgtattactg tcagcagtat ggtagctcac agtacacttt tggccagggg        300
accaagctgg agatcaaa                                                      318
```

<210> SEQ ID NO 31
<211> LENGTH: 98
<212> TYPE: PRT
<213> ORGANISM: Homo sapiens

<400> SEQUENCE: 31

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg
```

<210> SEQ ID NO 32
<211> LENGTH: 98
<212> TYPE: PRT
<213> ORGANISM: Homo sapiens

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95
```

Ala Arg

<210> SEQ ID NO 33
<211> LENGTH: 95
<212> TYPE: PRT
<213> ORGANISM: Homo sapiens

<400> SEQUENCE: 33

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro
                85                  90                  95

<210> SEQ ID NO 34
<211> LENGTH: 95
<212> TYPE: PRT
<213> ORGANISM: Homo sapiens

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser
                85                  90                  95

<210> SEQ ID NO 35
<211> LENGTH: 11
<212> TYPE: PRT
<213> ORGANISM: Homo sapiens

<400> SEQUENCE: 35

Asp Gly Asp Tyr Tyr Asp Ser Gly Ser Pro Leu
1               5                   10

<210> SEQ ID NO 36
<211> LENGTH: 11
<212> TYPE: PRT
<213> ORGANISM: Homo sapiens

<400> SEQUENCE: 36

Asp Gly Asp Tyr Tyr Asp Ser Gly Ser Pro Leu
1               5                   10

<210> SEQ ID NO 37
<211> LENGTH: 12
<212> TYPE: PRT

```
<213> ORGANISM: Homo sapiens

<400> SEQUENCE: 37

Leu Thr Phe Gly Gly Gly Thr Lys Val Glu Ile Lys
1               5                   10

<210> SEQ ID NO 38
<211> LENGTH: 13
<212> TYPE: PRT
<213> ORGANISM: Homo sapiens

<400> SEQUENCE: 38

Glu Gly Ala Tyr Tyr Tyr Asp Ser Ala Ser Tyr Tyr Pro
1               5                   10

<210> SEQ ID NO 39
<211> LENGTH: 12
<212> TYPE: PRT
<213> ORGANISM: Homo sapiens

<400> SEQUENCE: 39

Tyr Thr Phe Gly Gln Gly Thr Lys Leu Glu Ile Lys
1               5                   10

<210> SEQ ID NO 40
<211> LENGTH: 4
<212> TYPE: PRT
<213> ORGANISM: Artificial Sequence
<220> FEATURE:
<223> OTHER INFORMATION: Peptide conjugate sequence

<400> SEQUENCE: 40

Ala Leu Ala Leu
1

<210> SEQ ID NO 41
<211> LENGTH: 4
<212> TYPE: PRT
<213> ORGANISM: Artificial Sequence
<220> FEATURE:
<223> OTHER INFORMATION: Peptide conjugate sequence
<220> FEATURE:
<221> NAME/KEY: MISC_FEATURE
<222> LOCATION: (1)..(1)
<223> OTHER INFORMATION: X = Beta-alanine

<400> SEQUENCE: 41

Xaa Leu Ala Leu
1

<210> SEQ ID NO 42
<211> LENGTH: 4
<212> TYPE: PRT
<213> ORGANISM: Artificial Sequence
<220> FEATURE:
<223> OTHER INFORMATION: Peptide conjugate sequence

<400> SEQUENCE: 42

Gly Phe Leu Gly
1

<210> SEQ ID NO 43
<211> LENGTH: 4
<212> TYPE: PRT
<213> ORGANISM: Artificial Sequence
```

```
<220> FEATURE:
<223> OTHER INFORMATION: Peptide conjugate sequence

<400> SEQUENCE: 43

Leu Leu Gly Leu
1
```